US010711022B2

United States Patent
Pan et al.

(10) Patent No.: US 10,711,022 B2
(45) Date of Patent: Jul. 14, 2020

(54) METHODS OF PRODUCING OLIGOSACCHARIDES FOR USE AS PREBIOTICS

(71) Applicant: Wisconsin Alumni Research Foundation, Madison, WI (US)

(72) Inventors: Xuejun Pan, Madison, WI (US); Ning Li, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/232,575

(22) Filed: Dec. 26, 2018

(65) Prior Publication Data

US 2019/0194239 A1  Jun. 27, 2019

Related U.S. Application Data

(60) Provisional application No. 62/610,472, filed on Dec. 26, 2017.

(51) Int. Cl.
| | |
|---|---|
| *C07H 3/06* | (2006.01) |
| *C08B 37/00* | (2006.01) |
| *C07H 1/00* | (2006.01) |
| *C07H 1/08* | (2006.01) |

(52) U.S. Cl.
CPC ............... *C07H 3/06* (2013.01); *C07H 1/00* (2013.01); *C07H 1/08* (2013.01); *C08B 37/00* (2013.01)

(58) Field of Classification Search
None
See application file for complete search history.

(56) References Cited

PUBLICATIONS

Kanazawa, Org. Biomol. Chem., 2005, 3, 1746-1750. (Year: 2005).*
Ohno, J Wood Sci (2015) 61:165-170 . (Year: 2015).*
Abdul Manas et al.; Strategy in Manipulating Transglycosylation Activity of Glycosyl Hydrolase for Oligosaccharide Production; 2017; 23 pages.
De Almeida et al.; Cellulose Conversion to Isosorbide in Molten Salt Hydrate Media; 2010; 4 pages.
Helm et al.; The Reversion Reaction of D-Glucose During the Hydrolysis of Cellulose with Dilute Sulfuric Acid; 1989; 12 pages.
Himmel et al.; Biomass Recalcitrance: Engineering Plants and Enymes for Biofuels Production; 2007; 5 pages.
Kato et al.; Novel Glucosidase From Aspergillus Nidulans with Strong Transglycosylation Activity; 2002; 7 pages.
Kaufman Rechulski et al.; Mechanocatalytic Depolymerization of Lignocellulose Performed on Hectogram and Kilogram Scales; 2015; 12 pages.
Kaulpiboon et al.; Synthesis of Long-Chain Isomaltooligosaccharides from Tapioca Starch and an In Vitro Investigation of Their Prebiotic Properties; 2015; 9 pages.
Li et al.; A Facile and Fast Method of Quantitating Lignin in Lignocellulosic Biomass using Acidic Lithium Bromide Trihydrate (ALBTH); 2016; 10 pages.
Meine et al.; Solvent-Free Catalytic Depolymerization of Cellulose to Water-Soluble Oligosaccharides; 2012; 6 pages.
Ohno et al.; Production of Disaccharides from Glucose by Treatment with an Ionic Liquid, 1-ethyl-3-methylimidozolium Chloride; 2015; 6 pages.
Pilath et al.; Glucose Reversion Reaction Kinetics; 2010; 10 pages.
Pilath et al.; Investigation of Xylose Reversion Reactions That Can Occur During Dilute Acid Pretreatment; 2013; 9 pages.
Plou et al.; Industrial Enzymes; Structure, Function and Applications; 2007; 633 pages.
Qian; Mechanisms and Energetics for Bronsted Acid-Catalyzed Glucose Condensation, Dehydration, and Isomerization Reactions; 2012; 9 pages.
Rinaldi, et al.; Depolymerization of Cellulose Using Solid Catalysts in Ionic Liquids; 2008; 4 pages.
Rycroft et al.; Fermentation Properties of Gentio-Oligosaccharides; 2001; 6 pages.
Sanz et al.; Influence of Disaccharide Structure on Prebiotic Selectivity in Vitro; 2005; 8 pages.
Thompson et al.; Acid Reversion Products from D-Glucose; 1954; 3 pages.
Yoo et al.; Effective Conversion of Biomass into Bromomethylfurfural, Furfural, and Depolymerized Lignin in Lithium Bromide Molten Salt Hydrate of a Biphasic System; 2017; 9 pages.

* cited by examiner

*Primary Examiner* — Layla D Berry
(74) *Attorney, Agent, or Firm* — Foley & Lardner LLP

(57) ABSTRACT

Provided herein are methods for preparing prebiotic oligosaccharides by non-enzymatic methods of glycosylation of monosaccharides and/or disaccharides or by hydrolysis of polymeric sugars to monosaccharides and simultaneous glycosylation of hydrolytic products. The methods may include mixing one or more types of monosaccharides and/or disaccharides with a water-deficient system at a temperature sufficient to form one or more types of prebiotic oligosaccharides. Also provided are methods of preparing prebiotic oligosaccharides comprising mixing starch, cellulose and/or lignocellulosic biomass with a water-deficient system at a temperature sufficient to form one or more types of prebiotic oligosaccharides that collectively make up at least 25% of the products of the synthesis.

22 Claims, 25 Drawing Sheets

FIG. 11C

MS peak assignment

| # | GnXm-M | Mass (m/z) | Intensity (%) 30 min | Intensity (%) 60 min |
|---|--------|------------|------|------|
| 1 | X2-Li | 289.1 | | 15.5 |
| 2 | GX-Li | 319.1 | | 55.0 |
| 3 | GX-Na | 335.1 | 5.0 | 23.4 |
| 4 | G2-Li | 349.1 | | 100.0 |
| 5 | G2-Na | 365.1 | 35.4 | 66.6 |
| 6 | G2-K | 381.1 | 9.6 | 33.6 |
| 7 | GX2-Li | 451.2 | | 15.1 |
| 8 | GX2-Na | 467.1 | | 4.9 |
| 9 | G2X-Li | 481.2 | | 54.4 |
| 10 | G2X-Na | 497.2 | 18.1 | 16.7 |
| 11 | G3-Li | 511.2 | | 75.7 |
| 12 | G3-Na | 527.2 | 90.8 | 30.5 |
| 13 | G3-K | 543.1 | 12.8 | 30.5 |
| 14 | G2X2-Li | 613.2 | | 8.0 |
| 15 | G3X-Li | 643.3 | | 28.5 |
| 16 | G3X-Na | 659.2 | 36.6 | 6.9 |
| 17 | G4-Li | 673.3 | | 46.8 |
| 18 | G4-Na | 689.3 | 100.0 | 11.5 |
| 19 | G4-K | 705.2 | 12.8 | 4.4 |
| 20 | G3X2-Li | 775.3 | | 3.8 |
| 21 | G4X-Li | 805.3 | | 12.6 |
| 22 | G4X-Na | 821.3 | 29.3 | 2.9 |
| 23 | G5-Li | 835.4 | | 20.1 |
| 24 | G5-Na | 851.3 | 60.4 | 4.8 |
| 25 | G5-K | 867.3 | 7.5 | 2.0 |

METHODS OF PRODUCING OLIGOSACCHARIDES FOR USE AS PREBIOTICS

PRIORITY

This application is a U.S. utility application claims priority to U.S. Provisional Patent Application No. 62/610,472, filed on Dec. 26, 2017, the entire contents of which are incorporated herein by reference in their entireties.

GOVERNMENT RIGHTS

This invention was made with government support under CBET 1159561 awarded by the National Science Foundation and 17-CRHF-0-6055 awarded by the USDA NIFA. The government has certain rights in the invention.

FIELD

The present technology relates to non-enzymatic methods of preparing prebiotic oligosaccharides from monosaccharides and/or disaccharides using a water deficient system containing a metal salt and from simultaneous saccharification/glycosylation of cellulose and lignocellulose, also using a water deficient system containing a metal salt.

BACKGROUND

Certain oligosaccharides which are indigestible by humans may nevertheless serve as food for probiotic microorganisms and promote human health. Such oligosaccharides are known as prebiotics. Oligosaccharides are oligomers of sugar units (monosaccharides) linked by glycosidic bonds with degrees of polymerization (DP) from 2 to 10 or in some cases up to 20. Examples of prebiotic oligosaccharides include fructooligosaccharides (FOS), galactooligosaccharides (GOS), xylooligosaccharides (XOS), isomaltooligosaccharides (IMO), and pecticoligosaccharides (POS). Passing through the upper gastrointestinal tract intact, prebiotic oligosaccharides can be selectively metabolized by the beneficial bacteria in the colon, thus modulating the composition and/or activity of the gut microbiota and resulting in improvement to host health. The direct physiological benefits encompass stimulation of probiotic population such as *Bifidobacterium* and *Lactobacillus* strains and accumulation of metabolic end products, such as short-chain fatty acid (SCFA) in the colon. Besides the direct benefits above to hosts, a range of systemic health implications are recognized, including metabolic inhibition of pathogenic microorganisms, constipation alleviation, reduction of diet-induced obesity, improvement of mineral absorption, repression of allergic symptoms, enhancement of immune system, reduction of colon cancer, and modulation of cholesterol levels. The bioactivities and prebiotic functionalities of oligosaccharides depend on their sugar compositions, DP value, and glycosidic linkages.

At present, prebiotics are generally produced through either controlled hydrolysis of polysaccharides or direct synthesis from simple sugars. Methods using controlled hydrolysis of polysaccharides are limited by the starting polysaccharides since sugar compositions and glycosidic linkages of the oligosaccharides are mostly inherited from the parent polysaccharides and their supplies are limited. Enzymatic hydrolysis can be expensive and suitable enzymes of limited availability. Acid hydrolysis is cheaper, but may often induce sugar degradation and result in undesirable side-products. Synthesis of oligosaccharides from simple sugars using enzymes is also an expensive and problematic process in view of the challenges of identifying and synthesizing enzymes with high activity and selectivity, good stability and recyclability, low cost, and industrial feasibility. Non-enzymatic catalysts, especially acids, can also catalyze the glycosylation. However, challenges remain to prepare oligosaccharides with the degree of polymerization (DP)>2 while avoiding sugar degradation and other undesired byproducts.

SUMMARY

The present technology provides methods for preparing prebiotic oligosaccharides by non-enzymatic methods of glycosylation of monosaccharides and/or disaccharides or by hydrolysis of polymeric sugars to monosaccharides and/or disaccharides and simultaneous glycosylation of hydrolytic products. Thus, in one aspect, the present technology provides methods of preparing prebiotic oligosaccharides including mixing one or more types of monosaccharides and/or disaccharides with a water-deficient system at a temperature sufficient to form one or more types of prebiotic oligosaccharides, wherein the weight ratio of monosaccharides and/or disaccharides to water-deficient system is 0.01 to 10; and the water-deficient system comprises a metal salt selected from an alkali metal salt and/or an alkaline earth metal salt, water, and a catalytic amount of acid wherein the molar ratio of water to metal salt in the water-deficient system is about 2 to about 12; and the acid has a pKa of less than 4.

In another aspect the present technology provides methods of preparing prebiotic oligosaccharides comprising mixing starch, cellulose and/or lignocellulosic biomass with a water-deficient system at a temperature sufficient to form one or more types of prebiotic oligosaccharides that collectively make up at least 25% of the products of the synthesis, wherein the weight ratio of starch, cellulose and/or lignocellulosic biomass to water-deficient system is 0.05 to 10; and the water-deficient system comprises a metal salt selected from an alkali metal salt and/or an alkaline earth metal salt, water, and a catalytic amount of acid wherein the molar ratio of water to metal salt in the water-deficient system is about 2 to about 12; and the acid has a pKa of less than 4.

In some embodiments of any aspect of the present technology, the metal salt is one or more of LiBr, LiCl, NaBr, $CaCl_2$, $CaBr_2$, $MgCl_2$, NaI, LiI, $CaI_2$, $MgI_2$, $AlCl_3$, $AlBr_3$, $MgBr_2$, $ZnCl_2$, $ZnBr_2$, $LiClO_4$, $Ca(ClO_4)_2$, LiSCN, and $Ca(SCN)_2$. In certain embodiments, the metal salt is a lithium salt. In other embodiments, such as, but not limited to, lithium bromide.

In some embodiments of any aspect of the present technology, the molar ratio of water to metal salt in the water-deficient system is about 2 to about 5. In certain embodiments, the water deficient system is a solution.

In some embodiments of any aspect of the present technology, the acid has a pKa of about −10 to less than 4. The acid, for example, may be one or more selected from the group consisting of HCl, $H_2SO_4$, $HNO_3$, $H_3PO_4$, $CH_3SO_3H$, tosylic acid, oxalic acid, glyoxylic acid, lactic acid, citric acid, formic acid, and trifluoroacetic acid. In some embodiment, the water-deficient system may include 0.5 mM to 500 mM acid. In others, the acid concentration may range from 20 mM to 120 mM, or even 80 or 60 mM.

In some embodiments of any aspect of the present technology, the monosaccharides and/or disaccharides include glucose, fructose, galactose, xylose, mannose, arabinose, sucrose, lactose, maltose, cellobiose, apiose, rhamnose, hydrolyzed starch, hydrolyzed cellulose, hydrolyzed lignocellulosic biomass, or a combination of two or more thereof. In some embodiments, the present methods include mixing the disaccharides (such as maltose, lactose, and sucrose) and/or the monosaccharides in the water-deficient system.

In some embodiments of any aspect of the present technology, the temperature is about 50° C. to about 160° C. For example, the temperature may be about 70° C. to about 120° C. With respect to the methods of preparing prebiotic oligosaccharides from starch, cellulose or lignocellulosic biomass, the temperature may also be about 100° C. to about 120° C.

The reaction mixtures of the present methods may be mixed for 1 minute to 2 days. For example, the monosaccharides and/or disaccharides and water deficient system may be mixed for 1 minute to 2 days. In some embodiments, the reaction may be mixed for 30 to 120 minutes.

In some embodiments of any aspect of the present technology, the methods include adding a diluting solvent to the mixture comprising prebiotic oligosaccharides to form a diluted mixture in which the metal salt remains substantially in solution. The diluting solvent may be water or methanol or in some cases, ethanol. In some embodiments, the methods further include adding a precipitating solvent (e.g., to the diluted mixture) to selectively precipitate the metal salt or metal salt and unreacted monosaccharides and/or disaccharides over the prebiotic oligosaccharides. The precipitating solvent may be acetone, ethanol, isopropanol, methyl isobutyl ketone or a mixture of any two or more thereof. In the methods of preparing prebiotic oligosaccharides from, the oligosaccharides themselves may be precipitated with suitable precipitating solvents such as a combination of ethanol and acetone.

In some embodiments of any aspect of the present technology, the methods may further include recycling the precipitated metal salt to form another water deficient system. In some embodiments of any aspect of the present technology, the methods may further include purifying the prebiotic oligosaccharides. For example, the purified prebiotic oligosaccharides may contain less than 5% by weight metal salt. In some embodiments, the purified prebiotic oligosaccharides may contain less than 5% by weight HMF and furfural.

BRIEF DESCRIPTION OF THE DRAWINGS

FIG. 2C shows formation of TOS and LGA in ALBTH at 70° C. as a function of reaction time. The batch reaction was conducted using 40% (w/v) initial glucose concentration in 60% LiBr with 40 mM HCl.

FIGS. 11A-11C show MALDI-TOF MS spectra of the oligosaccharide fractions from ALBTH saccharification of poplar at 60% (w/v) loading for 30 min (11A) and 90 min (11B) under mild reaction conditions (T: 110° C. and 120 mM). MS peak assignment is shown in FIG. 11C.

DETAILED DESCRIPTION

Figure 1A:
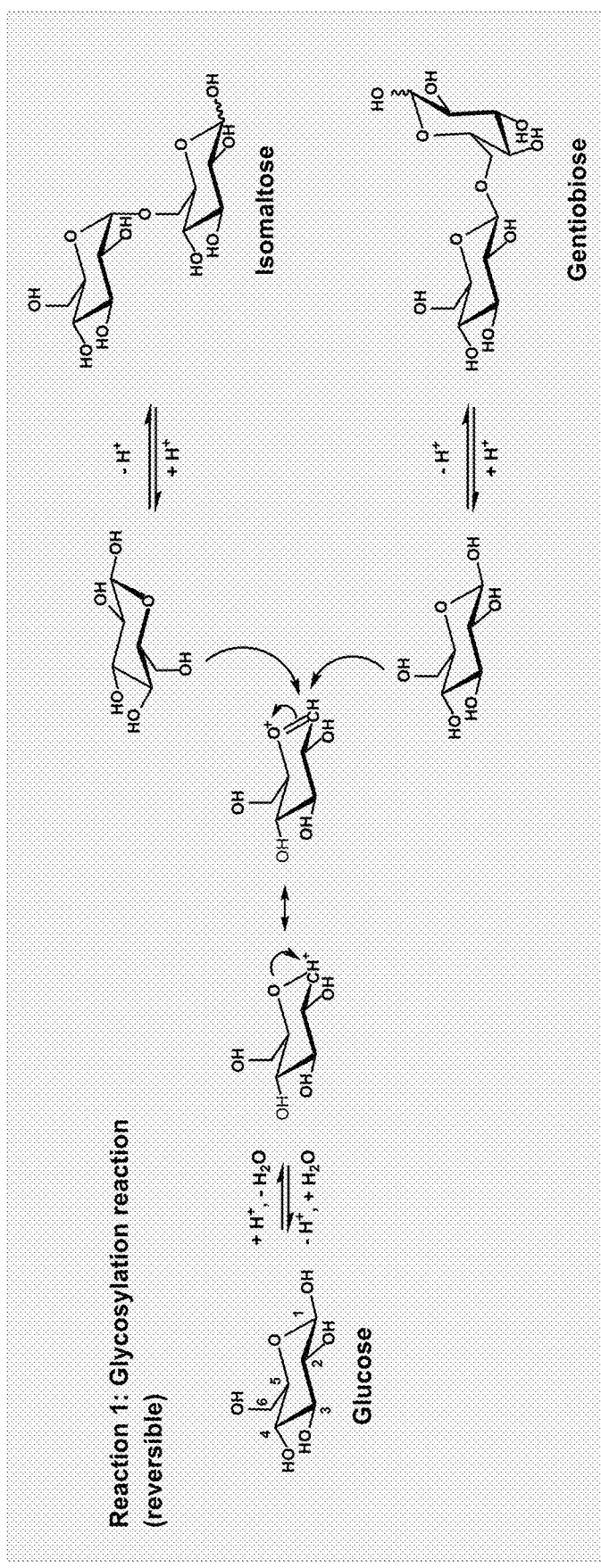
FIGS. 1A-1C shows pathways of acid catalyzed reactions for an illustrative embodiment of the present technology where glucooligosaccharides (GlOS) (FIG. 1A) and levoglucosan (FIG. 1B) are reversibly formed from glucose, and certain sugar degradation by-products (FIG. 1C) are irreversibly formed from glucose.

As noted above, "oligosaccharides" as that term is used herein may have from 2 to 20 monosaccharide residues, joined to each other by glycosidic bonds. The DP refers to the number of monosaccharide residues in the oligosaccharide. Thus, a DP of 2 refers to a disaccharide, whereas a DP of 20 refers to an oligosaccharide having 20 residues. The present technology provides methods of preparing prebiotic oligosaccharides via non-enzymatic glycosylation of monosaccharides, disaccharides, or a combination thereof in a water deficient system containing an alkali or alkali earth metal salt. The present technology also provides methods of preparing such prebiotic oligosaccharides from polysaccharides such as starch, cellulose and lignocellulosic biomass. While the present methods may provide prebiotic oligosaccharides of any length (i.e., a DP of 2, 3, 4, 5, 6, 7, 8, 9, 10, 11, 12, 13, 14, 15, 16, 17, 18, 19, 20 or a range between and including any two of the foregoing values), in some embodiments they have a DP of 2-10 residues. Such oligosaccharides are typically water soluble (i.e., have a solubility >1 mg/mL in water at 25° C.).

In one aspect, the present technology provides a non-enzymatic method for producing oligosaccharides. The method includes mixing one or more types of monosaccharides and/or disaccharides with a water-deficient system at a temperature sufficient to form one or more types of prebiotic oligosaccharides. In the method, the weight ratio of monosaccharides and/or disaccharides to water-deficient system may be 0.01 to about 10; and the water-deficient system includes a metal salt selected from an alkali metal salt and/or an alkaline earth metal salt, water, and a catalytic amount of acid. The molar ratio of water to metal salt in the water-deficient system may be about 2 to about 12; and the acid has a pKa of less than 4.

In another aspect the present technology provides methods of preparing prebiotic oligosaccharides comprising mixing starch, cellulose and/or lignocellulosic biomass with a water-deficient system at a temperature sufficient to form one or more types of prebiotic oligosaccharides that collectively make up at least 25% of the products of the synthesis. Monosaccharides are also produced by the method, but may be minimized in favor of the desired prebiotic oligo saccharides. The weight ratio of starch, cellulosic and/or lignocellulosic biomass to water-deficient system may vary, e.g., from 0.05 to 10. The water-deficient system comprises a metal salt selected from an alkali metal salt and/or an alkaline earth metal salt, water, and a catalytic amount of acid wherein the molar ratio of water to metal salt in the water-deficient system is about 2 to about 12; and the acid has a pKa of less than 4.

The present methods utilize water-deficient systems that are aqueous systems in which the amount of water to salt is very low. The water deficient system is typically an aqueous solution, although a suspension may also be used in some embodiments. The molar ratio of water to metal salt may be as low as 2 or as high as 12. Examples of suitable molar ratios of water to metal salt include about 2, about 3, about 4, about 5, about 6, about 7, about 8, about 9, about 10, about 11, about 12, or a range between and including any two of the foregoing values. For example, the molar ratio of water to metal salt in the water-deficient system may be about 2 to about 5. In some embodiments, the ratio is about 3 at the beginning of the mixing but slowly rises to a higher value as oligosaccharides are formed and water is added to the system as a byproduct of oligosaccharide formation.

A wide variety of monosaccharides and/or disaccharides may be used in the present methods to prepare prebiotic oligosaccharides. For example, one or more monosaccharides may be selected from glucose, fructose, galactose, xylose, mannose, arabinose, rhamnose, hydrolyzed starch, hydrolyzed cellulose, hydrolyzed lignocellulosic biomass, and combinations of two or more thereof. For example, one or more disaccharides may be selected from lactose, isomaltose, maltose, cellobiose, sucrose, and combinations of two or more thereof. By "hydrolyzed starch," "hydrolyzed cellulose" and "hydrolyzed lignocellulosic biomass" is meant a mixture of monosaccharides (or disaccharides and soluble oligosaccharides) comprising 90 wt % or more, respectively, of a starch hydrozylate, cellulose hydrozylate or a lignocellulosic biomass hydrozylate. In some embodiments, the mixture of mono- and/or disaccharides comprise 95 wt %, 96 wt %, 97 wt %, 98 wt % or more of the hydrolyzed mixture. Monosaccharides may be used alone or mixed with the disaccharides and water-deficient system to prepare oligosaccharides. Disaccharides may be used alone or mixed with the monosaccharides and water-deficient system to prepare oligosaccharides.

Surprisingly, extremely high amounts of monosaccharides and/or disaccharides may be added to the water deficient system to help drive the production of oligosaccharides. As shown in the Examples herein, even 1000% (w/v) monosaccharides and/or disaccharides (mass of the monosaccharides and/or disaccharides versus the volume of the water deficient system) may be used in admixture with the water deficient system. Thus, the weight ratio of monosaccharides and/or disaccharides to water deficient system may be 0.01, 0.05, 0.1, 0.25, 0.5, 1, 2, 3, 4, 5, 6, 7, 8, 9, 10, or a range between and including any of the foregoing values. To reach the highest amounts of monosaccharides and/or disaccharides, the monosaccharides and/or disaccharides may be added in a "fed-batch" style. In other words, they are added in two or more portions over time rather than all at once. While not wishing to be bound by theory, it is believed that such high amounts of monosaccharides and/or disaccharides may be dissolved in the water deficient system because as they react to form oligosaccharides, they release water into the system: 1 mole equivalent water for every mole equivalent of monosaccharides and/or disaccharides incorporated into the oligosaccharides. In addition, the water deficient system is assumed to form direct interaction/solvation with the monosaccharides and/or disaccharides and the oligosaccharide products. In practice, the fed-batch operation ensures a complete dissolution/liquefaction of the added monosaccharides and/or disaccharides to form a homogeneous reaction system before next batch of the monosaccharides and/or disaccharides is added. The fed-batch also solves/avoids the mechanical agitation/mixing issue faced when all the monosaccharides and/or disaccharides are added at once.

Methods involving the simultaneous saccharification and glycosylation of polysaccharides such as cellulose, starch or lignocellulosic biomass also permit high loadings of the starting polysaccharides. In some embodiments, the weight ratio may be 0.05, 0.1, 0.25, 0.5, 1, 2, 3, 4, 5, 6, 7, 8, 9, 10, or a range between and including any of the foregoing values.

In the water deficient system of the present technology, the metal salt may be an alkali metal salt or an alkaline earth metal salt. For example, the metal salt may be an alkali halogen salt, or an alkaline earth metal halogen salt, or an alkali thiocyanate salt, or an alkaline earth metal thiocyanate salt. The metal salts may also be, e.g., lithium salts, sodium salts, calcium salts, magnesium salts, or zinc salts. In particular, the metal salts may be one or more of LiBr, LiCl, NaBr, $CaCl_2$, $CaBr_2$, $MgCl_2$, NaI, LiI, $CaI_2$, $MgI_2$, $AlCl_3$, $AlBr_3$, $MgBr_2$, $ZnCl_2$, $ZnBr_2$, $LiCl_4$, $Ca(ClO_4)_2$, LiSCN, and $Ca(SCN)_2$. In some embodiments, the metal salt may be LiBr.

A catalytic amount of acid may be added to speed formation of oligosaccharides in accordance with the present methods. A variety of acids may be used so long as the acid has a pKa of less than 4. For example, the acid may have a pKa of about −10 to less than 4. Thus, useful acids may have pKas of −10, −9, −8, −7, −6, −5, −4, −3, −2, −1, 0, 1, 2, 3, 4 or a range between and including any two of the foregoing values. Acids having pKas in this range include mineral acids such as hydrohalo acids, sulfonic acids, halo acetic acids, and various other carboxylic acids. For example, acids that may be used in the present methods include but are not limited to one or more selected from the group consisting of HCl, $H_2SO_4$, $HNO_3$, $H_3PO_4$, $CH_3SO_3H$, tosylic acid (p-toluene sulfonic acid), oxalic acid, glyoxylic acid, lactic acid, citric acid, formic acid, and trifluoroacetic acid.

The catalytic amount of acid used will vary depending on acid strength. Higher concentrations of weaker acids (e.g., formic) may be needed, whereas lower concentrations of stronger acids (e.g., HCl) may be used. Thus, the water-deficient systems of the present methods may include, e.g., 0.5 mM to 500 mM catalytic acid. Suitable concentrations, may include 0.5 mM, 1 mM, 5 mM, 10 mM, 20 mM, 50 mM, 100 mM, 200 mM, 300 mM, 400 mM, 500 mM, and ranges between and including any two of the foregoing values. For example, the water deficient system may include 1 mM to 200 mM acid.

Various temperatures may be used in the present methods. Because the reaction rate increases with temperature, to avoid overly lengthy reaction times, a temperature of at least about 50° C. is recommended. Temperatures that are too high increase the amount of side reactions and impurities. Hence, a useful temperature range for the present methods is about 50° C. to about 160° C. Suitable temperatures include about 50° C., about 60° C., about 70° C., about 80° C., about 90° C., about 100° C., about 110° C., about 120° C., about 130° C., about 140° C., about 160° C., or a range between and including any two of the foregoing values. For example, the temperature may be about 70° C. to about 120° C.

The time needed for methods of the present technology to produce oligosaccharides varies depending on the concentration of the monosaccharide and/or disaccharides, the strength of the catalytic acid, the concentration of the acid, the temperature of the water deficient system, and the like. For example, at low temperatures (e.g., 50° C.) with weak acids (pKas about 3-4) and modest loadings of monosaccharides and/or disaccharides, the mixture may take up to 2 days to produce the equilibrium amounts of oligosaccharides. At high temperatures (e.g., 160° C.) with stronger acids (e.g., HCl) and more monosaccharides and/or disaccharides, the mixture may only need mixing for 1 minute to provide the equilibrium amount of oligosaccharides. Examples of suitable time periods for mixing the monosaccharides and/disaccharides and water deficient system include 1, 2, 3, 4, 5, 10, 15, 20, 25, 30, 40, or 50 minutes, 1, 1.5, 2, 3, 4, 5, 6, 8, 10, 12, 15, or 20 hours, 1, 1.5 or 2 days, or a range between and including any two of the foregoing values. For example, the time may range from 1 minute to 2 days, 5 minutes to 20 hours, 5 minutes to 2 hours, and the like.

Once the mixture comprising the oligosaccharides has reached completion (i.e., equilibrium), it may be quenched or otherwise terminated. Thus, the present methods may also include adding a diluting solvent to the mixture comprising prebiotic oligosaccharides to form a diluted mixture in which the metal salt remains substantially in solution. By "substantially in solution" is meant that at least 85 wt % of the metal salt remains in solution and does not precipitate. In some such embodiments at least 90 wt %, at least 95 wt %, or at least 98 wt % of the metal salt remains in solution, and in others, all of the metal salt remains in solution. Any solvent that does not precipitate the metal salts may be used, and preferably one that permits ready recovery of the salts. Hence, methanol, aqueous methanol, aqueous acetone or even water could be used as the diluting solvent. Optionally, the reaction mixture may be cooled before or during dilution. For example, the reaction vessel may be plunged into a cooling bath or diluting solvent having a temperature below the reaction temperature may be used.

Following dilution of the mixture including oligosaccharides, a precipitating solvent (also known as an anti-solvent) may be added to the diluted mixture to selectively precipitate the metal salt or metal salt and unreacted monosaccharides and/or disaccharides over the prebiotic oligosaccharides. Acetone may be used as the precipitating solvent, although ethanol, isopropanol, methyl isobutyl ketone (MIBK) or mixtures of any two or more thereof may be used in some cases. The precipitated metal salt may be recycled to form another water deficient system. The solution containing the prebiotic oligosaccharides may be further purified by one or more additional rounds of dilution and precipitation or by other methods known in the art (e.g., chromatography). The diluting and precipitating solvents may be recovered, e.g., by distillation.

The present methods provide prebiotic oligosaccharides with reduced levels of both metal salts and impurities such as, but not limited to, levoglucosan, formic acid, furfural and hydroxymethyl furfural (HMF). For example, the prebiotic oligosaccharides may have less than 10 wt %, less than 7 wt %, less than 5 wt %, less than 3 wt %, less than 2 wt % or less than 1 wt % impurities. In some embodiments of methods of the present technology, the purified prebiotic oligosaccharides contain less than 5 wt %, less than 4 wt %, less than 3 wt %, less than 2 wt %, less than 1 wt % or less than 0.5 wt % metal salt or a range between and including any two of the foregoing values. In others, the purified prebiotic oligosaccharides contain less than 5 wt %, less than 4 wt %, less than 3 wt %, less than 2 wt %, less than 1 wt % or less than 0.2 wt % HMF and furfural.

In another aspect, the present technology provides compositions comprising one or more prebiotic oligosaccharides prepared according to any of the methods described herein. For example, in some embodiments, the compositions are nutraceutical compositions and comprise food, drink or other edible component such as herbs, spices, flavorings, or a probiotic-containing edible (e.g., yogurt). In some embodiments, the compositions include one or more prebiotic oligosaccharides prepared according to any of the methods described herein and a pharmaceutical active ingredient and/or a pharmaceutically acceptable excipient.

EXAMPLES

Materials

D-Glucose (99%), levoglucosan (99%), levulinic acid (98%), phosphoric acid (85 wt %), and aminopyrazine (98%) were purchased from Acros Organics (Pittsburgh, Pa.). D-Gentiobiose (98%), lithium bromide (99%), formic acid (97%), oxalic acid (98%), and 5-hydroxymethyl-2-furaldehyde (HMF, 98%) were purchased from Alfa Aesar (Tewksbury, Mass.). D-Maltose (94%), isomaltose (97%), lactose (99%), sucrose (99%), acetone (99.5%), acetonitrile (HPLC grade), and acetic acid (99.8%) were purchased from Fisher Scientific (Pittsburgh, Pa.). Methanol (99.8%), ethyl alcohol (anhydride), sodium hydroxide (50%), hydrochloric acid (37%), sulfuric acid (98%), and citric acid (99%) were purchased from VWR (Radnor, Pa.). p-Toluenesulfonic acid monohydrate (TsOH, 98.5%), dichloroacetic acid (DCA, 99%), 2,5-hydroxybenzoic acid (DHB, 98%), and deuterium oxide ($D_2O$, 99.9 atom % D with 1% 3-(trimethylsilyl)-1-propanesulfonic acid, DSS), and microcrystalline cellulose (Avicel PH-101, average particle size: ~50 μm) were purchased from Sigma Aldrich (St. Louis, Mo.). All the chemicals were used as received without further purification.

Poplar NE222 (harvested in Rhinlander, Wis.) chips were ground using a Wiley mill, and the particles between 20 and 100 mesh were collected as raw material for the present study. Chemical compositions of the poplar were insoluble lignin 21.4±0.2%, soluble lignin 6.0±0.1%, glucan 46.9±0.0%, arabinan 0.3±0.0%, galactan 0.6±0.0%, xylan 14.5±0.0%, and mannan 0.5±0.0%, and 95% ethanol extractives 1.8±0.1%.

General Procedure A: Batch Sugar Glycosylation Reaction

Sugar glycosylation reaction was conducted in acidic LiBr solution in a 40-mL glass reactor heated in an oil bath under atmospheric pressure. Glucose was mixed with 5 mL of acidic LiBr solution using a Teflon-coated magnetic stirring bar, and the mixture was heated up to a preset temperature within 2 min and maintained at the temperature for preset period of time. At the preset time, the reaction was quenched by immersing the glass reactor in ice water, and then the mixture was diluted with methanol.

General Procedure B: Separation and Recovery of GlOSs and LiBr

The glucose oligosaccharides (GlOSs) produced from the glycosylation reaction were separated and recovered by precipitation in an anti-solvent (acetone). In brief, after the glycosylation reaction, methanol (equivalent to 2-15 times of the volume of the reaction mixture) was added to dilute the syrup-like reaction mixture, and the diluted mixture was transferred dropwise to 300 mL acetone in a centrifuge bottle immersed in ice water and vigorous stirred to precipitate the GlOSs. The precipitate was collected by centrifugation at 4500 rpm for 20 min and freeze-dried. The resultant colorless crystal of GlOSs was collected for subsequent characterization.

The supernatant was transferred to a single neck flask, and the volatile solvents (acetone and methanol) were removed using a rotary evaporator under reduced pressure (e.g., 10-30 kPa) at 60° C. The residual LiBr solution was used for the next batch reaction. Residual methanol and acetone in LiBr solution were quantitated using a gas chromatography (GC-2014, Shimadzu, Md.) with a flame ionization detector (FID) and a 30 m×0.32 mm×0.5 μm ZB-Wax Plus column. The oven temperature was kept at 100° C. for 5 min and gradually increased to 180° C. in 20 min. LiBr concentration was analyzed using Mohr's titration method.[25]

General Procedure C: Probiotic Growth on the GlOSs Synthesized from Glucose Glycosylation Lactic acid bacteria (LAB) from human intestine including *Lactobacillus reuteri* (ATCC 6475), *Lactobacillus rhamnosus* GG, *Lactobacillus casei* BFLM 218, *Lactobacillus gasseri* ATCC 33323 were kindly provided by the lab of Dr. Pijkeren; and *Lactobacillus buchneri* (ATCC 4005) and *Bifidobacterium bifidum* (ATCC 29521) and *Bifidobacterium animalis* (DSM 10140) were generously provided by USDA ARS culture collection (NRRL) for in vitro fermentation experiments. The strains were reactivated at 37° C. under anaerobic conditions on MRS medium (ATCC medium 416) for *Lactobacillus* and on Reinforcement Clostridial Medium for *Bifidobacteria* (ATCC medium 2107).

Fermentability of the GlOSs by the probiotic strains was evaluated in Hungate tubes at 37° C. The modified MRS fermentation broth and Reinforcement Clostridial Medium fermentation broth were reconstituted without glucose, as described below. Modified MRS medium for LAB stains: dissolving peptone (1.0 g), beef extractive (1.0 g), yeast extractive (0.5 g), NaCl (0.4 g), dipotassium phosphate (0.4 g), ammonium citrate (0.4 g), manganese sulfate (0.01 g), magnesium sulfate (0.02 g), Tween 80 (0.2 g), and L-cysteine-HCl (0.1 g) in 200 mL deionized (DI) water with pH 6.8 in anaerobic condition; and modified Reinforcement Clostridial broth (pre-reduced) for *Bifidobacteria*: dissolving peptone (1.0 g), beef extractive (1.0 g), yeast extractive (0.5 g), dipotassium phosphate (0.4 g), sodium chloride (0.4 g), ammonium citrate (0.4 g), manganese sulfate (0.01 g), magnesium sulfate (0.02 g), ferrous sulfate (0.002 g), Tween 80 (0.2 g), resazurin (0.0002 g), and L-cysteine-HCl (0.1 g) in 200 mL DI water with pH 6.8 in anaerobic condition. Filter-sterilized GlOSs solution and glucose solution as positive control were mixed with the fermentation broth at a sugar concentration of 10 g/L. The pre-cultured cells were washed twice with PBS (phosphate-buffered saline) buffer, and a cell suspension of approximately O.D.=0.1 was inoculated anaerobically for 24-48 h. Sample medium without inoculation was used as negative control. Growth was monitored by the changes in optical density at 600 nm (OD) from duplicated fermentation experiments.

General Procedure D: Chromatographic Quantitation of Saccharides

Consumption of carbohydrate substrates and production of short-chain fatty acid (SCFA) in the fermentation broths after 24-48 h growth at 37° C. was quantitated by chromatographic methods, as follows. Glucose, disaccharides (isomaltose and gentiobiose), and levoglucosan were quantitated using a high performance anion exchange chromatography (HPAEC) on an ICS-3000 system (Dionex, Sunnyvale, Calif.) equipped with a pulsed amperometric detector and a 250 mm×4 mm CarboPac PA1 column (Thermo Scientific, Sunnyvale, Calif.) at 30° C. A gradient eluent containing A: deionized water (18 MΩ) and B: 100 mM NaOH was programmed as 0-40 min, 80% A and 20% B; 40.1-49 min, 30% A and 70% B; and 49.1-58 min, 80% A and 20% B. An isocratic post-column eluent of 0.5 M NaOH was used at a flow rate of 0.3 mL/min to ensure the baseline stability and to enhance the detector sensitivity.

General Procedure E: Quantitation of GlOSs

Total GlOSs were quantitated following a post-hydrolysis procedure to convert all the GlOSs (DP>1) to monosaccharides. Briefly, the syrup mixture after the glycosylation reaction was diluted with 4% sulfuric acid (to sugar concentration ≤5 g/L) and hydrolyzed at 121° C. for 1 h in an autoclave unit. After neutralization, the total monosaccharides in the hydrolysate were quantitated using the HPAEC method described above. The quantity of GlOSs was calculated as the difference of the monosaccharides before and after the post-hydrolysis after subtracting levoglucosan, using equation 1.

GlOSs=Total glucose (after post hydrolysis)−Glucose (before post hydrolysis)−Levoglucosan   (Eq. 1)

General Procedure F: Quantitation of Sugar Degradation Products and SCFA

The sugar degradation products including formic acid, levulinic acid, 5-hydroxymethyl furfural (HMF) and SCFA (acetic acid, propionic acid, and butyric acid) were quantitated using a high performance liquid chromatography (HPLC) on an ICS-3000 system (Dionex, Sunnyvale, Calif.) equipped with a 300 mm×7.8 mm C-610H column (Supelco, Bellefonte, Pa.) at 30° C. and a UV detector at 210 nm. An isocratic flow of 0.1% phosphoric acid was applied as the mobile phase at 0.6 mL/min.

General Procedures G1, G2, and G3: Characterization of GlOSs

Procedure G1: MALDI Analysis.

MALDI-TOF MS analysis was performed in a positive ionization mode using an AB Sciex 4800 MALDI TOF/TOF mass spectrometer (Foster City, Calif.) equipped with Nd:YAG 200 Hz laser at 355 nm. To attenuate the background signals, in particular those below m/z 500, a binary matrix mixture was applied. The matrix containing aminopyranize (AP, 2.5 mg/mL) with 2,5 dihydroxybenzoic acid (DHB, 7.5 mg/mL) in acetonitrile was combined with an equal volume of a GlOS sample (2 mg/mL) and then placed on a stainless steel target. After air-drying, the sample spot was exposed to an accumulation of one thousand laser shots to acquire a MS spectrum.

Procedure G2: Gel Permeation Chromatographs (GPC) Analysis.

The degree of polymerization of GlOS was estimated using GPC after derivatizing the hydroxyl groups of the GlOS with phenylisocyanate to form GlOS tricarbanilates. First, 30 mg GlOS was dried in a Duran bottle (100 mL) in a vacuum oven at 50° C. for 12 h. Then anhydrous pyridine (6 mL) and phenyl isocyanate (2 mL) were added. The bottle was sealed with a screw thread cap with a PTFE faced silicone liner, and the mixture was reacted in an incubating shaker at 70° C. and 80 rpm for 48 h. The derivatization reaction was quenched by adding methanol (5 mL) and then cooling in an ice bath. The mixture was transferred dropwise to a mixture of methanol/water (35 mL, 7/3, v/v) and glacial acetic acid (1 mL). The precipitates of GlOS derivatives were collected by centrifugation at 8000 rpm, washed twice with the methanol/water mixture, and then vacuum-dried at 50° C.

Procedure G3: NMR Analysis.

The glycosidic linkages of the GlOSs from the glucose glycosylation reaction were identified using NMR. The GlOSs were dissolved in $D_2O$ with 1% DSS as a reference. $^1H$-$^{13}C$ heteronuclear single quantum correlation (HSQC) spectra were recorded on a Brucker AVANCE 500 MHz instrument (Bilerica, Mass.) equipped with a cryoprobe. Bruker pulse program "hsqcetgpsisp 2.2 (adiabatic-pulse fashion)" was used with spectral widths of 10 ppm (from 9 to −1 ppm) and 160 ppm (from 155 to −5 ppm) for the $^1H$ and $^{13}C$ dimensions, respectively. The acquisition time for $^1H$ and $^{13}C$ was 200 ms and 8 ms, respectively, with the relaxation delay of 1-10 s. The spectra were processed using Topspin 3.2 software with a final 2D data matrix size of 1024×1024 data points. For the region- and stereo-selectivity estimation, the anomeric contours of α/β-1,1-, α/β-1,2-, α/β-1,3-, α-1,4-, α/β1,6-glycosidic linkages were used due to the similar C—H environments and distinguishable chemical shifts. The anomeric integral of α/β-1,1-glycosidic linkages were logically halved.

General Procedure H: Biomass Saccharification in ALBTH

Saccharification was conducted in 40 mL glass vials with pressure-relief screw tops. In a batch process, poplar powder or microcrystalline cellulose was directly mixed with acidic lithium bromide trihydrate solution with acid as catalyst. The mixture was stirred or sonicated (in case of high solid loading) at ambient temperature for 5 min, before putting the vial into an aluminum block heated in an oil bath. In a fed-batch operation, fresh poplar power or microcrystalline cellulose was added successively when previously loaded biomass was liquefied with the aim to increase the total solid loading. At pre-set time, the reaction was quenched by immersing the reaction vial in ice water and diluting the mixture with DI water. Insoluble residues (IR) were collected by filtration using a pre-weighted filtering crucible (30 mL, low form with medium porosity), washed thoroughly with water, and then gravimetrically quantitated. The resultant supernatant was analyzed for quantitating monosaccharides, disaccharides, oligosaccharides, and sugar degradation products, as described below.

Yield of oligosaccharides (gluco-oligosaccharides (GlOSs) and xylo-oligosaccharides (XOSs)) were quantitated following a post-hydrolysis procedure to convert all the oligosaccharides to monosaccharides. Briefly, the sample of the hydrolysate (the supernatant above) was diluted with 4% sulfuric acid to a sugar concentration ≤5 g/L and hydrolyzed at 121° C. for 1 h in an autoclave unit. The total monosaccharides in the hydrolysate were quantitated using a high performance anion exchange chromatography (HPAEC) method described below. The yield of oligosaccharides was calculated from the difference in monosaccharides and/or disaccharides before and after the post-hydrolysis.

General Procedure I: Chromatographic Quantitation of Saccharides

Monosaccharides (arabinose, galactose, glucose, xylose, and mannose) and/or disaccharides (lactose and sucrose) and cellobiose were quantitated using the HPAEC on an ICS-3000 system (Dionex, Sunnyvale, Calif.) equipped with a pulsed amperometric detector and a 250 mm×4 mm CarboPac PA1 column (Thermo Scientific, Sunnyvale, Calif.) at 30° C. A gradient eluent containing A: deionized water (18 MΩ·cm) and B: 100 mM NaOH was programmed as 0-40 min, 80% A and 20% B; 40.1-49 min, 30% A and 70% B; and 49.1-58 min, 80% A and 20% B. An isocratic post-column eluent of 0.5 M NaOH was used at a flow rate of 0.3 mL/min to ensure the baseline stability and to enhance the detector sensitivity.[12]

General Procedure J: Chromatographic Quantitation of Sugar Degradation Products

Sugar degradation products including formic acid, levulinic acid, 5-hydroxymethyl furfural (HMF) and furfural were quantitated using a high performance liquid chromatography (HPLC) on an ICS-3000 system (Dionex, Sunnyvale, Calif.) equipped with a 300 mm×7.8 mm C-610H column (Supelco, Bellefonte, Pa.) at 30° C. and a UV detector at 210 nm. An isocratic flow of 0.1% phosphoric acid was applied as the mobile phase at 0.6 mL/min.[12]

General Procedure K: Calculation Equations

IR (wt %)=Mass of insoluble residues/Mass of starting biomass×100%

Product yield (%)=Product mass×Conversion factor/Mass of starting biomass×100%

Conversion factors for glucose, xylose, cellobiose, isomaltose, gentiobiose, HMF, and furfural are 0.90, 0.88, 0.95, 0.95, 0.95, 1.29, and 1.38, respectively.

GlOS/XOS (%)=Total monosaccharides (after post-hydrolysis)−Monosaccharide yield−Levoglucosan yield (only for glucose)

General Procedure L: MALDI TOF MS Analysis

The MS spectra of the oligosaccharides were collected on an AB Sciex 4800 MALDI TOF/TOF mass spectrometer (Foster City, Calif.) equipped with Nd: YAG_200 Hz laser at 355 nm. A binary matrix was used to attenuate the background signals, in particular those below m/z 500.[13] The matrix containing aminopyranize (AP, 2.5 mg/mL) with 2,5 dihydroxybenzoic acid (DHB, 7.5 mg/mL) in acetonitrile was combined with an equal volume of an oligosaccharide sample (2 mg/mL) and then placed on a stainless steel target. After air-drying, the sample spot was exposed to an accumulation of one thousand laser shots for MS spectrum.

General Procedure M: GPC Analysis

GPC analysis was carried out on a Dionex ICS-3000 system (Dionex, Sunnyvale, Calif.) equipped with three tandem 300 mm×7.8 mm (1×i.d.) Phenogel 5U columns (10000, 500, and 50 Å, respectively) and a 50 mm×7.8 mm (1×i.d.) Phenogel 5U guard column (Phenomenex, Torrance, Calif.). The eluent was an isocratic 100% THF (HPLC grade without stabilizer) at a flow rate of 1.0 mL/min, and the column temperature was kept at 30° C. The derivatized GlOS (10 mg/mL in THF) was injected after passing through a 0.45 μm syringe filter and detected with a variable wavelength detector (VWD) at 270 nm. The apparent weight average molecular weight ($M_w$) was calibrated using polystyrene standards. The weight average degree of polymerization (DP) of the GlOS was calculated using Equation 3:

$$DP=M_w/519 \quad (3)$$

where 519 g/mol represents the molecular weight of the repeating unit of the derivatized GlOS.

General Procedure N: NMR Analysis of Cellulose and Lignocellulose-Derived OS

The glycosidic linkages of the oligosaccharides from the glycosylation reaction were identified using nuclear magnetic resonance (NMR) spectroscopy. The oligosaccharides from poplar and cellulose were dissolved in $D_2O$ with 1 wt % DSS as a reference. $^1H$-$^{13}C$ heteronuclear single quantum correlation (HSQC) spectra were recorded on a Brucker AVANCE 500 MHz instrument (Bilerica, Mass.) equipped with a DCH cryoprobe. Bruker pulse program "hsqcetgpsisp 2.2 (adiabatic-pulse fashion)" was used with spectral widths of 10 ppm (from 9 to −1 ppm) and 160 ppm (from −5 to 155 ppm) for the $^1H$ and $^{13}C$ dimensions, respectively. The acquisition time for $^1H$ and $^{13}C$ was 200 ms and 8 ms, respectively, with the relaxation delay of 1-10 s. The spectra were processed using Topspin 3.2 software with a final 2D data matrix size of 2048×1024 data points.

Example 1: Process Description and Expected Reactions of Glucose in ALBTH

In an illustrative embodiment of the present methods, GlOSs were directly produced from glucose via General Procedure A. As briefly summarized in FIG. 1A, the feedstock is glucose, and concentrated LiBr aqueous solution with small amount of acid as catalyst is the reaction medium. After the glycosylation, the reaction mixture containing GlOSs and unconverted glucose was first diluted with methanol to reduce viscosity and then dropwise added in acetone to precipitate the GlOSs. The GlOSs were collected by filtration or centrifugation. The supernatant, containing the majority of the unconverted glucose, a small amount of the unprecipitated GlOSs, and LiBr, was evaporated under vacuum to recover the organic solvents (methanol and acetone). The recovered LiBr solution could be directly reused for next batch reaction, in spite of containing a small amount of residual glucose and oligosaccharides. The methanol and acetone fraction could be separated and recycled after distillation. The crude GlOSs contained a small amount of co-precipitated glucose and LiBr and could be further purified by repeating operations of dissolution in methanol and precipitation in acetone.

Figure 1B:
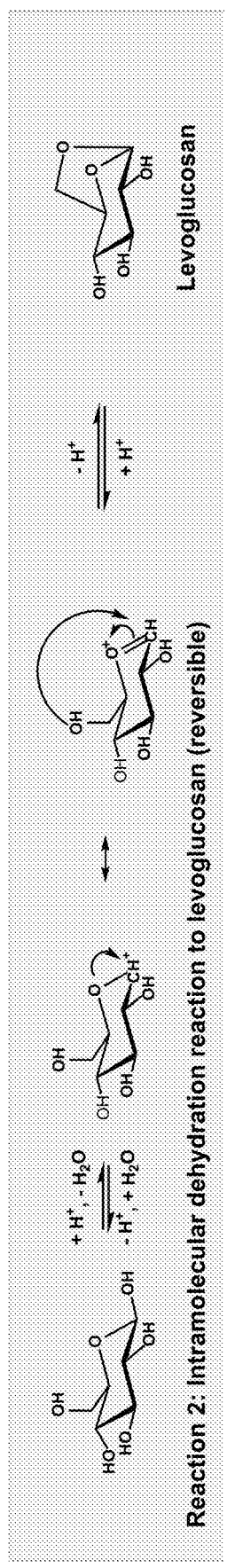

It is generally accepted that the acid catalyzed glycosylation reaction (reversion reaction) of glucose, analogous to the Fischer glycosylation reaction, forms new glycosidic bonds via a $S_N1$ mechanism (FIG. 1B). It is initiated from the protonation of C1 hydroxyl group, followed by subsequent loss of a water molecule, resulting in a C1 carbocation intermediate. The intermediate is partially stabilized by the oxocarbenium resonance structure. A subsequent nucleophilic attack by the hydroxyl group of an adjacent glucose molecule forms a new glycosidic bond after proton transfer. In this process, glucose acts as both the glycosyl donor (C1 anomeric carbon of a glucose molecule) and the glycosyl acceptor (C1, C2, C3, C4, and C6 hydroxyl groups of other glucose molecules). The resultant disaccharide contains one glycosyl donor site and eight potential glycosyl acceptor sites, all of which can participate in subsequent glycosylation reaction to form longer oligosaccharides. Notably, the glycosylation is virtually the reverse reaction of hydrolysis. The glycosidic bonds newly formed from the glycosylation reaction could be potentially cleaved by acid under certain conditions. The yield of GlOS is dependent on the competition between the glycosylation and the hydrolysis reactions in the system.

Figure 1C:
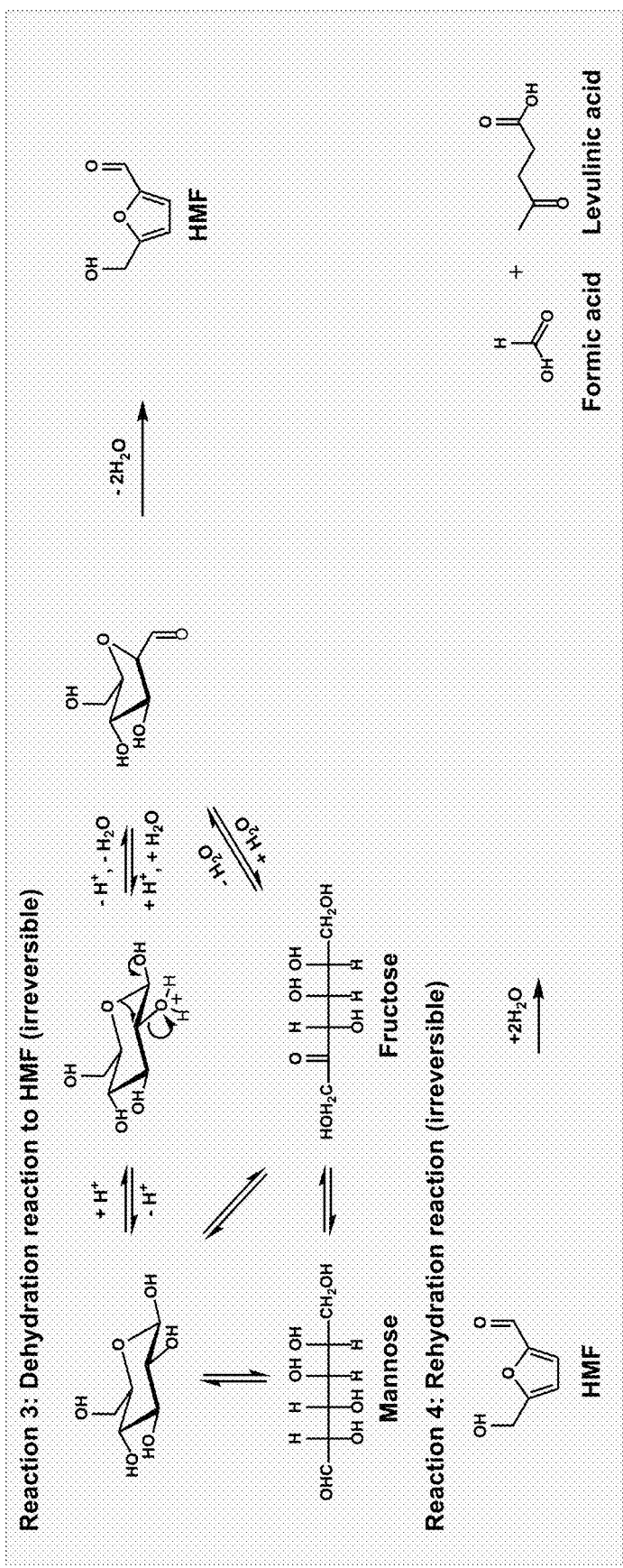

Besides the hydrolysis and glycosylation reactions, glucose under acidic conditions is prone to intramolecular dehydration, as shown in FIG. 1C. The C1 carbocation intermediate from glucose is vulnerable to a nucleophilic attack by the C6 hydroxyl group of the same molecule, forming anhydroglucose. This intramolecular condensation reaction yields 1,6-anhydro-β-D-glucopyranose (LGA) and 1,6-anhydro-β-D-glucofuranose (AGF), depending on the ratio of the pyranose and furanose conformation in the media. Since formation of D-glucofuranose is barely significant in aqueous solution, only LGA was taken into consideration as the intramolecular dehydration product in this study. It is also worth noting that LGA can be reversibly hydrolyzed back to glucose. Instead of protonating C1 anomeric hydroxyl group to generate the reactive C1 carbocation, the acid enables protonation of C2 hydroxyl group as well, which leads to transformation of the pyranose ring to the furan aldehyde intermediate with a C2-O5 bond. Further dehydration of this intermediate irreversibly yields HMF. In aqueous media, HMF lacks stability and further rehydrated irreversibly to levulinic and formic acids. In addition, the isomerization of glucose to fructose was observed in the LiBr system, in which both $Li^+$ and $Br^-$ catalyzed the isomerization via different pathways. Fructose is also accepted as a crucial intermediate to form HMF.

Example 2: Process Optimization to Enhance GlOS Yield from Glucose

Because glycosidic bonds are readily hydrolyzed, it is difficult to form glycosidic bonds between two monosaccharides in a water-rich solution. Under acidic conditions, the yield of oligosaccharides from glucose and xylose via glycosylation in previous work has barely exceeded 20%. Because the glycosylation reaction releases water, it is thermodynamically unfavorable in an aqueous solution. In addition, there is a competition between water molecules and sugar hydroxyls as the nucleophilic acceptors to react with the protonated C1 anomeric carbons.

Example 2.1: Temperature

Figure 2A:
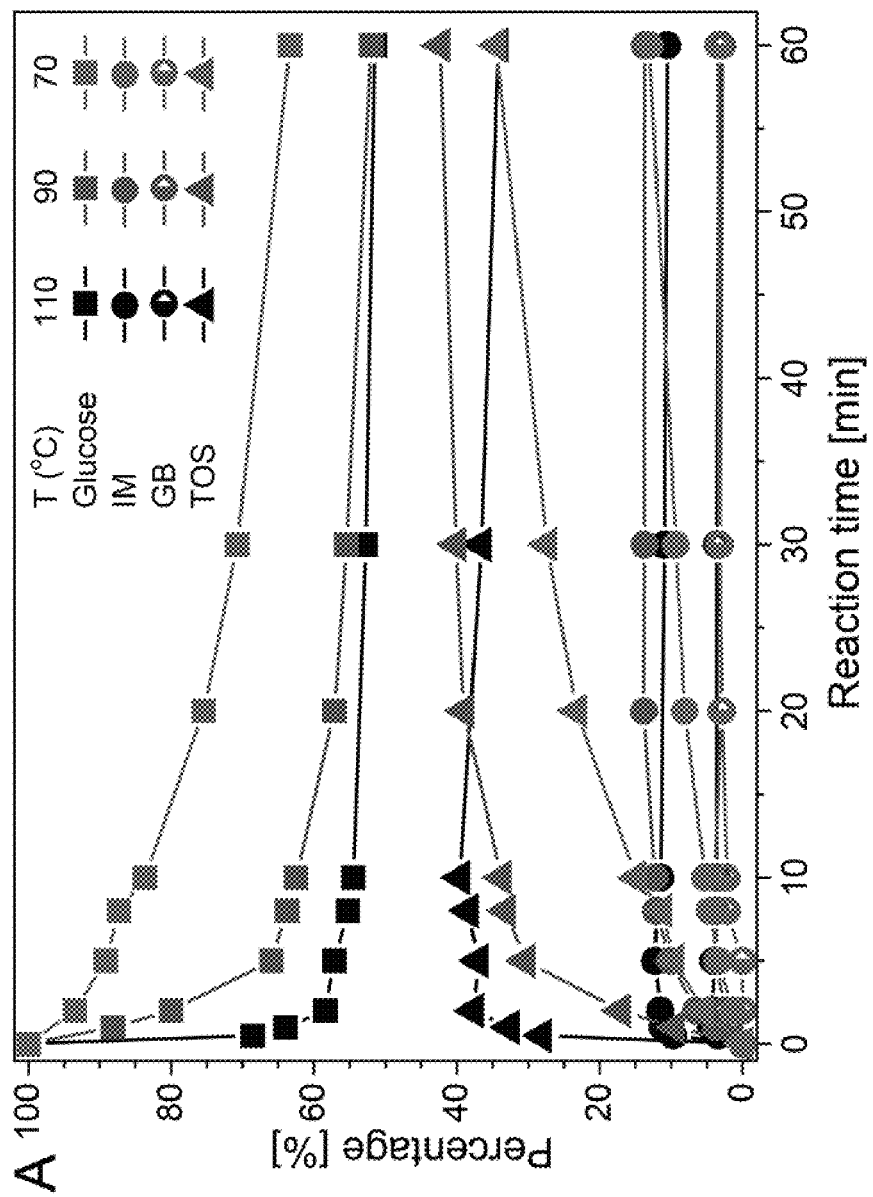
FIGS. 2A-2C show the formation of oligosaccharides/depletion of glucose (2A) and degradation products (2B) as a function of reaction time for the illustrative embodiment mixing glucose in ALBTH (i.e., glycosylation) at different temperatures. The glycosylation reaction was conducted with 40% (w/v) initial glucose concentration in 60% LiBr containing 40 mM HCl. Total oligosaccharides (TOS), isomaltose (IM), gentiobiose (GB), levoglucosan (LGA), hydroxymethylfurfural (HMF), levulinic acid (LA), and formic acid (FA) denote total oligosaccharides, isomaltose, gentiobiose, levoglucosan, hydroxymethylfurfural, levulinic acid, and formic acid, respectively.
Figure 2B:
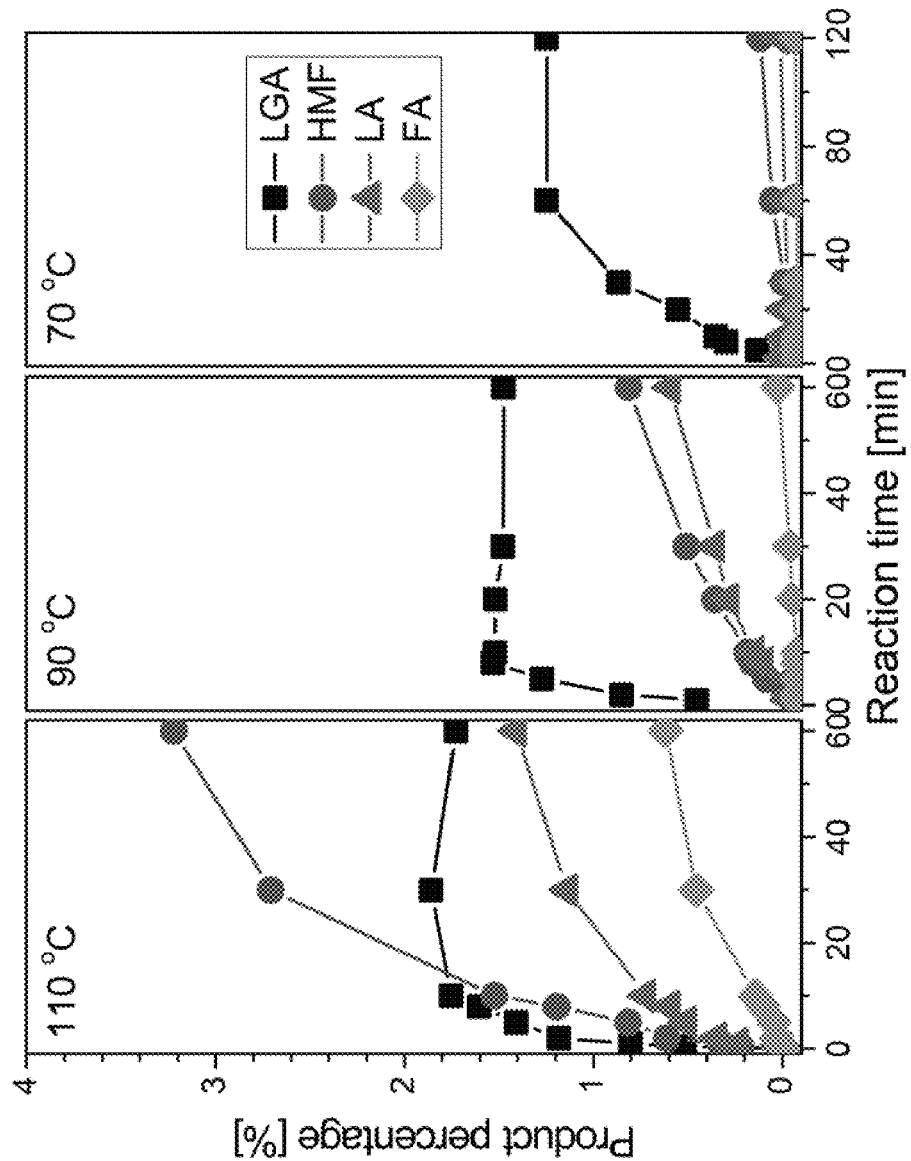

The consumption of glucose and yield of oligosaccharides in acidic lithium bromide trihydrate (ALBTH) at varied reaction temperatures were plotted as a function of reaction time in FIG. 2A. The glycosylation of glucose in ALBTH in accordance with General Procedure A was fast at 110° C. Over 41.6% of glucose was consumed in 2 min, accompanied with the formation of 37.7% oligosaccharides. Production of the oligosaccharides reached a plateau at a yield of 39.5% after 10 min when 45.5% of glucose was converted. Glucose conversion increased slightly after 10 min, but did not provide additional oligosaccharides, suggesting that the glycosylation forming new glycosidic bonds and the hydrolysis cleaving glycosidic bonds had reached equilibrium. As expected, more sugar degradation products were generated with extended reaction duration (FIG. 2B). For instance, the yield of HMF and organic acids (levulinic and formic acids) increased from 1.5 and 0.9% at 10 min to 3.2 and 2.0% at 60 min, respectively.

Figure 2C:
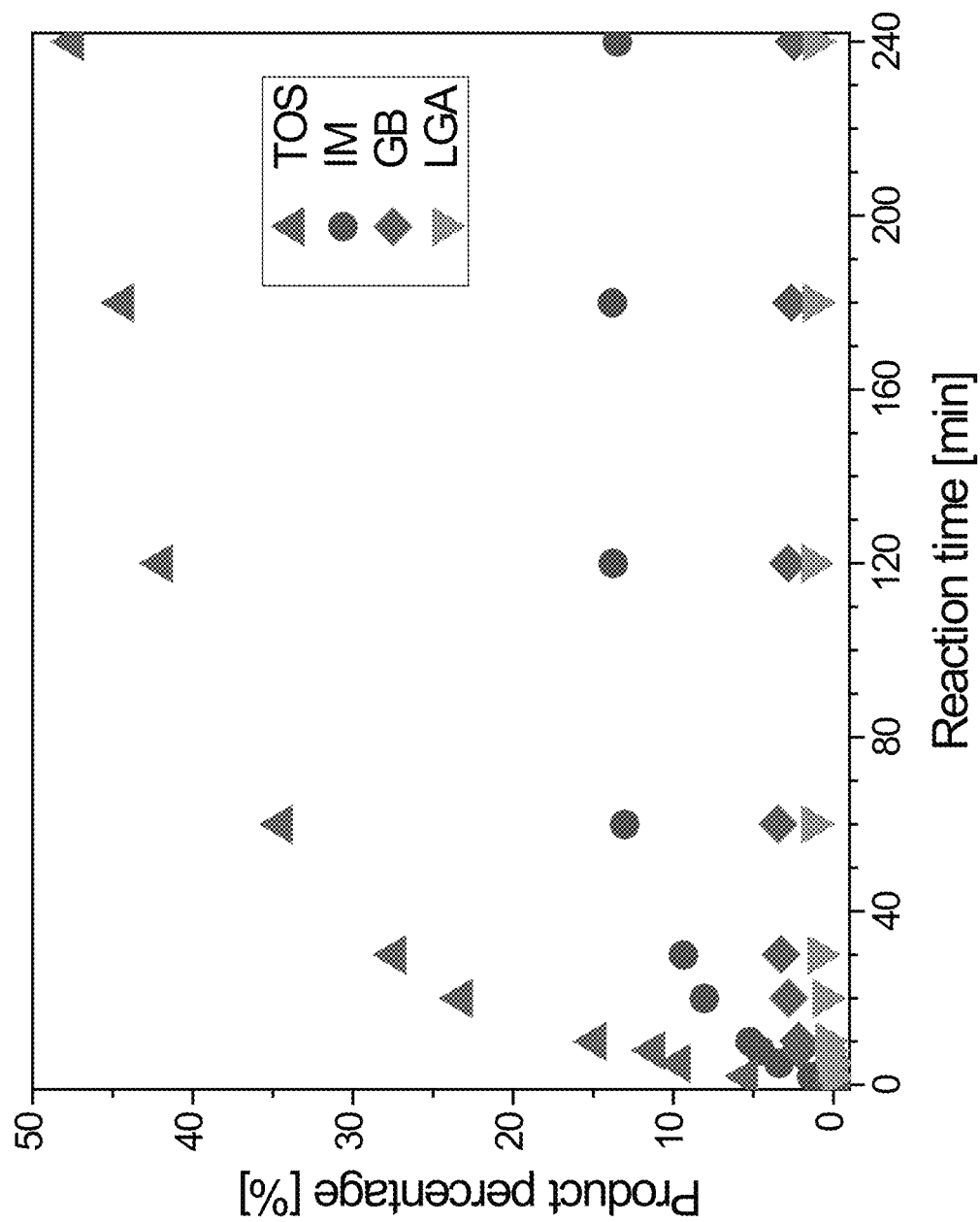

Lowering the reaction temperature from 110° C. to 70° C., the turnover frequency of glucose in ALBTH decreased significantly from 20.0 $min^{-1}$ to 1.8 $min^{-1}$. The formation of GlOSs was slow at low temperature, but the maximum yield of GlOSs was higher, for example, reaching 42.3% at 90° C. at 60 min and 47.5% at 70° C. at 240 min (FIGS. 2A and 2C]). These observations suggest that longer reaction times at lower temperatures favored the glycosylation reaction because glucose degradation was suppressed. As shown in FIG. 2B, only approximately 0.9 and 0.1% glucose was dehydrated to HMF in ALBTH after 60-min reaction at 90° C. and 70° C., respectively. Formation of levulinic acid and formic acid was even not detected at 70° C. Therefore, it appears that lower temperatures may minimize the formation of sugar degradation products, thus reducing the downstream cost for product purification and detoxification. However, reaction times can be considerably lengthened at lower temperatures. For example, the conversion of glucose hardly exceeded 25% at 50° C., even though the reaction was extended to over 12 h (data not shown).

It was found that isomaltose (α-1,6 linked) and gentiobiose (β-1,6 linked) were the most abundant disaccharide products of the glucose glycosylation in ALBTH. For example, the maximal yields of isomaltose and gentiobiose were 12.2 and 4.1% (110° C.) and 13.8 and 2.7% (70° C.), respectively. This is because the primary hydroxyl (C6-OH) was a more reactive glycosyl acceptor than the secondary hydroxyls (C2-OH, C3-OH, and C4-OH) and the hemiacetal hydroxyl (C1-OH). In addition, the presence of the methylene group on C6-OH reduces the steric hindrance of $S_N1$ substitution between the two bulky sugar rings. Similar observation was reported during the glucose glycosylation catalyzed by glycosidases or dilute $H_2SO_4$. Formation of α-glycosidic bonds (axial orientation) were more favorable than formation of β-glycosidic bonds (equatorial orientation) due to the anomeric effect. Even though the $sp^2$ hybridized anomeric carbon (C1) does not have a preference to the nucleophilic attacks by the glycosyl donors from either the top (β-glycoside) or the bottom (α-glycoside), the α-products were thermodynamically preferred because of electron repulsive interaction and hyperconjugation effect. As shown in FIG. 2, gentiobiose reached the maximal yield earlier than isomaltose, indicating that the formation of β-glycosidic bonds was kinetically controlled. Therefore, decreasing reaction temperature (slowing down the reaction rate) could improve the stereo-selectivity. For example, the α/β product ratio increased from 3.0 at 110° C. to 5.5 at 70° C. The stereo-selectivity of glycosylation in ALBTH was approximately 3.9 times higher than that in dilute sulfuric acid.[19, 20]

Example 2.2: Initial Glucose Concentration

Figure 3A:
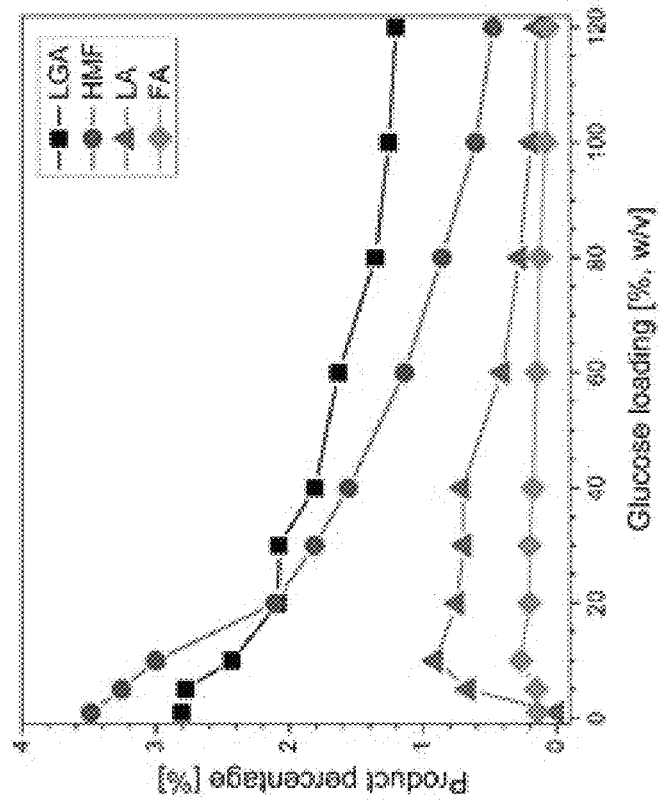
FIGS. 3A-3F show the effects of various parameters on depletion of glucose and production of oligosaccharides and degradation products according to an illustrative embodiment of the present technology. The graphs show the effects on glucose depletion and yields of IM, TOS, LGA, HMF, LA and FA due to glucose (reactant) concentration (FIGS. 3A, 3B), water concentration in LiBr water deficient system (FIGS. 3C, 3D), and acid catalyst (HCl) concentration (FIGS. 3E, 3F). Other conditions: 110° C. for 3A-3F; 40% (w/v) initial glucose concentration for 3C, 3D, 3E, and 3F; 60 wt % LiBr for 3A, 3B, 3E, and 3F; 40 mM HCl for 3A, 3B, 3C, and 3D. Hydrate number is the molar ratio of water to LiBr; higher hydrate number means lower LiBr concentration.
Figure 3B:
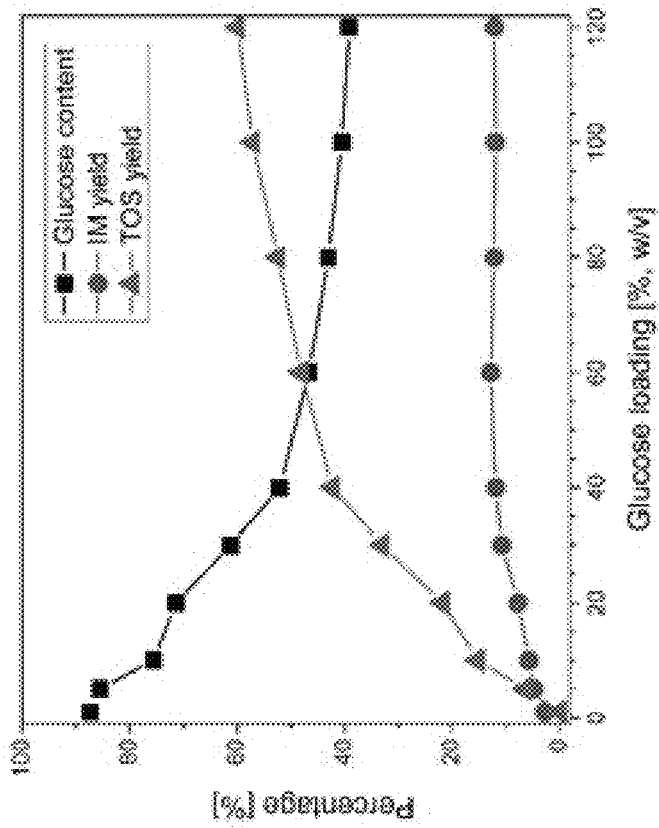

The temperature-dependent reaction curves (FIG. 2) revealed that the glycosylation reaction promptly reached equilibrium within 10 min at 110° C. Therefore, the following investigations regarding the effect of reaction conditions (the starting glucose concentration, LiBr solution, and acid catalyst) were conducted at 110° C., in order to extend the understanding of glucose glycosylation in ALBTH (FIG. 3). The initial concentration of glucose was first tested in a range from 1 to 120% (w/v). At low glucose concentration (≤5%, w/v), over 85.6% glucose was not converted, and the yield of oligosaccharides was lower than 6.4% (FIG. 3A). However, the yields of side-products were relatively higher, including levoglucosan (2.8%), HMF (3.3%), levulinic acid (0.7%), and formic acid (0.2%) (FIG. 3B). The GlOS selectivity also escalated to over 95% with glucose concentrations reaching to 41% (w/w). The results suggested that at low glucose concentration, all the reactions including glycosylation, dehydration, and rehydration proceeded without significant discrepancy, possibly because of their similar reaction activation barriers catalyzed by acid.[20] With the increase of initial glucose concentration, both the consumption of glucose and the formation of the oligosaccharides were enhanced. The yield of oligosaccharides reached 48.0 and 60.0% at the glucose concentration 60 and 120% (w/v), respectively. As glucose acted as both glycosyl donor and glycosyl acceptor in the glycosylation reaction, increasing glucose concentration drove the equilibrium toward the product side and elevated the TOS yield, based on the Le Chatelier's. To further verify this, a reaction mixture containing 39.5% oligosaccharides at equilibrium was diluted two fold with ALBTH (FIG. S2[4] Entries 1 and 4). As expected, the dilution drove the equilibrium back to reactant (glucose) side, and the concentration of TOS dropped to 9.0%.

Very surprisingly, glucose has an extraordinary solubility in ALBTH. For example, glucose could be dissolved or liquefied on ALBTH upto 1000% (w/v), as shown in Table 1, which made it possible to further enhance the yield of GlOSs by elevating glucose concentration. It was found that 40 g glucose could be promptly (in less than 6 min) dissolved in 10 mL ALBTH at 110° C., resulting in a transparent 400% solution of glucose in ALBTH with a manageable viscosity at which a magnet stir bar still worked for mixing. The TOS yield reached 71.1% after 20 min reaction. Further elevation of glucose concentration to 1000% (100 g of glucose in 10 mL of ALBTH) using a fed-batch approach resulted in 75.0% TOC yield within 70 min.

TABLE 1

Glucose glycosylation reaction at ultra-high initial concentration in ALBTH (40 mM HCl) at 110° C.

| Loading (%, w/v) | Time (min) | Recovery (%) Glucose | Yield (%) | | | | | | |
|---|---|---|---|---|---|---|---|---|---|
| | | | IM | GB | TOS | LGA | HMF | LA | FA |
| 200 | 10 | 30.6 | 13.5 | 4.3 | 65.9 | 1.2 | 0.2 | 0.1 | <0.1 |
| | 20 | 27.9 | 9.2 | 3.4 | 69.1 | 0.9 | 0.3 | 0.1 | <0.1 |
| | 20$^a$ | 26.2 | 9.3 | 2.8 | 69.2 | 1.1 | 0.4 | 0.1 | 0.1 |
| 400 | 10 | 39.5 | 12.3 | 4.0 | 58.2 | 0.9 | 0.1 | 0.1 | <0.1 |
| | 20 | 27.0 | 8.3 | 4.3 | 71.1 | 0.9 | 0.1 | 0.1 | <0.1 |
| | 20$^a$ | 22.8 | 7.6 | 3.1 | 74.7 | 1.0 | 0.1 | 0.1 | <0.1 |
| 500 | 20 | 29.1 | 9.6 | 3.9 | 68.8 | 0.8 | 0.1 | 0.1 | <0.1 |
| 700b | 21 | 42.7 | 11.5 | 3.7 | 56.5 | 0.6 | 0.1 | 0.1 | <0.1 |
| 1000b | 70 | 23.3 | 7.6 | 3.3 | 75.0 | 0.6 | 0.1 | 0.1 | <0.1 |

$^a$1.5 eqv of LiBr anhydrous was added after 10 min, based on the weight of water released from the glycosylation reaction.
$^b$A fed-batch strategy was applied to reach 600% (400% + 100% + 100%) and 1000% (500% + 100% + 100% + 100% + 100% + 100%) glucose loading.

It was observed that isomaltose (the dominant disaccharide product) maintained a stable yield (11-12%) when the glucose concentration was over 40% w/v. Further increasing the glucose concentration did not improve the isomaltose yield correspondingly. Actually, a slight decreased isomaltose yield was even observed at ultra-high glucose concentration. This observation did not mean that the production of the disaccharide stopped, but suggested that the resultant disaccharide was consumed by the subsequent glycosylation reaction to form the oligosaccharides with DP ≥3. This was the reason why the disaccharide concentration was stable in the system, while the TOS yield kept increasing with glucose concentration. Interestingly, elevating initial glucose concentration depressed the formation of side-products. For example, the yields of HMF, levoglucosan, and total organic acids decreased by 85%, 57%, and 73%, respectively, when the glucose concentration was increased from 5 to 120% (w/v). At ultra-high glucose concentration (400-1000%, w/v), yields of HMF, levoglucosan, and total organic acids were less than 0.1%, 1.0%, and 0.2%, respectively. These results suggested that elevating initial glucose concentration improved the glycosylation selectivity for GlOS production. It is probably because the dominancy of the glycosylation diminished the tendency of forming C2 carbocation and acyclic glucose, which initiates the degradation of glucose via dehydration and rehydration reactions. In summary, the ALBTH system made it possible to conduct the glycosylation reaction at ultrahigh glucose concentration, which significantly improved the GlOSs yield (>70%).

Example 2.3: LiBr Concentration

Figure 3D:
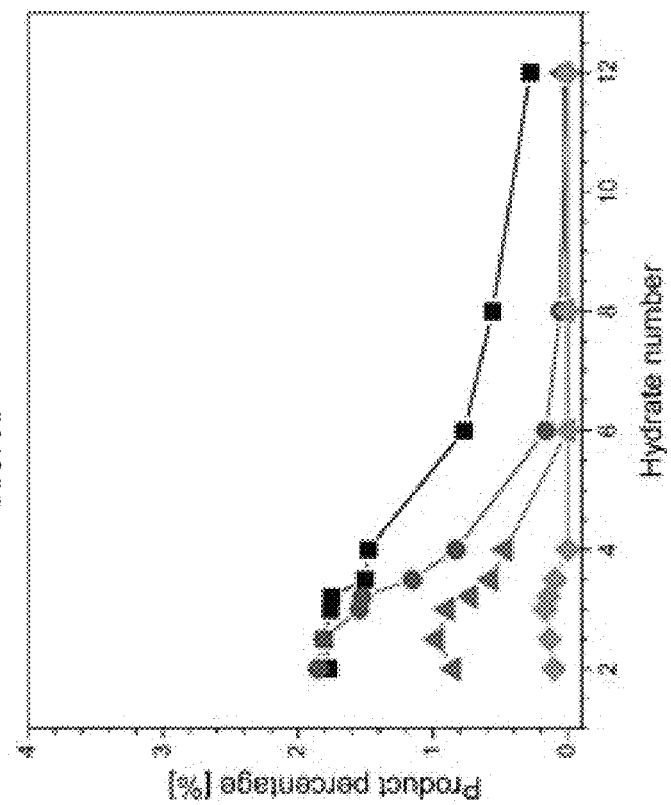
Figure 3C:
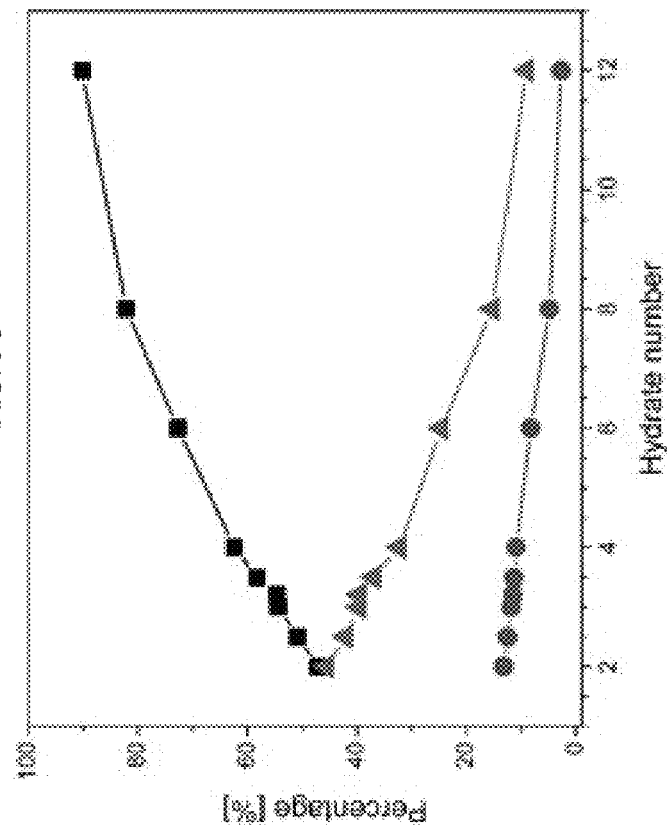

Distinguished from that in dilute sulfuric acid, the glycosylation reaction of glucose in the ALBTH yielded 400% more oligosaccharides under the same initial glucose concentration (FIG. S3[5]). As hypothesized earlier, this was likely attributed to the water-deficient nature of the concentrated LiBr solution, which favors the glycosylation (intermolecular dehydration) of glucose. Theoretically, one mole of Li$^+$ can preferentially coordinate with 3 moles of water. When the water-to-LiBr ratio is larger than 3, "free" (uncoordinated) water is available in the system; on the other hand, when the ratio is smaller than 3, the system is under the water-deficient condition. To investigate the effects of LiBr concentration on the glycosylation reaction, a series of glycosylation reactions were conducted at different LiBr concentrations (varied water to LiBr ratios) (FIGS. 3C and 3D). It is worth noting that the concentration of LiBr increased inversely with the hydrate number (water to LiBr ratio). When the ratio was reduced from 12 (28.7 wt % LiBr) to 3 (61.6 wt % LiBr), the yield of the oligosaccharides increased from 9 to 39.7%, clearly indicating that decreasing water concentration in the system enhanced oligosaccharide formation. Further reducing the ratio to 2 led to extra 5.8% increase in the oligosaccharides yield, confirming that the water-deficient condition of the LiBr:nH$_2$O (n≤3) favored the glycosylation. With the progress of the glycosylation (dehydration) reaction, the water released would dilute the system and drive the equilibrium back to reactant side, which would affect the end GlOSs yield. To address this issue, a strategy of adding anhydrous LiBr during the glycosylation reaction was tested with the aim to bind the free water released. The results in Table 1 clearly indicated that the addition of anhydrous LiBr (1.5 eqv to water released, w/w) did elevate the yield of the oligosaccharides up to 74.7%, which was 3.6% higher than that in the control experiment without adding LiBr. This observation once again verified that a water deficient environment had a positive effect on oligosaccharide production. The results and observations above confirmed the hypothesis that the water-deficient nature of the ALBTH system favors the glycosylation of glucose.

A similar trend was observed how the yields of levoglucosan, HMF and organic acids were affected by the LiBr concentration. This is in agreement with our previous study that the acid-catalyzed glucose dehydration to side-products was promoted in the water-deficient molten salt hydrate system. It is worth noting that the yield of sugar degradation side-products was less than 2% over the whole range of LiBr concentrations investigated.

Example 2.4: Acid Catalyst

Figure 3F:
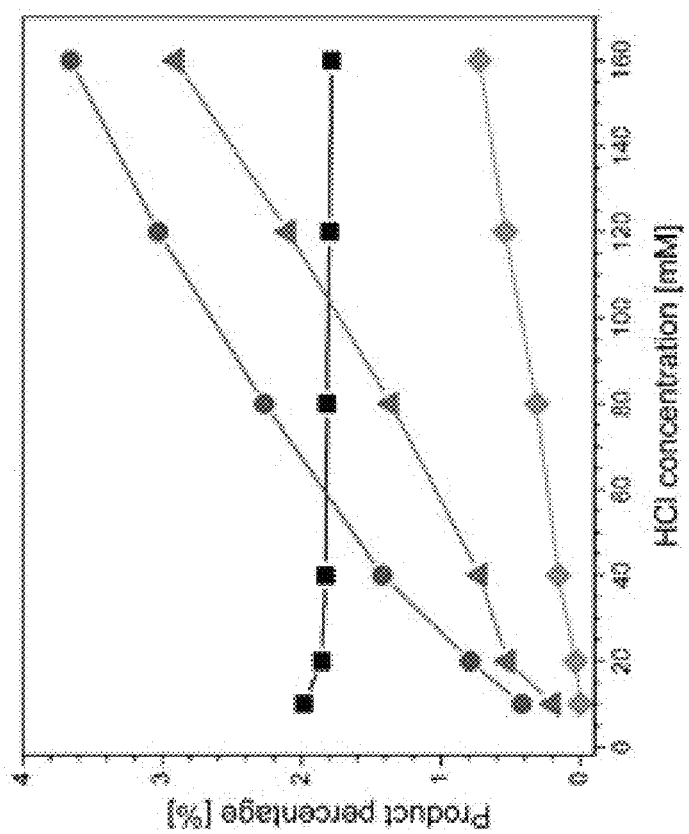
Figure 3E:
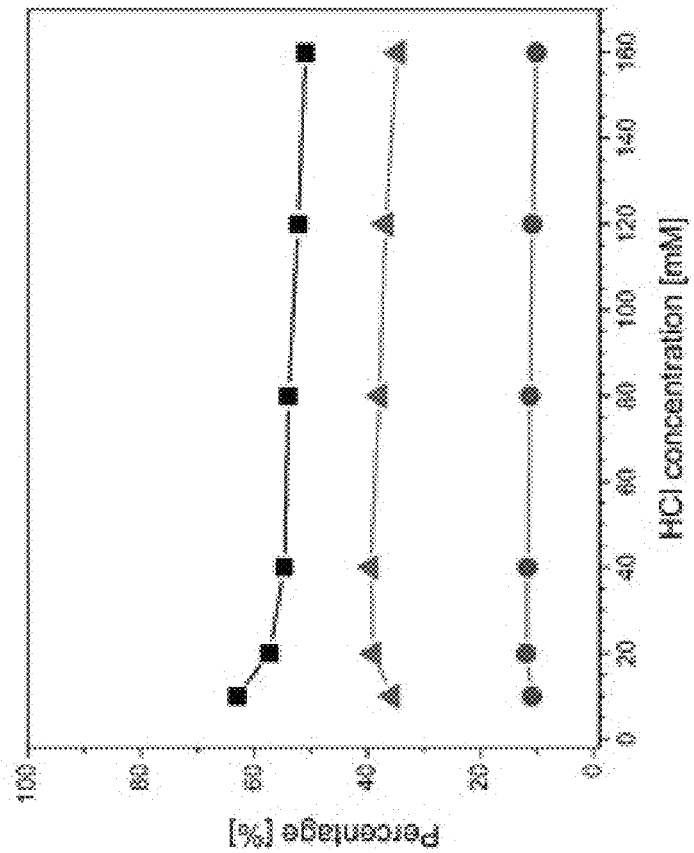
Figure 4:
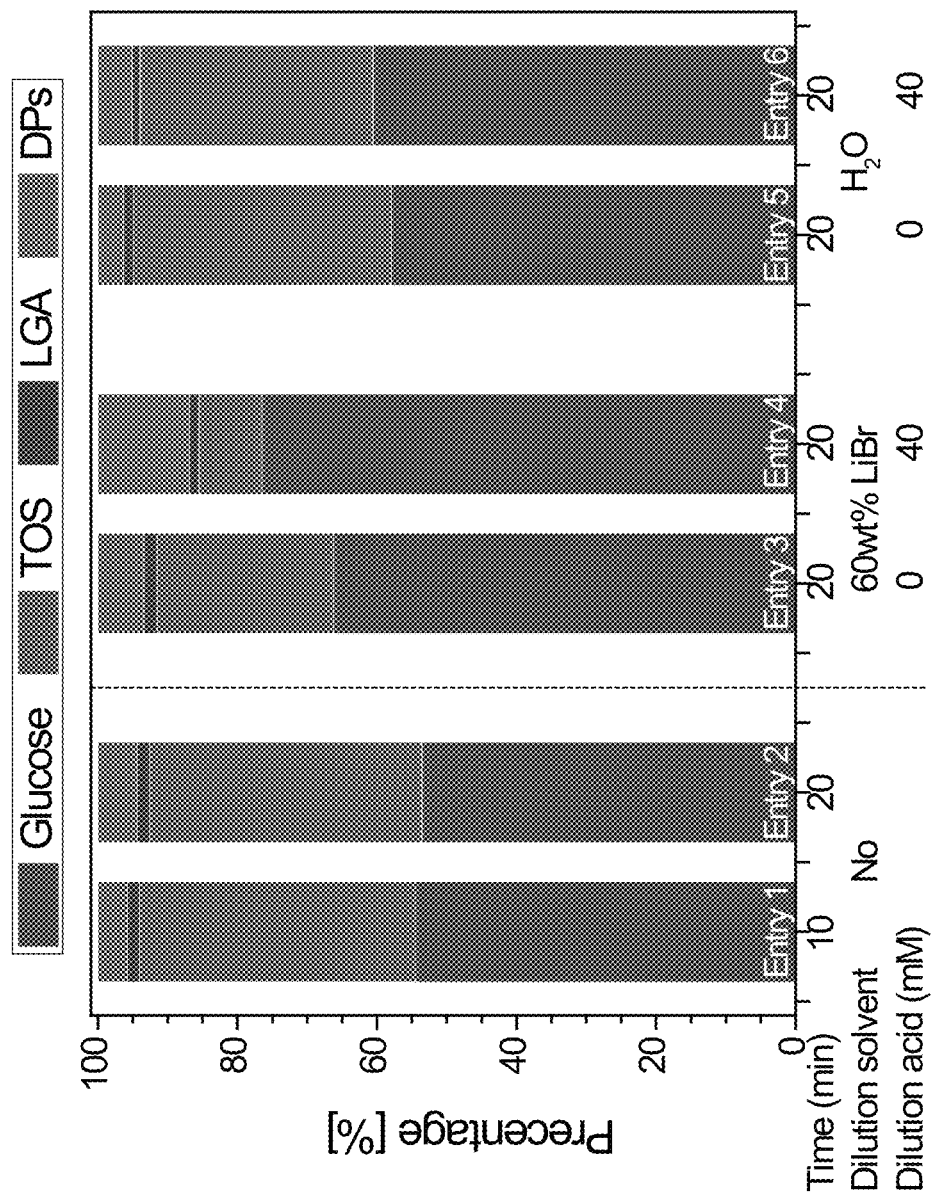
FIG. 4. Distribution of GlOSs and sugar degradation by-products from acid catalyzed glycosylation of glucose in ALBTH at 110° C. Reaction time was 20 min except Entry 1 and the reaction equilibrium was broken by dilution after 10 min of reaction. TOS, LGA, and DPs denote total oligosaccharides, levoglucosan, and degradation products, respectively.
Figure 5:
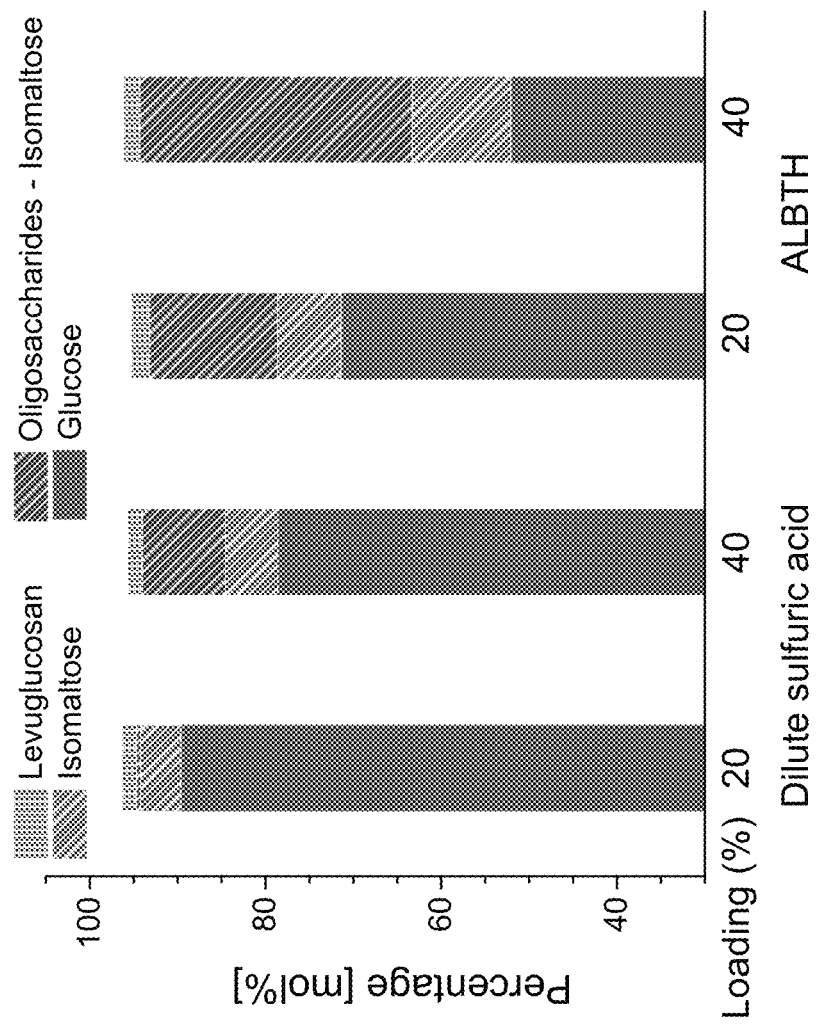
FIG. 5. Comparison between the glycosylation reactions of glucose in dilute sulfuric acid (121° C. for 60 min) and in ALBTH (110° C. for 10 min) in residual glucose content, GlOS yield, and sugar degradation by-product yield.

The prerequisite for the glycosylation to occur and the formation of new glycosidic bonds between glucose molecules is the protonation of the anomeric hydroxyl group of glucose followed by the formation of an anomeric carbon cation intermediate via water elimination. Hydrochloric acid, a strong Brønsted acid, was investigated as catalyst to protonate the anomeric hydroxyl group at various concentrations, as shown in FIGS. 3E and 3F. When the acid concentration increased from 10 to 160 mM, the yield of the oligosaccharides first increased slightly from 35.7% to 39.4% (at 40 mM) and then gradually decreased to 34.6%. It seemed that 10-20 mM acid was insufficient to catalyze the glycosylation. However, excessive acid (>40 mM HCl) did not further improve the yield of the oligosaccharides, but enhanced the sugar degradation (FIG. 3F). The results suggested that the acid concentration did not thermodynamically impact the glycosylation reaction equilibrium, but kinetically affected the reaction rate. This observation in the ALBTH system was consistent with that in dilute sulfuric acid system.[20] The results also indicated that the catalytic role of the strong Brønsted acid in the glycosylation of glucose was similar in both solvent systems (water and LiBr solution).

Weak acids are usually ineffective in rupturing the glycosidic bonds during the carbohydrate hydrolysis, because the basicity of the carbohydrate oxygen follows the order: anomeric oxygen>hydroxyl oxygen>glycosidic oxygen.

Whereas the acid-catalyzed glycosylation reaction (a reverse reaction of carbohydrate hydrolysis) starts from the formation of the carbocation via protonating the C1 hydroxyl group of glucose (since C1 hydroxyl group has high proton affinity), a weak acid might be able to catalyze the glycosylation of glucose. A group of acids with varied pKa values were investigated for catalyzing the glycosylation reaction. As shown in Table 2, using the acids with pKa values in the range from −4 to 2.16, the oligosaccharide yields were indistinguishable, indicating that relatively weak Brønsted acids, such as phosphoric acid and oxalic acid, were as effective as the strong Brønsted acids in catalyzing the glycosylation reaction. It seemed that formic acid (pKa=3.75) was still able to catalyze the reaction, though glucose conversion and product yield were low. However, glycosylation of glucose was barely observed when acetic acid was used as the catalyst, even at high concentration up to 200 mM. These results suggested that acids with pKa>4.7 were ineffective as the acid catalyst for glucose glycosylation in ALBTH.

TABLE 2

Comparison of the acids (40 mM) with various pKa values in catalyzing glucose glycosylation in ALBTH at 110° C.

| Acids | pKa | Content (%) Glucose | IM | GB | Yield (%) TOS | LGA | HMF | LA | FA |
|---|---|---|---|---|---|---|---|---|---|
| HCl | −4.00 | 55.6 | 11.7 | 2.6 | 38.0 | 1.6 | 1.8 | 0.7 | 0.2 |
| $H_2SO_4$ | −3.00 | 55.7 | 12.9 | 2.5 | 38.5 | 1.6 | 2.0 | 0.9 | 0.2 |
| TsOH | −2.80 | 55.4 | 12.9 | 2.1 | 38.1 | 1.4 | 1.9 | 0.8 | 0.1 |
| Oxalic acid | 1.25 | 54.0 | 12.5 | 2.1 | 39.4 | 1.7 | 1.8 | 0.4 | 0.2 |
| DCA | 1.35 | 57.9 | 12.5 | 3.1 | 35.9 | 0.9 | 2.0 | 0.3 | 0.1 |
| $H_3PO_4$ | 2.16 | 56.9 | 13.2 | 2.4 | 39.1 | 1.1 | 1.8 | 0.4 | 0.1 |
| Citric acid | 3.13 | 64.7 | 11.5 | 2.9 | 31.6 | 0.5 | 2.2 | 0.2 | 0.0 |
| Formic acid | 3.75 | 88.3 | 4.0 | 1.5 | 9.5 | 0.1 | 1.0 | 0.1 | 0.3 |
| Acetic acid | 4.76 | 100.0 | 0.0 | 0.0 | 0.0 | 0.0 | 0.0 | 0.1 | 0.0 |
| Acetic acid[a] | 4.76 | 95.7 | 2.6 | 0.0 | 3.1 | 0.0 | 0.5 | 0.1 | 0.0 |
| Control[b] | 7.00 | 87.8 | 0.0 | 0.0 | 0.0 | 0.0 | 0.0 | 0.0 | 0.0 |

[a]Acid concentration: 200 mM;
[b]LiBr trihydrate (60 wt %) without acid catalyst TOS, IM, GB, LGA, HMF, LA, and FA denote total oligosaccharides, isomaltose, gentiobiose, levoglucosan, hydroxymethylfurfural, levulinic acid, and formic acid, respectively.

In a control experiment in 60 wt % LiBr without acid catalyst, approximately 12% of glucose was converted, but no disaccharides and oligosaccharides. Only fructose and mannose were identified as the conversion products, suggesting that isomerization and epimerization of glucose occurred in the neutral LiBr solution. This observation is consistent with our previous study. Since the isomerization in LiBr mostly follows the proton transfer mechanism, the presence of protons (even weak acids) would greatly inhibit the isomerization reaction, depressing the release of proton from C2 of glucose. As a result, the dominant reaction in acidic lithium bromide trihydrate was the glycosylation not the isomerization (Table 1). The observations above verified the essential role of acid in catalyzing the selective glycosylation of glucose in the ALBTH system.

Example 2.5: Separation and Purification of GlOSs and Recovery of LiBr

After the glycosylation reaction of glucose in ALBTH, it is necessary to separate the oligosaccharides from the reaction medium and recycle/reuse the LiBr solution. Since the saccharides have similar polarity to LiBr, it was challenging to separate them economically using the solvent-solvent extraction strategy. However, the saccharides and LiBr have distinct solubility in water and organic solvent. For example, LiBr is soluble in both water and polar organic solvents like alcohols and acetone, while the saccharides have very limited solubility in the organic solvents above. Herein, we established an effective anti-solvent precipitation approach to separate oligosaccharides from the reaction media and recover LiBr. The method is based on the principle that the addition of the anti-solvent in a solution can effectively interrupt the original solvent and solute interaction, leading to an over-saturation and precipitation of the solute because of the reduced solubility. Compared to alcohols (methanol and ethanol), acetone was chosen as the anti-solvent in virtue of its low dielectric constant (20.7) and the absence of protic atoms. In addition, acetone is miscible with LiBr trihydrate because of the coordination between carbonyl and lithium.

When the glucose glycosylation reaction was carried out at high glucose concentration, the resultant products syrup was viscous. Pouring the viscous syrup directly into acetone tended to form sugar gums that entrapped a significant amount of LiBr and water, which made the separation of saccharides and LiBr extremely challenging. Therefore, it was necessary to dilute the syrup prior to the anti-solvent precipitation in acetone to facilitate the recovery of the GlOSs and LiBr. Dilution with DI water was firstly tested to reduce the syrup viscosity. However, the drawback of water dilution was the reduced GlOS yield after precipitation since the solubility of the GlOSs in water-containing acetone is higher than that in anhydrous acetone. Alternatively, methanol (dielectric constant 32.6, a moderately polar solvent) was chosen as the diluting reagent. Although it is slightly less polar than water, methanol, distinguished from other long-chain alcohols, is still capable of dissolving the oligosaccharides. In addition, the methanol dilution attenuated the saccharide agglomeration and gum formation.

When dropping the methanol-diluted syrup into acetone, the GlOSs were quantitatively regenerated as white precipitates without formation of gum-like chunk. Methanol and acetone are much more volatile than LiBr trihydrate, and they can be feasibly recovered by vacuum evaporation. The LiBr solution left over along with unreacted glucose can be directly reused in the next batch of reaction.

The effect of dilution factor on the separation of the GlOSs was investigated. The resultant product syrup was diluted 2-15 folds with methanol and then dropped into acetone. It was apparent that the methanol dilution exerted positive effects on the fraction separation and purification of the GlOSs. As shown in Table 3, when the methanol dilution factor was increased from 2 to 15, the glucose and LiBr co-precipitated with the GlOS fraction decreased from 25.0 and 66.5% to 6.5 and 20.3%, respectively, while the yield of TOS in the precipitates was barely affected, only decreasing from 89.2% to 86.3%. This was because the solubility of the GlOSs was reversely related to their molecular weight (DP).

TABLE 3

Separation of GlOSs and LiBr using anti-solvent precipitation method

|  |  | Methanol dilution | | |
|---|---|---|---|---|
|  |  | 2× | 5× | 15× |
| After reaction | LiBr (g) | 5.13 | 5.13 | 5.13 |
|  | Glucose (g) | 2.18 | 2.22 | 2.17 |
|  | TOS (g) | 2.77 | 2.73 | 2.78 |
|  | IM (g) | 0.68 | 0.65 | 0.69 |
|  | GB (g) | 0.21 | 0.20 | 0.19 |
| Anti-solvent precipitates | LiBr (g) | 1.28 | 0.78 | 0.33 |
|  | Glucose (g) | 1.45 | 1.07 | 0.44 |
|  | TOS (g) | 2.47 | 2.43 | 2.40 |
|  | IM (g) | 0.58 | 0.52 | 0.43 |
|  | GB (g) | 0.20 | 0.15 | 0.13 |
| Recovered LiBr hydrate | LiBr (g) | 3.70 | 3.98 | 4.62 |
|  | Glucose (g) | 0.51 | 0.75 | 1.30 |
|  | TOS (g) | 0.30 | 0.30 | 0.38 |
|  | IM (g) | 0.02 | 0.06 | 0.17 |
|  | GB (g) | 0.01 | 0.02 | 0.13 |
|  | Methanol (g) | 0.08 | 0.01 | 0.05 |
|  | Acetone (g) | 0.02 | 0.00 | 0.24 |

TOS-total oligosaccharides;
IM-isomaltose;
GB-gentiobiose.
Reaction condition: 5 g glucose in 5 mL 60 wt % LiBr with 40 mM HCl at 70° C. for 2 h.

Acetone and methanol were feasibly removed from the supernatant by vacuum evaporation, and only a trace amount of methanol and acetone were detected in the recovered LiBr solution. It is worth mentioning that high dilution factor (e.g., 15) increased the sugar carryover into the recovered LiBr solution, in spite of improving the overall recovery of the oligosaccharides and LiBr. The recovered LiBr solution with the glucose and GlOSs carried over could be directly used for next batch of glycosylation reaction. This was verified by a test in which fresh glucose was added to the recovered LiBr solution from the first batch for the second batch reaction. The yield of the TOS (55.5%) was comparable to that (56.2%) using fresh LiBr solution. The mixture of methanol and acetone recovered from evaporation can be readily separated via distillation. If necessary, the precipitated oligosaccharide fraction could be further purified by repeating the dissolution-precipitation operation. For example, 0.5 g of the coarse GlOSs (86.7% purity) was re-dissolved in 3 mL of methanol/water mixture (2:1), and then reprecipitated in 40 mL of acetone. After repeating the dissolution-precipitation process twice, the purity of the GlOS fraction reached 97.8% with a negligible amount of LiBr impurity.

Example 3: Identification and Characterization of GlOSs

Figure 6:
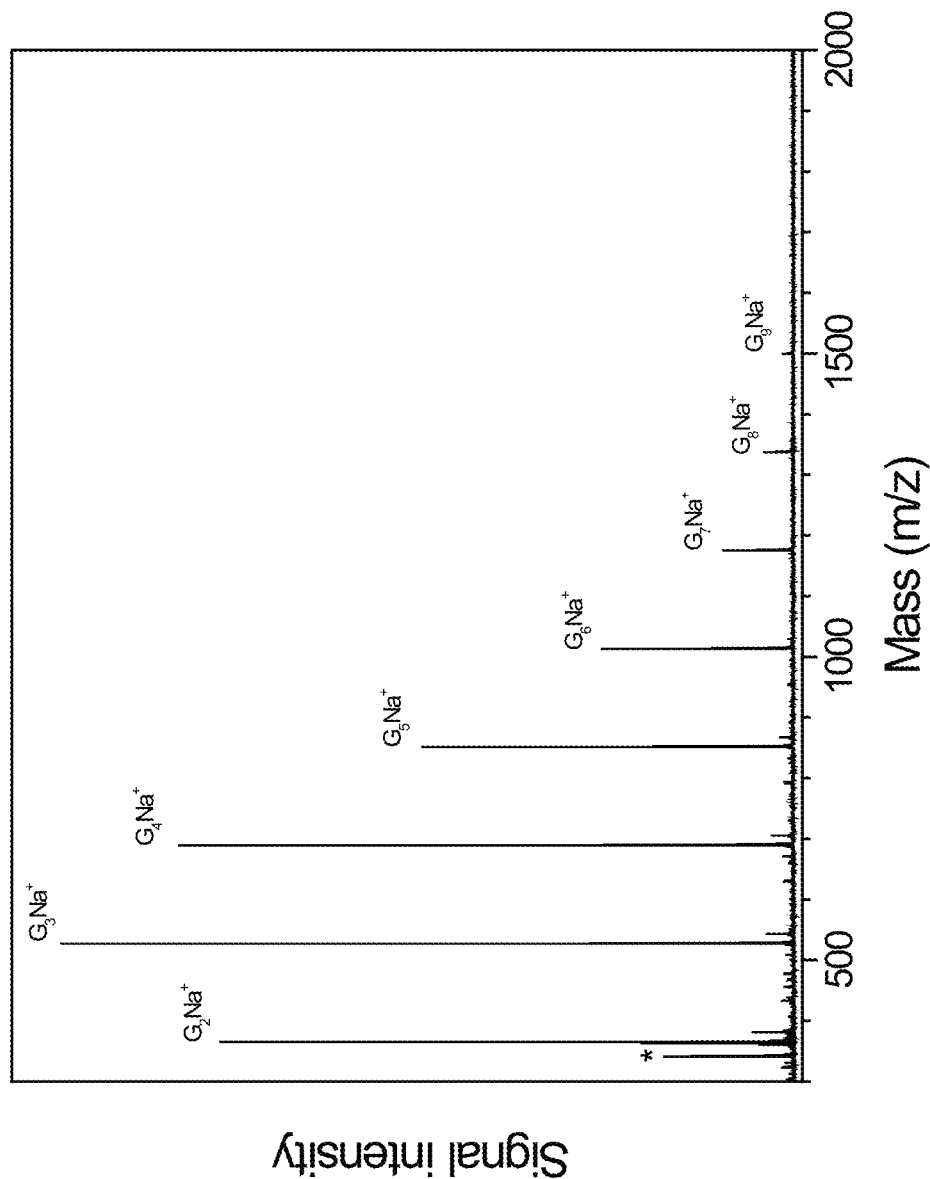
FIG. 6. MALDI-TOF MS spectrum of GlOS from acid catalyzed glycosylation reaction of glucose in ALBTH. The MS peaks are marked with $G_nNa^+$, in which n represents the number of glucose unit (G) in the oligosaccharide. The m/z values correspond to $[G_nNa^+]$.
Figure 12:
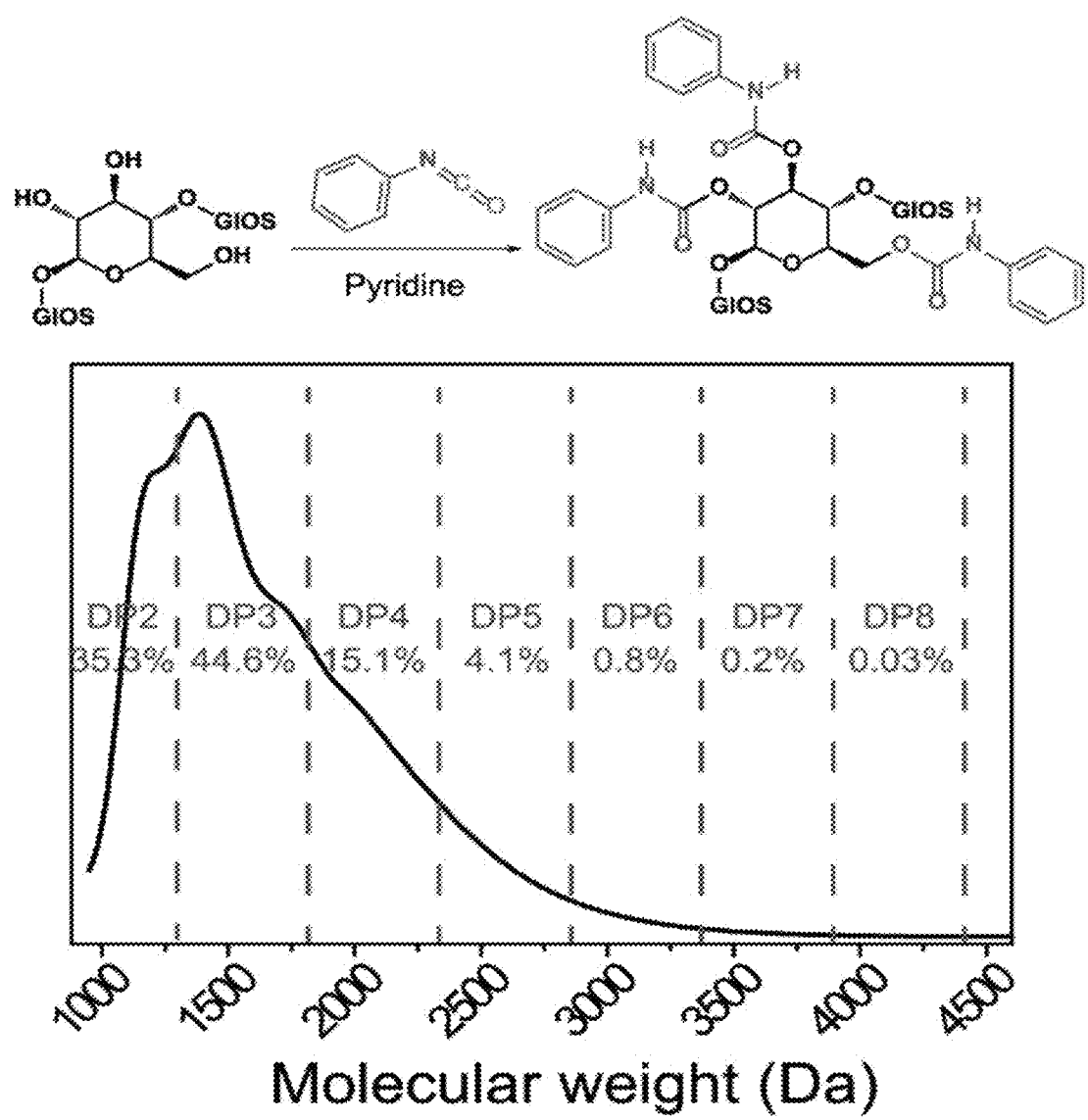
FIG. 12 is a GPC chromatogram showing the DP distribution of GlOS from acid catalyzed glycosylation reaction of glucose in ALBTH.

In the glycosylation products of glucose in ALBTH, isomaltose (the predominant disaccharide product) only accounted for 20-30% of total oligosaccharides. This observation was distinct from those reported in diluted sulfuric acid where negligible oligosaccharides (DP>2) were identified from the glycosylation.[19-21] In order to verify the formation of GlOSs longer than disaccharides, MALDI-TOF MS analysis was conducted. The spectrum clearly showed the peaks of the GlOSs consisting of 2-9 glucose units (FIG. 6). The mass value of the peaks increased at an interval of 162, indicating that oligosaccharides were purely composed of glucose units. There was no evidence that sugar degradation products (such as levoglucosan, HMF and organic acid) were incorporated into the GlOSs. The relative intensity of the GlOS peaks in the MALDI-TOF MS spectrum suggested that most of the oligosaccharides were composed of 2 to 5 glucose units. The DP of the GlOS was further estimated by GPC chromatography. As shown in FIG. 12, the GlOS had an average DP of 2.9, composed of approximately 35% disaccharides and 65% oligosaccharides (DP>2). The most abundant oligosaccharides were trisaccharides (45%), followed by tetrasaccharides (15%) and pentasaccharides (4%), along with only a small amount (~1%) of larger oligosaccharides (DP>5). These results were in agreement with the MALDI-TOF MS spectrum (FIG. 6), suggesting that the majority (~65%) of the oligosaccharides from glucose glycosylation in ALBTH had DP higher than 2. This is distinct from the traditional acid-induced glycosylation in water where the oligosaccharides with DP>2 were negligible.

In an effort to identify the glycosylic linkages formed during the glycosylation of glucose in ALBTH, the GlOSs were dissolved in $D_2O$ and characterized using 2D-HSQC NMR. The $^1H$-$^{13}C$ correlation contours of the GlOSs were assigned according to the assignments of available dimer standards and reported standard oligosaccharides. Varying glycosylic linkages were observed, including $\alpha/\beta$-1,1-, $\alpha/\beta$-1,2-, $\alpha/\beta$-1,3-, $\alpha$-1,4-, $\alpha/\beta$-1,6-glycosylic bonds. The regio- and stereo-selectivity during the glycosylation of glucose in ALBTH was investigated using HSQC NMR experiments with 10 s relaxation delay. The semi-quantitative flavor of the "hsqcetgpsisp 2.2" pulse program for the GlOSs was assumed considering the insignificant T2 effects due to the low molecular weight of GlOSs (less than 1500 Da) from MALDI-TOF MS spectrum and similar one bond coupling constants ($^1J_{C-H}$) between the various anomeric C1-H1 correlations (ranging from 158-172 Hz with the $^1J_{C-H}$ of β-anomers 10-15 Hz higher than that of α-anomers). As shown in Table 4, the (1→6) glycosylic linkages were the most abundant (up to 69.0%). Other glycosylic linkages decreased in the order of (1→3)>(1→2)>(1→4)≈(1→1). In terms of the stereo-conformation, α-anomeric linkages were favorable. The ratios of α to β conformations in (1→6), (1→3), and (1→2) glycosylic linkages were 2.5, 4.2, and 11.3, respectively. Notably, no β-1,4 glycosylic linkage (the characteristic contour of C4-H4 correlation at 3.65/81.1 ppm) was detected in the HSQC NMR spectrum. The absence of β-1,4 glycosylic linkage was further confirmed by the fact that no cellobiose peak was observed in the HPIC chromatogram of the glycosylation products. As a result, we would assume the α/ββ ratio of (1→4) glycosylic linkages higher than 10. The results and observations above suggested that C2, C3 and C4 hydroxyl groups have much better stereo-selectivity as the glycosyl acceptor than the most regio-selective C6 hydroxyl group in glycosylation reaction. This is in agreement with the mechanism of the glycosylation because C6 hydroxyl group is the most reactive and less stereo-controlled glycosyl acceptor (no significant difference in energy barrier of forming α- or β-linkage) in the glycosylation. Increasing the glycosylation temperature from 70 to 110° C. (Table 4) did not have significant effect on the glycosyl contents and the ratios of α/β conformations, indicating the regio- and stereo-selectivity of the glycosylation was barely affected by the reaction temperature in the investigated range.

TABLE 4

The regio- and stereo-selectivity of the glycosylation reaction for GlOSs production

| | 70° C. | | | | 110° C. | | | |
| --- | --- | --- | --- | --- | --- | --- | --- | --- |
| | D1 = 10 s | | D1 = 1 s | | D1 = 10 s | | D1 = 1 s | |
| Glycosylic linkage | Cont. (%) | α/β ratio | Cont. (%) | α/β ratio | Cont. (A) | α/β ratio | Cont. (A) | α/β ratio |
| 1→6 | 69.1 | 2.5 | 69.3 | 2.6 | 69.8 | 3.1 | 68.0 | 3.0 |
| 1→4 | 4.9 | >10 | 4.5 | >10 | 3.0 | >10 | 3.4 | >10 |
| 1→3 | 13.7 | 4.2 | 12.5 | 4.3 | 13.5 | 2.1 | 12.9 | 2.5 |
| 1→2 | 8.8 | 11.3 | 8.8 | 9.1 | 9.7 | 10.0 | 10.9 | 7.7 |
| 1→1 | 3.6 | 1.3 | 1.9 | 1.4 | 4.0 | 2.6 | 4.8 | 2.2 |

The GlOSs synthesized in the regenerated ALBTH were also analyzed with HSQC NMR, and the resultant spectrum was identical to that of the GlOSs synthesized in fresh ALBTH. This further confirmed that the recovered LiBr solution was directly reusable without showing marginal distinction from fresh LiBr solution as reaction medium for the glycosylation reaction in terms of both product yield and structure.

Figure 15:
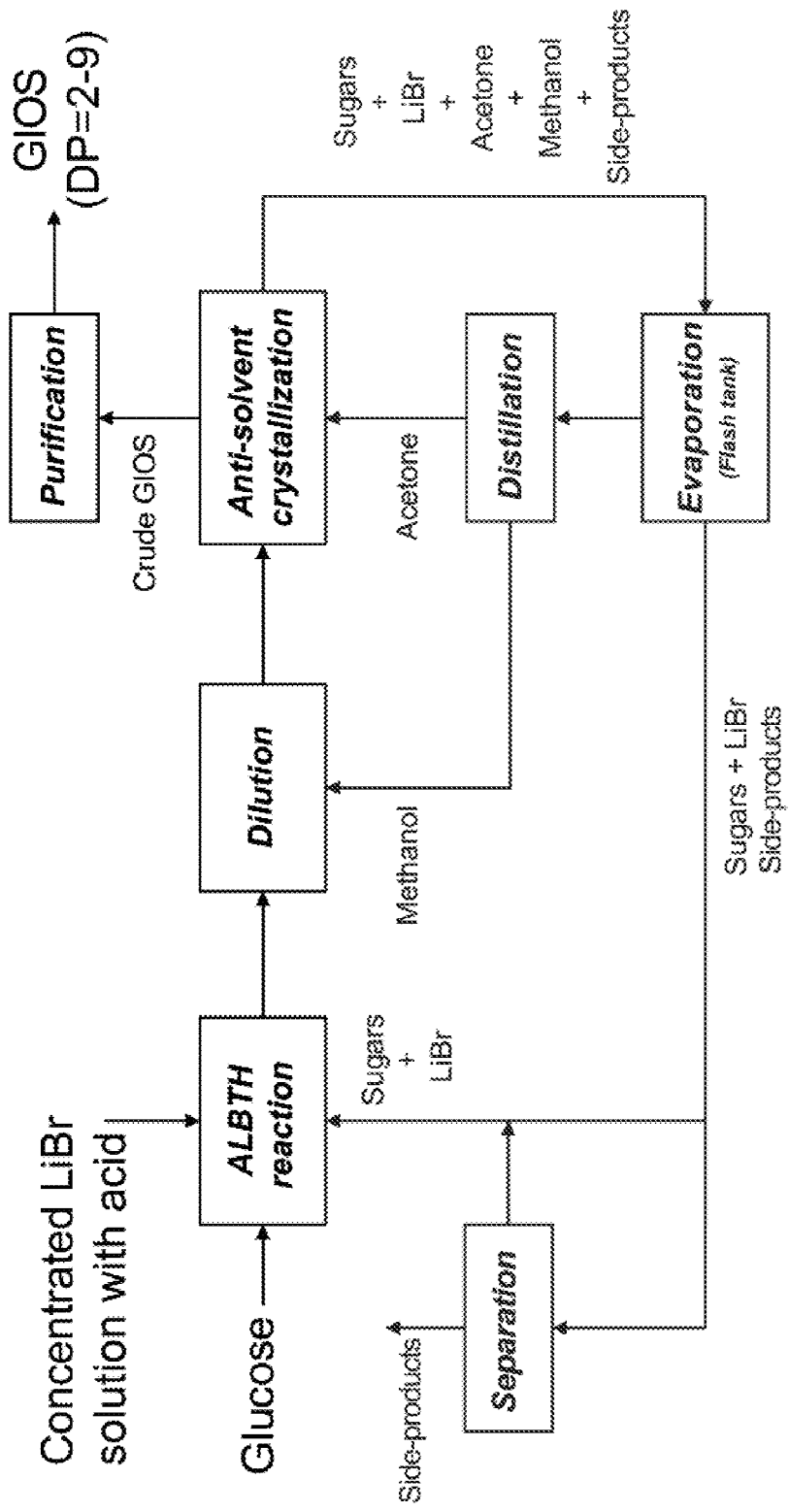
FIG. 15 is a scheme showing a process for GlOS production including separation and purification according to the examples.

An exemplary process for the separation and purification is provided in FIG. 15.

Example 4: Evaluation of the GlOSs as Potential Prebiotics, In Vitro

It has been reported that the isomalto-oligosaccharides and gentiobio-oligosaccharides (linked via α-1,6- and β-1,6-glycosidic bonds, respectively) had prebiotic property. The oligosaccharides with α/β-1,1-, α-1,2-, and α-1,3-linkages glycosidic bonds were also able to promote the growth of probiotics with high prebiotic index (PI, a summary of competition factors between beneficial and undesired influences resulting from prebiotics). As discussed above, the α-1,6- and β-1,6-glycosyls were the most abundant glycosylic linkages in the GlOSs synthesized in the ALBTH system. The glycosidic bonds via α/β-1,1-, α-1,2-, and α-1,3-linkages were also observed in the GlOSs. The results above suggested that the over 91% of the glycosyls in GlOSs were of the potential prebiotic properties.

Figure 7:
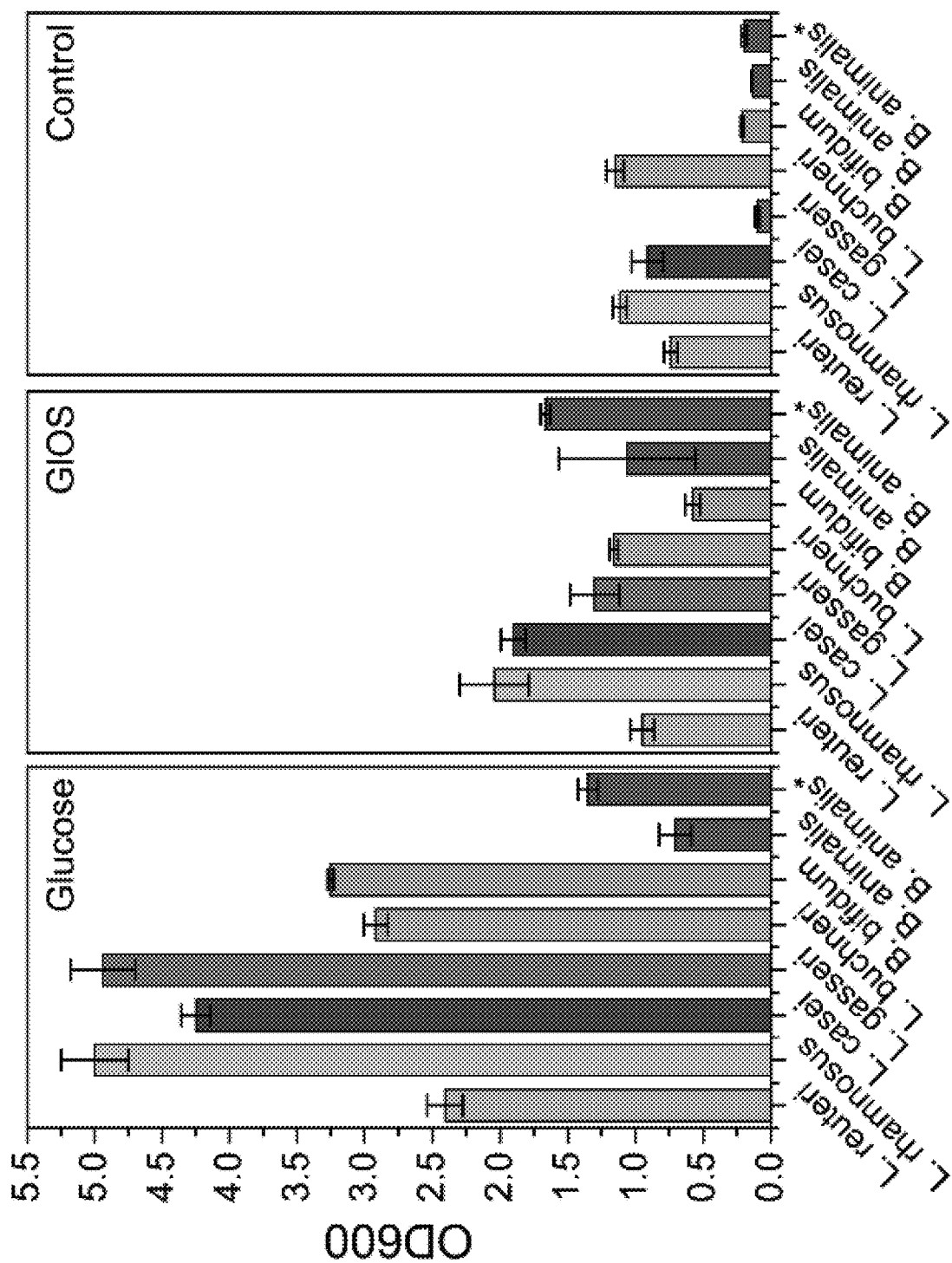
FIG. 7 is a bar graph showing the growth of *Lactobacillus* and *Bifidobacterium* strains on glucose and gluco-oligosaccharides (GlOS) after 24 h anaerobic incubation at 37° C.

In order to demonstrate the fermentability of the oligosaccharides by probiotic strains, the gluco-oligosaccharides (GlOS) synthesized from glucose in the ALBTH system was preliminarily examined as the carbohydrate energy source of the probiotic strains under anaerobic conditions in vitro. The growth of five selected *Lactobacillus* and two selected *Bifidobacterium* strains on GlOS was observed. In the modified medium containing GlOS, probiotic bacteria proliferated after 24-h incubation but at different efficiencies, ranging from a final optical density (OD600) from 0.6 (*B. bifidum*) up to 2.0 (*L. rhamnosus* GG) (FIG. 7). Since the GlOS preparation contained a small amount of glucose (5 wt %), it was assessed if the supported growth could be attributed to the free glucose rather than GlOS utilization. The results show that glucose was predominately metabolized in the first 3-4 h, and the GlOS contributed to the subsequent growth of the probiotic bacteria which were distinct from the limited glucose control (FIGS. 13A-13D). This provides direct evidence that the select probiotics can utilize GlOS for growth.

TABLE 5

Consumption of glucose and GlOS by probiotics and the resultant SCFA production after 24 h anaerobic incubation at 37° C.

| | Substrate consumption (%) | | | | SCFA conc$^a$ (g/L) | | | | |
| --- | --- | --- | --- | --- | --- | --- | --- | --- | --- |
| | Glucose | TOS$^b$ | IMO | GB | LcA | FA | AA | PA | BA |
| | | GlOS | | | | | | | |
| *L. reuteri* | 100.0 | 21.6 | 25.0 | 100.0 | 0.9 | <0.1 | 1.1 | <0.1 | <0.1 |
| *L. buchneri* | 100.0 | 25.5 | 90.7 | 0.0 | 1.2 | <0.1 | 1.1 | <0.1 | <0.1 |
| *B. bifidum* | 100.0 | 12.7 | 12.1 | 2.4 | 2.2 | <0.1 | <0.1 | <0.1 | <0.1 |
| *B. animalis* | 10.9 | 40.6 | 42.6 | 47.5 | 0.9 | 0.3 | 1.4 | <0.1 | <0.1 |
| *B. animalis$^c$* | 69.4 | 42.7 | 79.9 | 74.1 | 1.6 | 0.3 | 2.3 | <0.1 | <0.1 |
| *L. rhamnosus* GG | 100.0 | 27.2 | 13.9 | 99.0 | 0.3 | 0.6 | 1.5 | <0.1 | <0.1 |
| *L. casei* | 98.2 | 20.9 | 21.1 | 95.5 | 1.0 | 0.2 | 1.3 | <0.1 | <0.1 |
| *L. gasseri* | 99.4 | 26.1 | 15.4 | 98.1 | 2.1 | 0.3 | 1.4 | <0.1 | <0.1 |

$^a$Production of SCFA by GlOS fermentation, LcA, FA, AA, PA and BA denote lactic, formic acetic, propionic, and butyric acid, respectively.
$^b$TOS is total oligosaccharides.
$^c$Incubation duration: 48 h The carbohydrate analysis of the post-fermentation broth (Table 5) indicated that GlOS were partially consumed by both *Lactobacillus* and *Bifidobacterium* strains. For example, *L. rhamnosus* GG and *L. reuteri* utilized gentiobiose completely, and *L. buchneri* consumed more than 90% isomaltose, but not gentiobiose. *B. animalis* consumed more than 70% of 1→6 glycosylic disaccharides and up to 43% of total oligosaccharides. Consumption of total oligosaccharides by *B. animalis* was leveling off after 24 h possibly due to its poor ability to utilize long-chain oligosaccharides in GlOS. It was reported that *Lactobacillus* and *Bifidobacterium* strains were less effective in utilizing long-chain oligosaccharides, though long-chain oligosaccharides could be utilized by other faecalibacterium as prebiotics. The metabolic activities of probiotic strains produced short chain fatty acids (SCFA) as fermentation products. The production of formic acid (0.2-0.6 g/L), acetic acid (0.6-2.3 g/L) and lactic acid (0.3-2.2 g/L) on GlOS was strain-dependent. Direct production of propionate or butyrate was negligible by *Lactobacillus* and *Bifidobacterium* strains in this study, although both lactate and acetate could be utilized by a group of bacteria such as *Eubacterium hallii* and *Anaerostipes caccae* to produce propionate and/or butyrate.

Figure 8A:
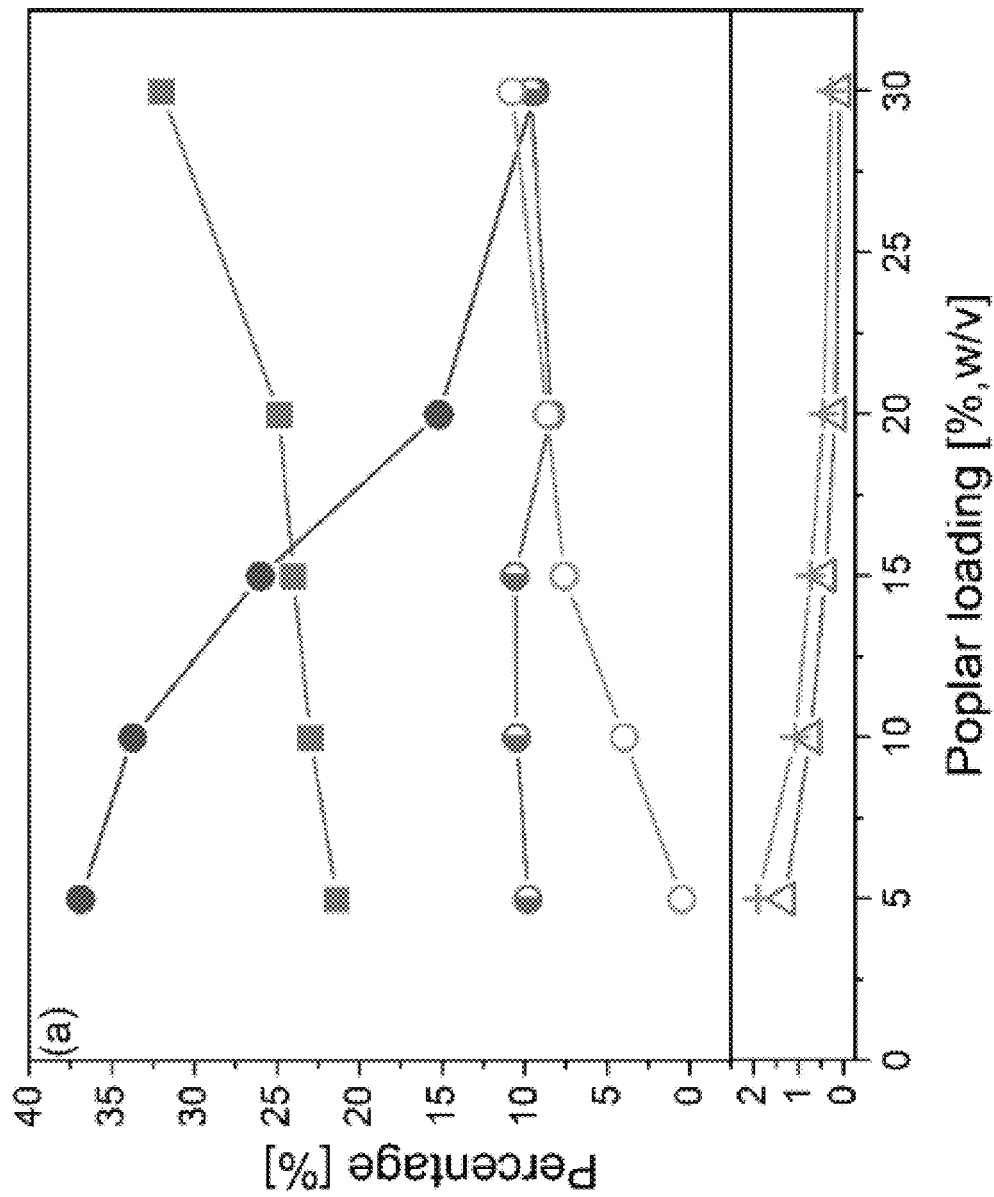
FIGS. 8A-8C are graphs showing the effects of poplar loading (2.5%-30%, w/v) on yields of aqueous soluble monosaccharides and oligosaccharides at varied acid concentration in ALBTH at 110° C. See Example 5 for conditions.
Figure 8B:
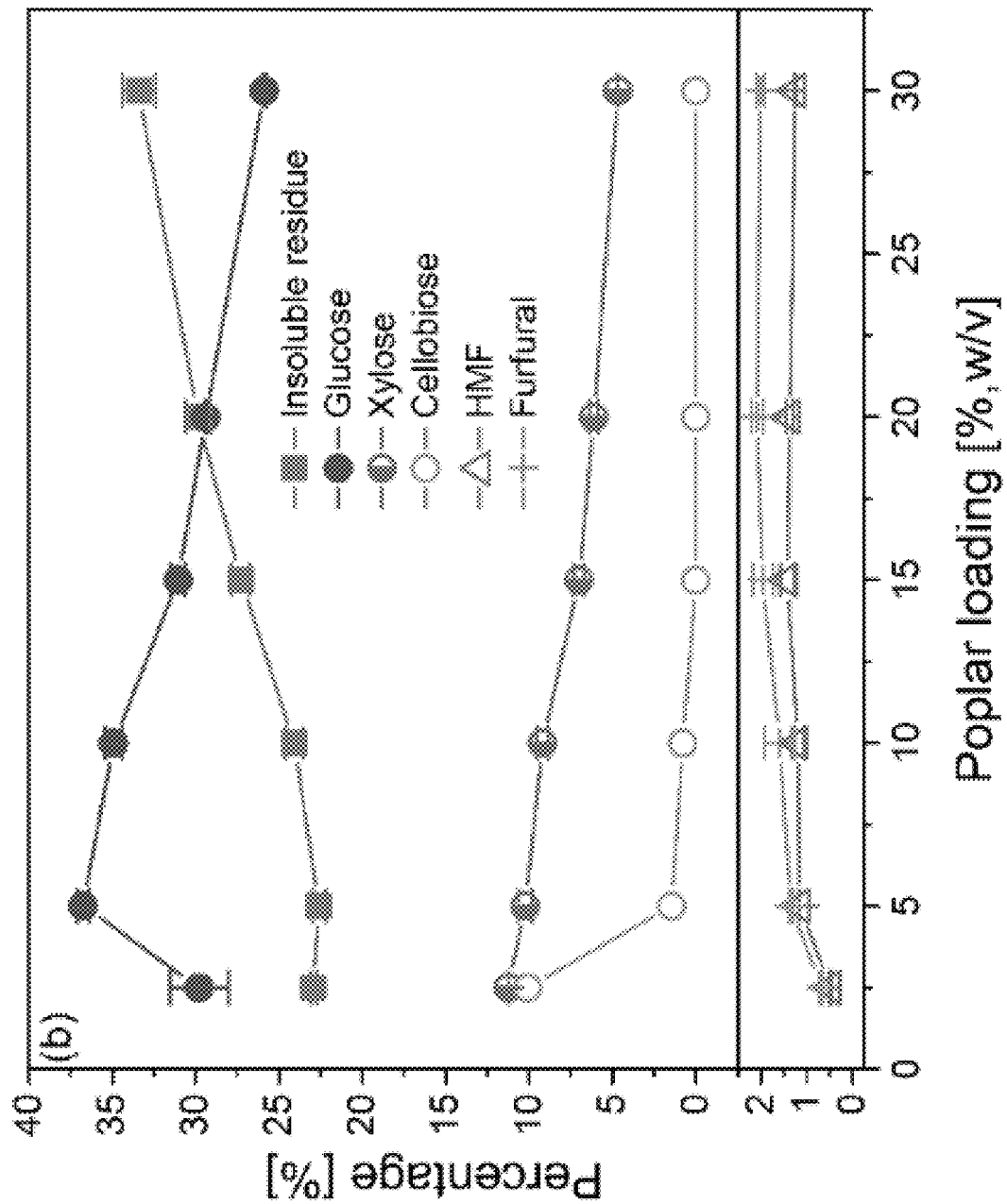
Figure 8C:
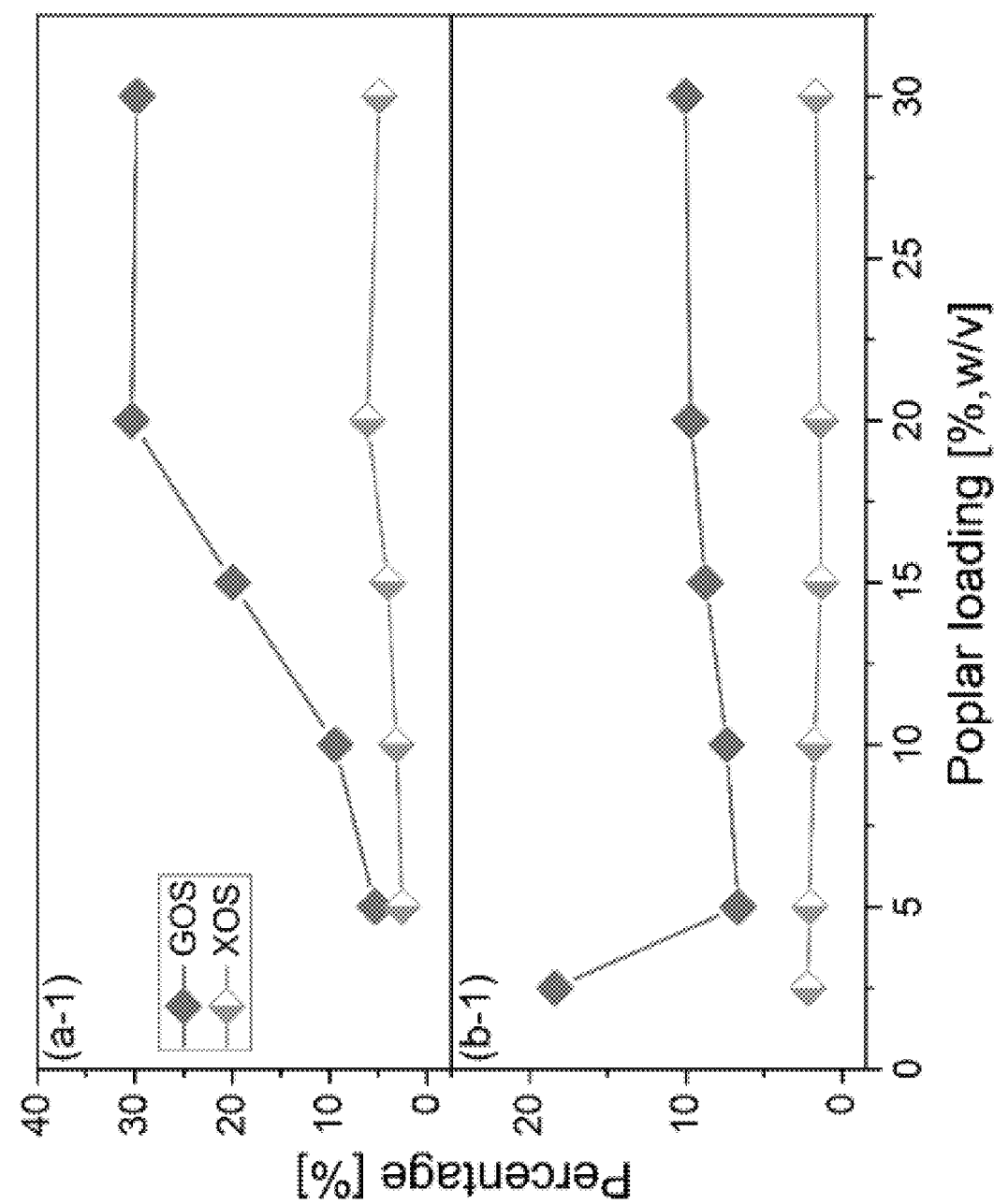

Example 5: Oligosaccharides formed During the Saccharification of Poplar in ALBTH Compared to other systems for lignocellulose saccharification, ALBTH has an excellent performance in dissolving and hydrolyzing cellulose at high biomass solid loading. It was observed that oligosaccharides were formed during the saccharification of biomass, in particular at high solid loading. The yield of the oligosaccharides during the saccharification of poplar in ALBTH was investigated at varied substrate loadings, as shown in FIG. 8A-C. Two strategies were employed in order to maximize the yield of the aqueous soluble oligosaccharides.

In the first strategy, the acid concentration in ALBTH was kept constant at 40 mM, while the solid loading of poplar was varied. As shown in FIG. 8A ((a) and (a-1)), the yield of glucose decreased from 36.9% to 9.4% when solid loading was increased from 5% to 30% (w/v). Much less glucose was released from poplar at higher solid loading. The liquefaction of the biomass became slow with the polar loading and took to 30 min at 30% (w/v) loading. Interestingly, the insoluble residue after the saccharification did proportionally increase with the biomass loading. For example, the residue only slightly increased from 21.4% to 24.9% when poplar loading was elevated from 5% to 20% (w/v). Since the poplar contained 21.5% lignin and 1.8% 95%-ethanol extractives, which both were insoluble in ALBTH, it is safe to assume that the unhydrolyzed or undissolved cellulose in the IR fraction was less than 3%. This observation implied that most of the cellulose in poplar was hydrolyzed into soluble products including glucose and gluco-oligosaccharides (GlOSs). The content of the oligosaccharides varied with the biomass loading. For example, the GlOS yield increased from 5.4 to 30.3% when the poplar loading was elevated from 5% up to 20% (w/v). If only taking cellulose fraction (46.9% in poplar) into consideration, the yield of GlOSs based on cellulose reached up to 64.6%. In addition to cellulose, there was 14.5% xylan in poplar. In the process of poplar saccharification with 40 mM HCl, the yield of xylose did not change significantly around ~10% when the biomass loading increased from 5% (w/v) to 30% (w/v). Reducing poplar loading from 15% to 5% did not favor the yield of xylose. This observation was slightly different from glucose yield. It is known that xylan is more vulnerable to acid catalyzed hydrolysis due to its short chain length and amorphous structure. The slightly lower yield of xylose at low biomass loading was likely not ascribed to the incomplete hydrolysis of xylan, but to the further degradation of xylose to furfural. HMF and furfural are major degradation products from acid catalyzed dehydration of hexoses and pentoses, respectively. Approximately 1.3% HMF and 1.9% furfural were detected at 5% (w/v) poplar loading, respectively. Their yields decreased to 0.1% and 0.3%, respectively, when the poplar loading was elevated to 30% (w/v). The reason was that at constant acid (catalyst) concentration, the ratio of the acid to the substrate (poplar) decreased with the poplar loading, which slowed down the hydrolysis and dehydration reactions. This explained why the yields of monosaccharides and furans were lower at high substrate loadings.

In the second strategy, poplar saccharification was conducted at a constant acid to poplar ratio (0.65 wt %, HCl/poplar). This strategy allowed the concentration of acid to increase proportionally with the substrate loading (higher acid concentration at elevated poplar loading). The yield of glucose reached the maximum (36.7%) at 5% (w/v) poplar loading and then started decreasing and dropped to 25.9% at 30% (w/v) loading (FIG. 8B: (b) and (b-1)). This appeared to be similar to that in the first strategy above, but cellulose was more extensively hydrolyzed here. It was observed that the liquefaction was faster, taking less than 3.5 min even at 30% (w/v) poplar loading. The results suggested that sufficient acid loading was essential to ensure the fast liquefaction of the biomass and extensive hydrolysis of cellulose. Yield of the oligosaccharides from cellulose increased from 6.7% to 10.0% when poplar loading was elevated from 5% (w/v) to 30% (w/v), but the overall yield was nearly 2-3 folders lower than those in the case of constant 40 mM of HCl above in strategy one. However, the low yield of oligosaccharides did not turn out as high yield of glucose but led to undesired side-products. High HCl concentration (≥120 mM) resulted in more HMF and furfural (over 1.3% and 2.0%, respectively). In addition, the insoluble residues turned to black color and increased up to 33% of the initial poplar loading. More black residues (known as humins) were observed, resulting from the acid catalyzed condensation of furan compounds and monosaccharides.[14] The results indicated that increased acid concentration with poplar loading could effectively shorten liquefaction time and improve the hydrolysis efficiency but meanwhile lead to reduced oligosaccharide yield and more sugar degradation products.

Figure 9:
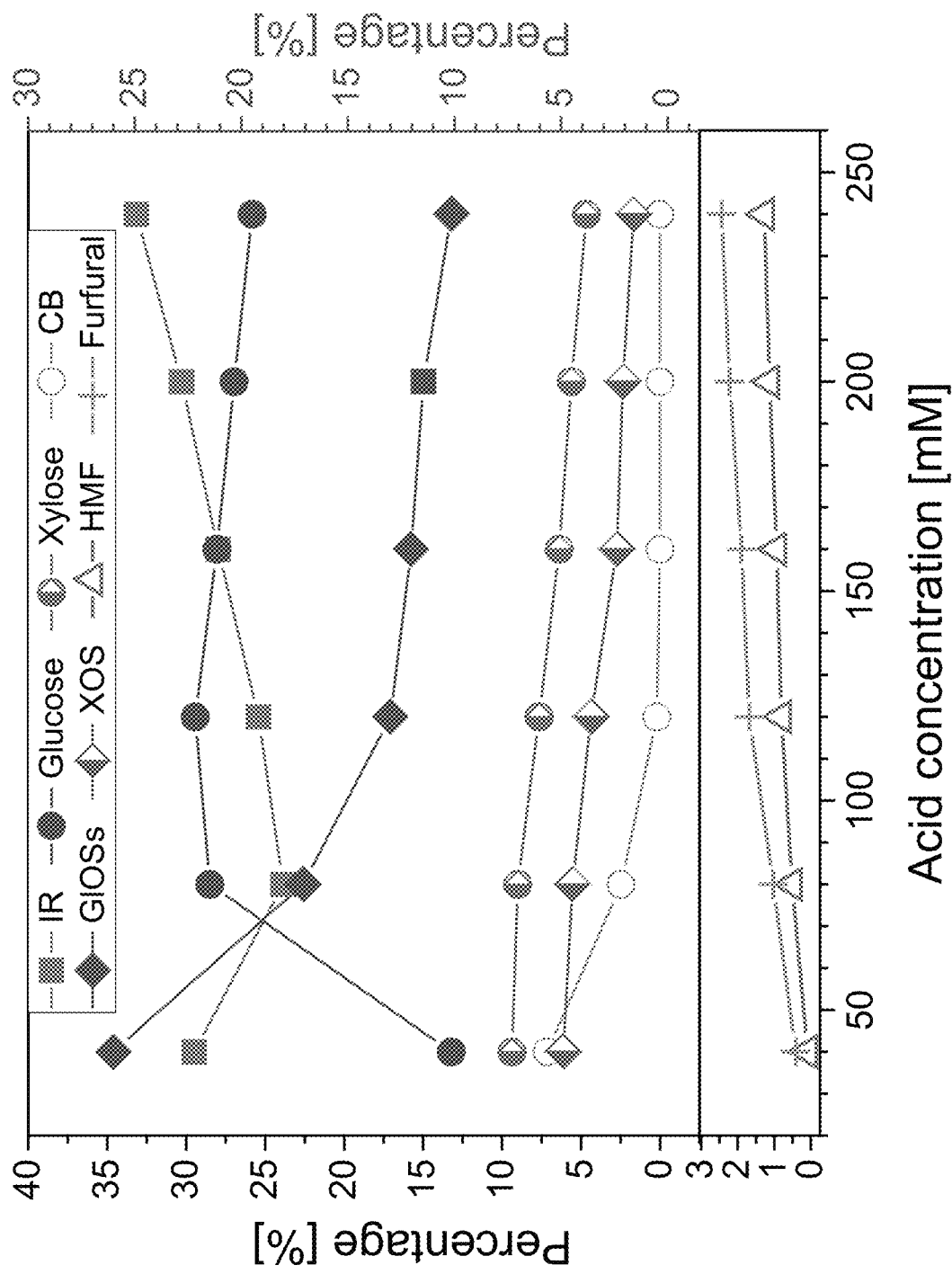
FIG. 9 is a graph showing saccharification of poplar at 30% (w/v) loading in ALBTH with varied acid concentration for production of aqueous soluble monosaccharides and oligosaccharides at 110° C.

In a batch reaction, it was found that 30% (w/v) poplar was the maximum loading at which homogeneous saccharification could be conducted. At higher poplar loading, not all poplar could be wetted with ALBTH even after 1-h sonification. As a result, it was difficult to achieve uniform liquefaction and saccharification of the poplar. Since acid concentration in ALBTH is crucial to the hydrolysis (saccharification) of poplar and end products, saccharification at 30% (w/v) loading was further investigated with varying the acid concentration from 40 to 240 mM. The IR yield initially decreased to 23.9% at 80 mM HCl concentration and then increased to 33.2% at 240 mM HCl (FIG. 9). At low acid concentration, the decrease of IR yield was due to the hydrolysis of cellulose, which was consistent with the increased glucose yield. The increased IR yield at high HCl concentration was attributed to the acid catalyzed formation of the sugar degradation products, as discussed above. With 120 mM HCl, glucose yield was 29.4%, equivalent to 63% of the cellulose in poplar. When the acid concentration was higher than 120 mM, the yield of glucose and xylose started leveling off. It was observed that GlOS yields dropped sharply from 26.0% at 40 mM HCl to 13.0% at 120 mM HCl.

Increasing acid concentration could shorten liquefaction time. For example, liquefaction of poplar at 30% (w/v) loading took approximately 30, 8, and 4 min at 40, 80, and 120 mM HCl, respectively. At a concentration of HCl over 120 mM, liquefaction of poplar was achieved within 3.5 min.

Example 6: Fed-Batch Technique to Enhance the Yield of Oligosaccharides

As discussed above, one-time loading of too much biomass could cause mixing problem. Since the biomass could be quickly liquefied in the ALBTH system, the fed-batch technique was adapted to elevated the total biomass loading, which can be easily achieved in industrial operation.[15] In the fed-batch process, 30% (w/v) of poplar was initially loaded. After 5 min when the first batch of poplar was liquefied, 10% (w/v) more poplar was added. Then, 5% (w/v) more poplar was added every 5 min until 60% (w/v) total poplar loading was achieved at 25 min. It was feasible to reach a solid loading of poplar as high as 80% (30%+10%+10%+10%+10%+10%, w/v) within 60 min. Since lignin fraction was insoluble during the saccharification process, the accumulated lignin at the ultra-high biomass loading (80%, w/v) eventually impaired the solvent mobility and thereby no more poplar could be added.

Figure 10A:
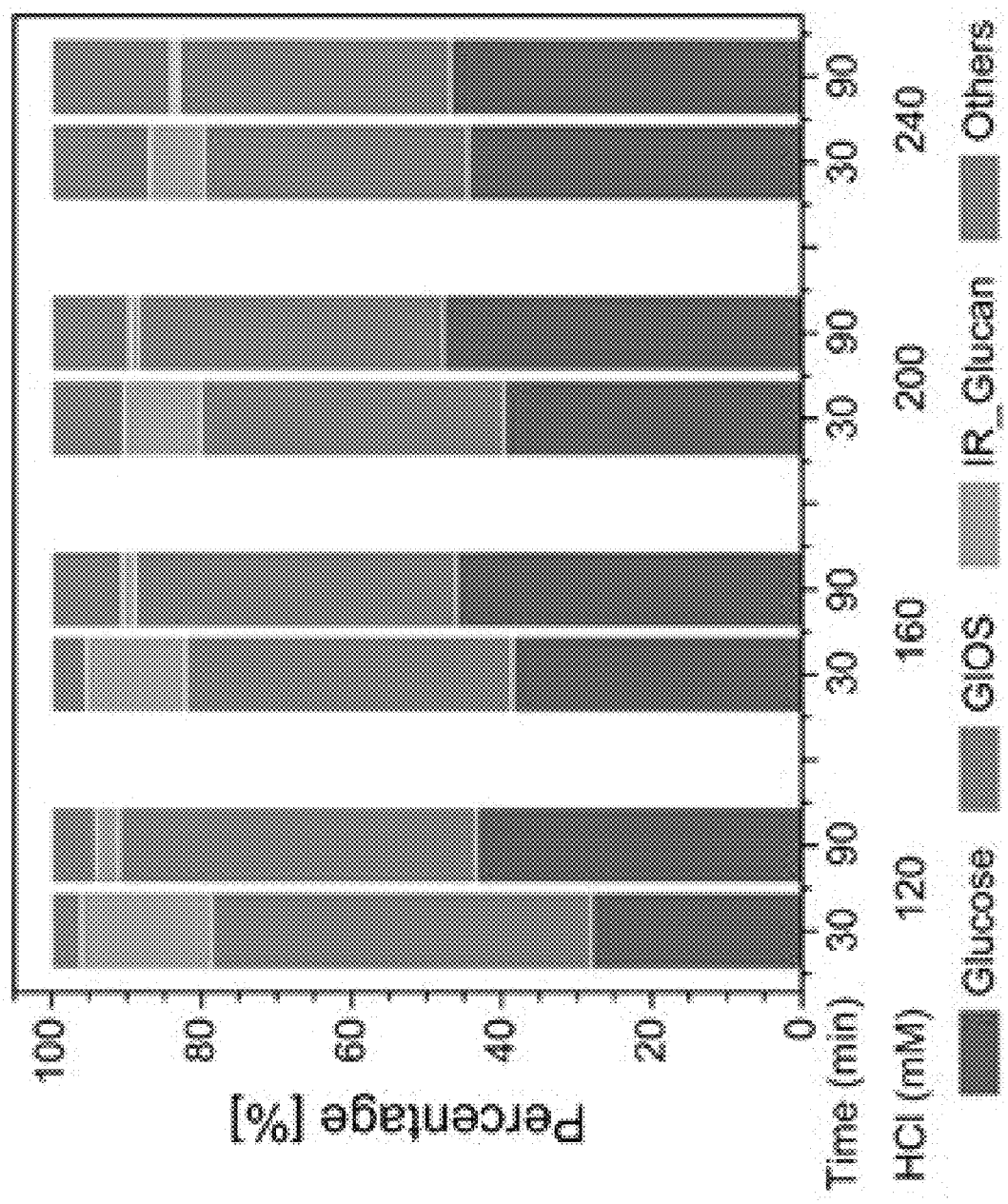
FIGS. 10A-10B are graphs showing distribution of carbohydrate fractions from ALBTH saccharification of poplar (A. glucan and B. xylan) using a fed-batch technique to 60% (w/v) loading at 110° C. (Gluose/Xylose and GlOS/XOS denote the fractions of glucose/xylose and GlOS/XOS in the hydrolysates; IR_Glucan/IR_Xylan denotes the insoluble glucan/xylan fractions in the insoluble residues; and Others represents other components including sugar degradation by-products, such as HMF, furfural, humins, etc.)
Figure 10B:
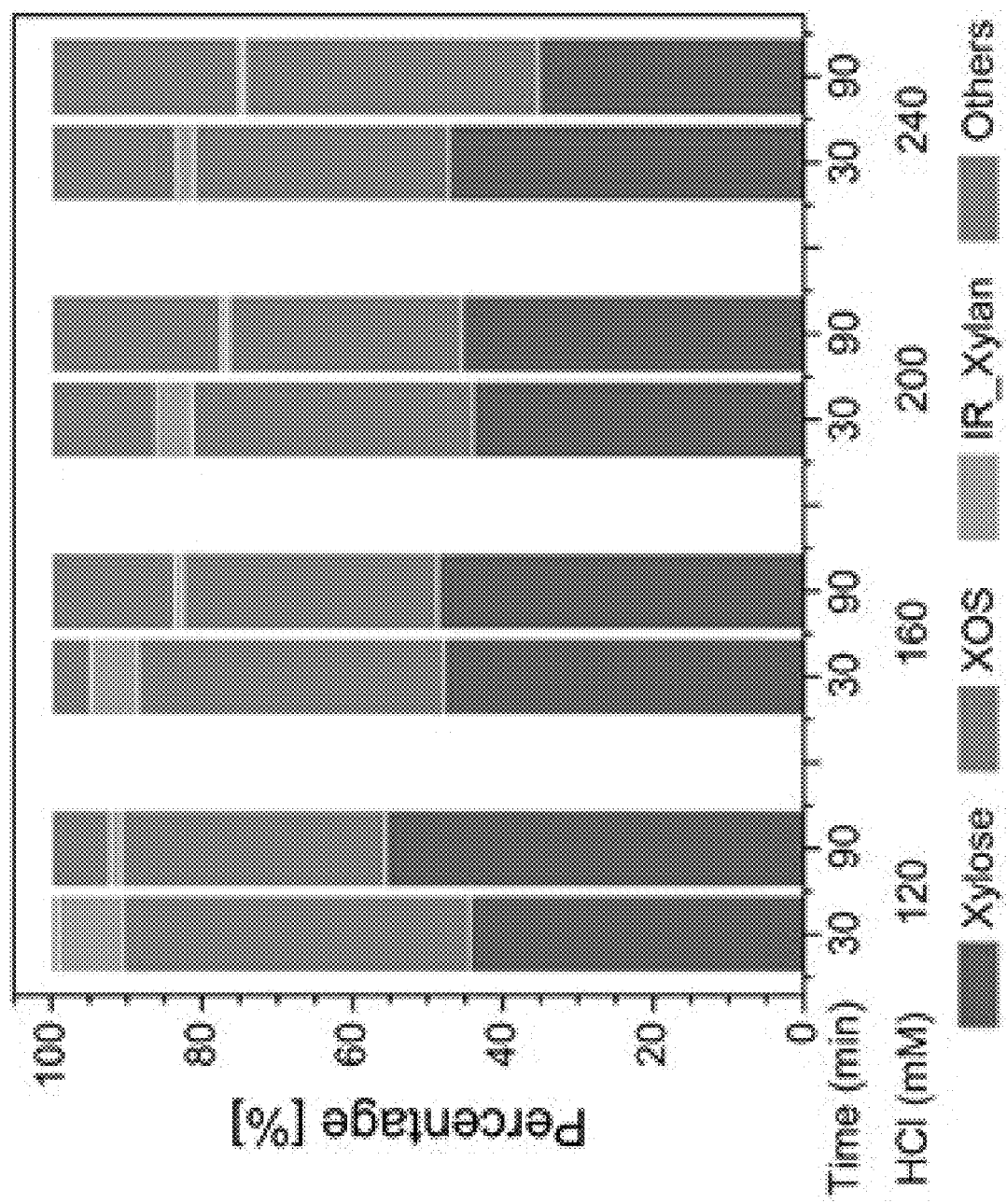

The saccharification of poplar went on smoothly at 60% (w/v) poplar loading. The mass balance and product distribution during the saccharification of poplar at 60% (w/v) loading in ALBTH under different reaction times (30 and 90 min) and acid (HCl) concentrations (120-240 mM) are summarized in FIGS. 10A-10B. After 30-min saccharification at 120 mM HCl, 78.7% glucan was hydrolyzed to 28.1% glucose and 50.6% GlOSs, while 90.5% xylan was hydrolyzed to 44.3% xylose and 46.2% XOSs. The formation of oligosaccharides was more favorable from glucan (oligomer to monomer ratio (O/M)=1.80) compared to that from xylan (O/M=1.04). There were still 17.4% of glucan and 8.7% xylan retained in IR fraction. These results suggested that xylan was more vulnerable to hydrolysis than glucan. Formation of sugar degradation productions was minor (less than 4% of the total carbohydrates) at 30 min. Extending the reaction time to 90 min, hydrolysis of glucan to glucose increased to 43.4%, while residue glucan in IR decreased to 3.0%. GlOSs yield was barely affected by the extended reaction. In summary, up to 91.0% glucan and 90.7% xylan were conversion to aqueous soluble mono- and oligosaccharides in ALBTH with 60% (w/v) poplar loading at 120 mM HCl and 110° C. for 90 min, which include 43.4% glucose and 47.6% GlOSs from cellulose and 55.6% xylose and 35.1% XOSs from xylan, respectively. This appears to be the maximum saccharification efficiency and total sugar recovery to be reported at such high substrate loading under mild reaction conditions.

Increasing the initial HCl concentration for the fed-batch experiment elevated the yield of monosaccharides but dwindled the yield of the oligosaccharides. In addition, high acid concentration enhanced the formation of sugar degradation products. For example, the degradation products were 2.6 times more at 240 mM HCl than at 120 mM. These results suggested that extending the reaction time at a relative low acid concentration was preferable for maximize overall yield of the aqueous soluble mono- and oligosaccharides with limited side products.

The above experiments, in particular those at high poplar loading, demonstrated that oligosaccharides could be produced from poplar via controlled hydrolysis in the ALBTH. For example, at 30% (w/v) poplar loading, O/M of hydrolysis products was in ranges of 0.39-0.60 for those from glucan and 0.34-0.52 from xylan, respectively. At 60% (w/v) loading, the ranges of O/M increased to 0.78-1.10 from glucan and 0.63-1.10 from xylan, respectively. These results indicated that the oligosaccharides were preferentially formed at higher substrate loading.

Example 7: Structures of the Oligosaccharides

Figure 11A:
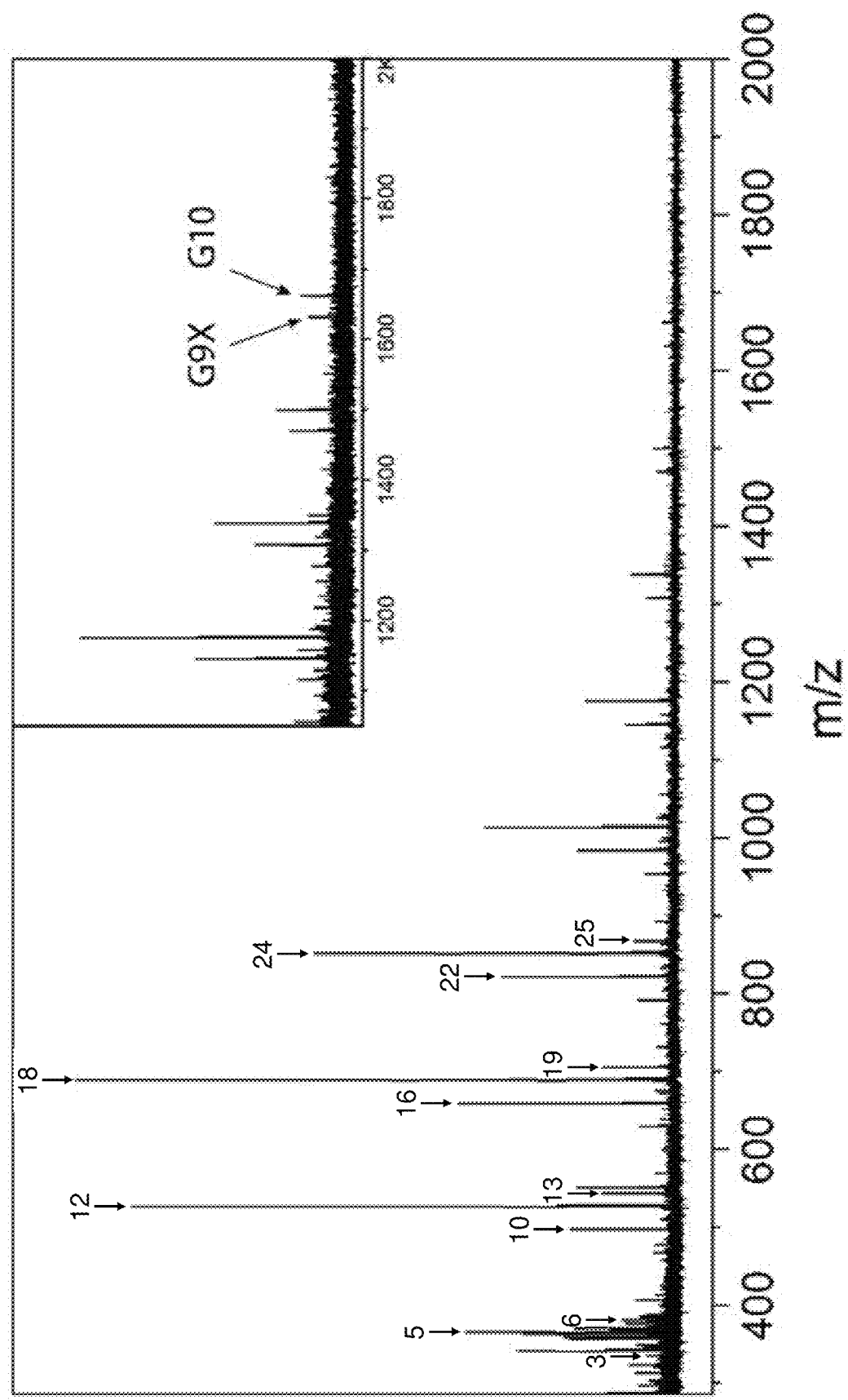
Figure 11B:
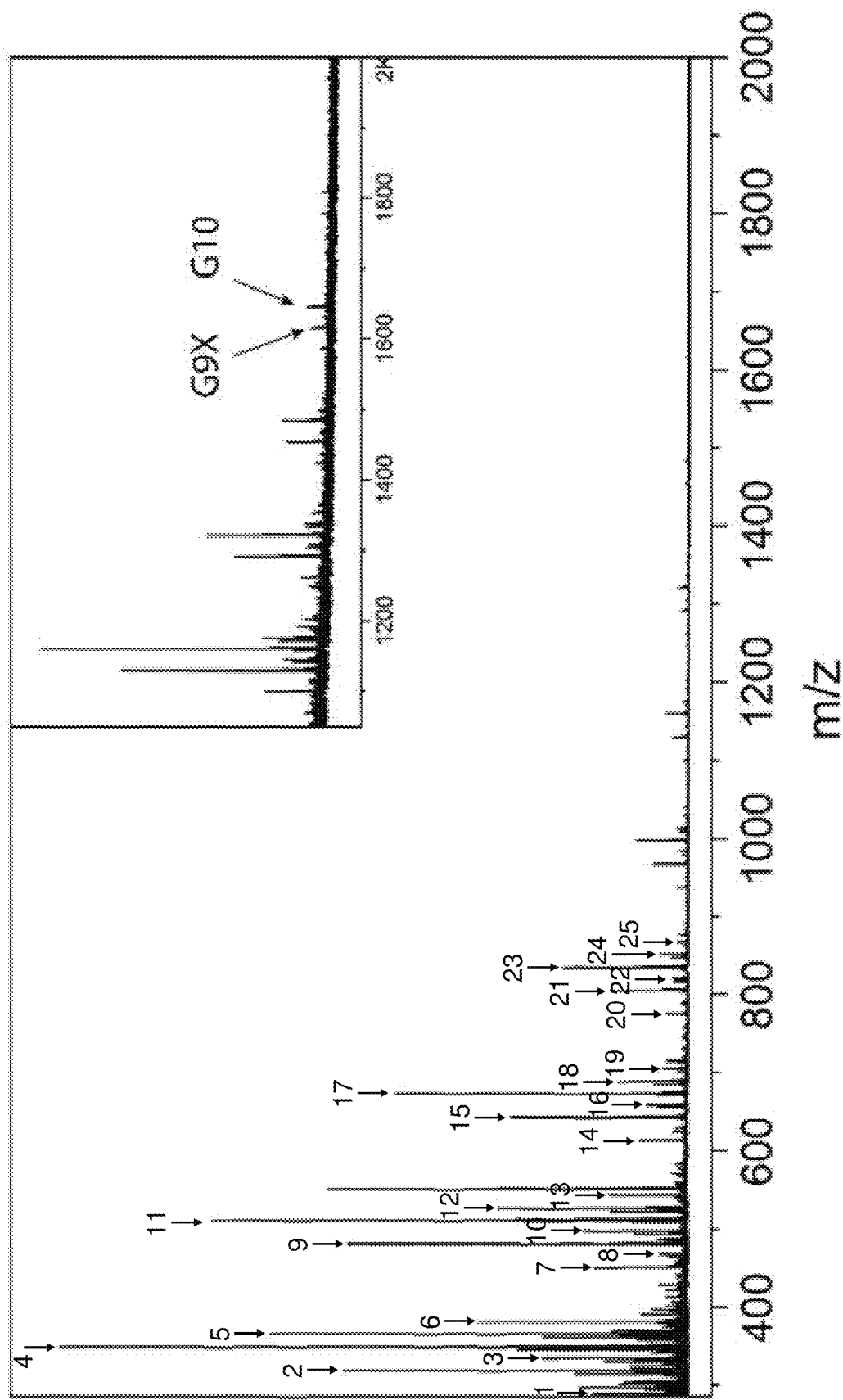

In order to understand the structure of the oligosaccharides and their formation mechanism in the process of poplar saccharification in the ALBTH system, the oligosaccharides were separated from the hydrolysate and purified by precipitation in anti-solvent (ethanol/acetone) followed by freeze-drying. The resultant purified oligosaccharides were in form of white powder. The molecular weight distribution of the oligosaccharides was investigated using MALDI-TOF MS, as illustrated in FIG. 11. It was found that the oligosaccharides were composed of not only glucose units but also xylose units, suggesting that the oligosaccharides were not simply the products from incomplete hydrolysis of cellulose, and the xylose units from hemicellulose hydrolysis were bond to the oligosaccharides through glycosidic bonds. The mass peaks of oligosaccharide metal adducts below 900 Da could be assigned using the formula of GnXm-M [m/z=18+162n+132m+7($Li^+$)/23($Na^+$)/39($K^+$)]. The letters n and m represent the number of anhydrous glucose (G) and xylose (X) units in the oligosaccharides, respectively. M stands for the metal added to the oligosaccharides, including $Li^+$, $Na^+$, and $K^+$. Under a relative mild condition (120 mM HCl and 60% (w/v) poplar loading for 30 min), the resultant oligosaccharides were composed of either exclusively anhydrous glucose units (Gn-M) or anhydrous glucose units together with only one anhydrous xylose unit (GnX-M). This result verified that xylose was bond to GlOSs in the process of ALBTH saccharification. In the MS spectra, XOSs adduct peaks were not observed, but the formation of XOSs was confirmed via the post-hydrolysis analysis of the hydrolysate. The absence of XOSs peaks on MS spectra was probably because the XOSs were not recovered as GlOSs during the precipitation in the anti-solvent due to the XOSs' high solubility in the anti-solvent. In addition, the glycosylation reaction from xylose at 100% (w/v) loading verified the formation of XOSs, but the majority of the XOSs were lost during the anti-solvent precipitation. The DP range of the oligosaccharides was 2-10, which agreed with the observation from other studies that the oligosaccharides with DP>10 were marginally soluble in an aqueous solution.[16] For the oligosaccharides from 30-min saccharification of poplar in ALBTH, the most intense peaks were the oligosaccharides with DP 3-5. When the saccharification time was extended to 90 min, the most intense peak was from disaccharide. In addition, the intensity of the mass peaks decreased with the DP, suggestion that extended hydrolysis let to more low-molecular-weight oligosaccharides. It is known that both the molar concentration and the ionization efficiency of the molecules significantly affect the intensity of the resultant MS peaks.[17] Since the ionization efficiency of larger oligosaccharides molecules (DP 3-5) was not as high as that of smaller disaccharides, it was safe to deduce that the oligosaccharides from short time saccharification should contain more high DP fractions than those from the extended saccharification. Interestingly, GnX2-M (GlOSs containing two anhydrous xylose units) was detected in the sample from 90-min saccharification, but not in that from the 30-min saccharification (FIG. 11A).

The glycosidic linkages in the oligosaccharides were identified using 2D HSQC NMR. It is commonly accepted that oligosaccharides are intermediates in the process of polysaccharide hydrolysis to monosaccharides under the acidic conditions. Since glucose and xylose units are exclusively linked via β-1,4-glycosidic bonds in the chains of cellulose and xylan, respectively, the oligosaccharides from partial hydrolysis of the polysaccharides would only have the β-1,4-glycosidic bonds.

The 2D HSQC NMR spectrum of the oligosaccharides from the saccharification of poplar in ALBTH system was obtained. Although most of $^1$H-$^{13}$C correlation signals at the C2, C3, C4, and C6 positions of glucose and xylose units overlapped in the region of 3.10-4.00 ppm in the $^1$H dimension and 62.0-82.4 ppm in the $^{13}$C dimension, assignments of the glycosidic linkages could be made using the distinguishable anomeric (C1) correlation based on the assignments of disaccharide standards and the reported oligosaccharides.[18] Presence of β-1,4-linkages in the oligosaccharides was confirmed from $^1$H-$^{13}$C correlation of the anomeric non-reducing C1 at 4.51/105.3 ppm. Surprisingly, other glycosidic linkages that do not exist in original biomass were identified, including α/β-1,1-, α-1,2-, α/β-1, 3-, α-1,4-, and α/β-1,6-glycosic bonds. This suggested that not only hydrolysis but also glycosylation occurred during the saccharification of poplar in the ALBTH system. In other words, the monosaccharides (glucose and xylose) from the cellulose and hemicellulose hydrolysis condensed or bound to the oligosaccharide intermediates, leading to the formation of the new glycosidic bonds. Since there was overlap between the anomeric $^1$H-$^{13}$C correlation of β-1,6 glycosylic linkages on the non-reducing end and the β-1,4-glycosylic linkages, the characteristic correlation contours at 3.86/71.5 ppm and 4.18/71.5 ppm from the CH2 in the C6 position of β-1,6-glycosylic linkage and 3.65/81.1 ppm from the C—H in the C4 position of β-1,4 glycosidic linkages provided additional proofs of the presence of β-1,6 glycosidic linkages. The correlation signal at 4.45/104.4 ppm from anomeric xylose units linked by β-1,4-glycosidic bond was not identified, but the anomeric correlation between xylose and glucose glycosylic linkages was resolved, confirming that xylose was added to the oligosaccharides. This observation was in agreement with the MALDI-TOF MS result above. Since these new glycosylic linkages except do not exist in the original lignocellulose, they must be formed during the acid catalyzed saccharification process in ALBTH system via intermolecular glycosylation reaction. In summary, based on the evidences from the chromatographic analysis of the hydrolysates, MALDI-TOF MS, and HSQC NMR characterization of the oligosaccharides, it could be concluded that both hydrolysis of polysaccharides and the glycosylation reactions between monosaccharides/oligosaccharides occurred in the process of lignocellulose saccharification in ALBTH system, which led to the oligosaccharides that contain new glycosidic bonds that do not exist in cellulose and xylan. This process provided a new approach to synthesize the oligosaccharides with varied glycosidic linkages from inexpensive lignocellulose feedstocks.

Example 8: Elucidation and Confirmation of Formation Mechanisms of the Oligosaccharides To understand the formation of the oligosaccharides during the saccharification of poplar in the ALBTH system, cellulose was used as model substrate to elucidate the formation mechanism of the oligosaccharides, which eliminated the interference from lignin and hemicellulose fractions. It was found in our previous studies that the ALBTH system was capable of disrupting the inter- and intramolecular hydrogen bonds in cellulose and thereby dissolving cellulose.[10, 11] The dissolved cellulose was vulnerable to be hydrolyzed by the acid catalyst to break the β-1,4-glycosylic bonds, resulting in mono- and oligosaccharides. Therefore, the hydrolysis of cellulose in ALBTH should be a homogeneous process. Compared to the heterogeneous hydrolysis process in which production of monosaccharides is more favorable, the homogenous process under mild conditions would favor oligosaccharide production.[19, 20]

GlOSs Formation During Cellulose Hydrolysis in ALBTH

Figure 13:
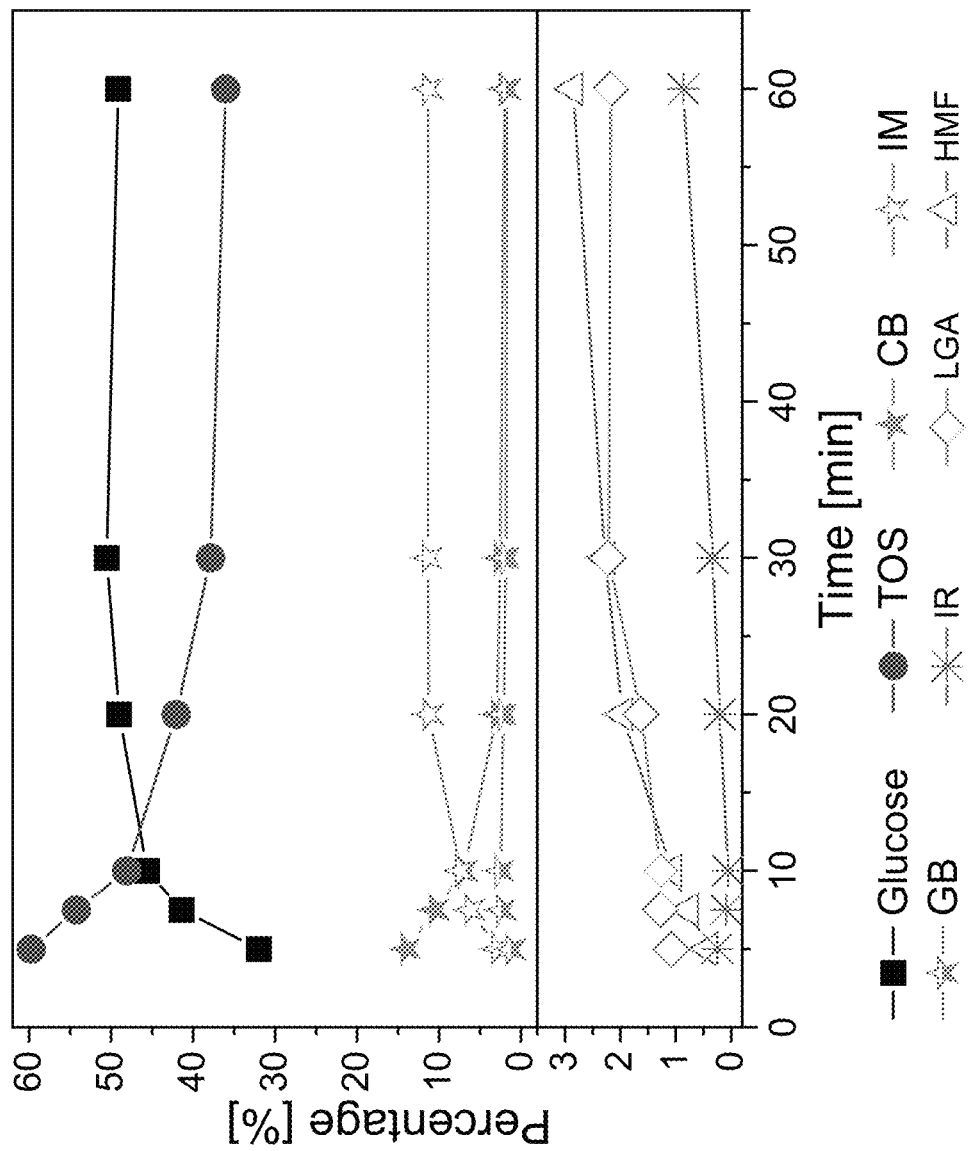
FIG. 13 is a graph showing the homogenous hydrolysis of cellulose at high substrate loading (30%) in ALBTH (40 mM HCl) to yield GlOSs as well as glucose and glucose degradation products as a function of ALBTH hydrolysis time at 110° C. (Note: The yields were based on % anhydrous glucose unit (AGU) in cellulose expect IR yield which was based on wt % of cellulose.)
Figure 14:
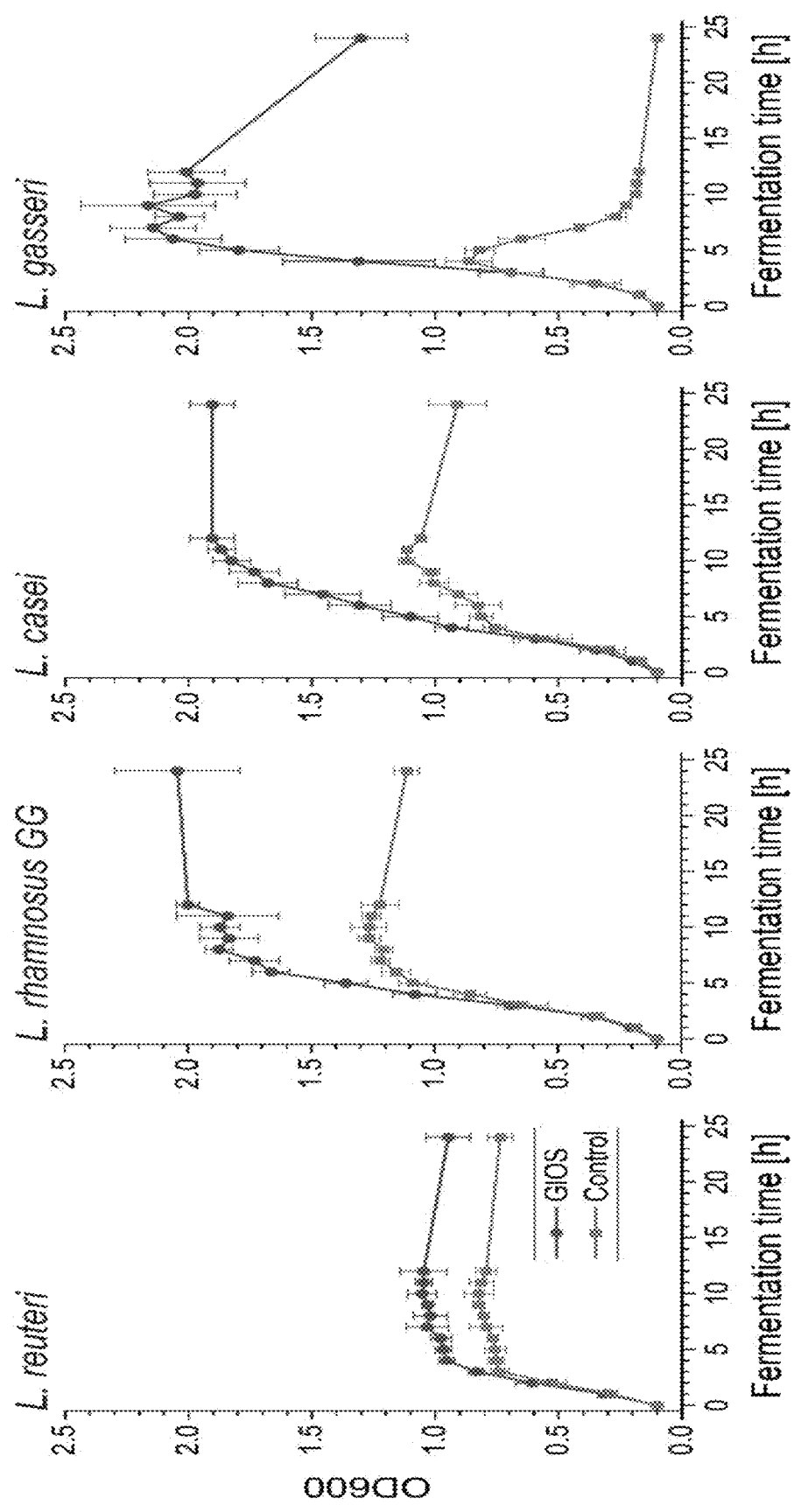
FIG. 14 is graph showing growth curves after 24 h anaerobic incubation at 37° C. of *L. reuteri* (ATCC 6475), *L. rhamnosus* GG, *L. casei* BFLM 218, *L. gasseri* ATCC 33323 with GlOS (9.5 g/L)+glucose (0.5 g/L) or minimal glucose (0.5 g/L) as the carbon source.

Cellulose substrate (Avicel) is insoluble in water and ALBTH at ambient temperature and has a high water retention value. It was found that 30% cellulose loading was a critical point where cellulose could be fully wetted by ALBTH, but the solvent was completely adsorbed (no free solvent), which was the maximum cellulose loading at which batch hydrolysis could still proceed. As discussed above, the maximum substrate loading for batch saccharification of poplar was 30% as well. However, since cellulose content in poplar was only 46.9%, the authentic cellulose loading for poplar was roughly only half of that for Avicel. When elevating saccharification temperature to 110° C., cellulose was liquefied in ALBTH within 2 min and became a fully transparent solution in 5 min. As shown in FIG. 13, less than 0.3% insoluble residues were left after 5 min, suggesting that cellulose was almost quantitatively dissolved. Up to 59.7% GlOSs and 32.0% glucose were detected in the hydrolysate (O/M=1.87). As a comparison, hydrolysis of cellulose in organic solvents (such as GVL/water, 9:1, v/v) yielded less than 25% of GlOSs with O/M ratio less than 0.6.[8] In another prevalent saccharification process (supercritical water hydrolysis), the yield of GlOSs could reached up to 50% at extremely high temperature (360° C.) for 0.5 s, while the yield of total aqueous soluble mono- and oligosaccharides were less than 70% with a significant amount of side-products.[9] As far as we know, the mechanocatalytic depolymerization of cellulose was the only approach that could reach a yield of GlOSs higher than 60%, which was possibly attributed to the nature of the solid state reaction.[16] However, it was very challenging to scale-up the mechnocatalytic process because extensive ball milling with concentrated $H_2SO_4$ was involved.[21]

Further extending the hydrolysis time, the yield of GlOSs gradually reduced from 48.1% at 10 min to 36.0% at 60 min, while the yield of glucose increased to 49.0% at 20 min and then leveled off. The increase in glucose yield at the initial stage was ascribed to the hydrolysis of cellulose to glucose. Using cellobiose (the β-1,4-glycosidically linked disaccharide) as an indicator for hydrolysis of cellulose, cellobiose yield was dwindling with hydrolysis time from 14.0% to 2.0%. However, extending the reaction time did not result in a higher glucose yield, which was due to the glycosylation reactions of glucose leading to GlOSs. Isomaltose and gentiobiose (the α/β-1,6-glycosidically linked disaccharides) were the major glycosylation products from glucose in ALBTH. Both do not exist in original cellulose chain, suggesting that the glycosylation reaction occurred during the cellulose hydrolysis in the ALBTH system. The yields of isomaltose and gentiobiose increased with reaction time upto 11.3% and 1.8%, respectively. The yield of gentiobiose started declining slightly after reaching a maximum at 10 min, while that of isomaltose kept increasing with time. This was in agreement with our previous observation that formation of α-1,6-linkages was thermodynamically favorable while formation of β-1,6-glycosylic linkages was kinetically favorable.

It is known that sugar degradation reactions were almost inevitable under acidic condition. The formation of the side-products was insignificant in the ALBTH system, compared to that in other acidic hydrolysis processes. LGA (via reversible intra-molecular dehydration) and HMF (irreversible dehydration reaction) were detected at a yield of 1.1-2.2% and 0.4-2.9%, respectively, at extended reaction time. In addition, a negligible amount of humins (black floccules, less than 0.9% in yield) was detected after extensive hydrolysis. It was a result of degradation and condensation of HMF and monosaccharides.

The results above indicated that cellulose was homogenously hydrolyzed in the ALBTH system, and meanwhile the glycosylation reaction leading to formation of GlOSs between cellulose hydrolysis products (glucose and oligosaccharides) occurred. In order to maximize the GlOSs yield, the reaction conditions were optimized (Table 6). At low reaction temperature (90° C.), dissolution and hydrolysis of cellulose in ALBTH was limited. Cellulose liquefaction took up to 60 min. After 90 min, there was still up to 12.1% solid cellulose that was not dissolved and hydrolyzed. Yields of glucose and GlOSs were 29.3 and 52.9%, respectively. Under this condition, GlOSs were formed primarily from the incomplete hydrolysis of cellulose. Cellobiose yield was 9.8%. Only a small amount of isomaltose (2.8%) and gentiobiose (0.8%) were generated, suggesting that the acid catalyzed glycosylation was minor. Increasing the reaction temperature to 100° C., the liquefaction time was shortened to about 12 min with 20 mM HCl and about 7 min with 40 mM HCl, respectively. After 10 min hydrolysis, 66.8% GlOSs and 28.2% glucose were produced along with 4.8% of insoluble cellulose residue. Further elevation of temperature to 110° C. with reduced acid concentration (20 mM) achieved a similar GlOS yield. Increasing acid concentration and extending reaction time at the same reaction temperature favored the hydrolysis of cellulose fraction (IR) and the gluco-oligosaccharides, resulting in more glucose. However, the glucose yield hardly excessed 41%, and more than 50% of the products were in the form of GlOSs. The results suggested that incomplete hydrolysis of cellulose was not exclusively responsible to the GlOS formation, and the glycosylation of glucose from cellulose hydrolysis was the second mechanism of GlOSs formation. HMF yield was positively related to the reaction severity, while formation of LGA was affected primarily by reaction temperature.

TABLE 6

Homogeneous hydrolysis of cellulose in ALBTH at varied temperature, acid concentration and reaction time for production of GlOSs and glucose

| T (° C.) | HCl (mM) | t (min) | Glucose yield (%) | GlOS yield (%) Total | IM | GB | CB | IR (wt %) | LGA yield (%) | HMF yield (%) |
|---|---|---|---|---|---|---|---|---|---|---|
| 90 | 20 | 90 | 29.3 | 52.9 | 2.8 | 0.8 | 9.8 | 12.1 | 0.8 | 0.4 |
| 90 | 40 | 150 | 41.3 | 51.1 | 6.6 | 2.3 | 8.5 | 3.7 | 1.1 | 0.6 |
| 100 | 20 | 20 | 22.3 | 62.9 | 1.2 | 0.3 | 11.4 | 10.9 | 1.6 | 0.2 |
| 100 | 20 | 60 | 33.9 | 58.0 | 3.2 | 1.1 | 10.8 | 3.6 | 2.3 | 0.5 |
| 100 | 40 | 10 | 28.2 | 66.8 | 1.8 | 1.0 | 12.8 | 4.8 | 1.9 | 0.3 |
| 100 | 40 | 20 | 39.2 | 55.3 | 5.1 | 2.1 | 9.3 | 0.5 | 2.5 | 0.6 |
| 110 | 20 | 10 | 29.1 | 64.0 | 1.7 | 0.6 | 13.4 | 2.5 | 2.2 | 0.4 |
| 110 | 20 | 20 | 39.9 | 54.2 | 5.2 | 0.9 | 9.3 | N.D. | 3.1 | 0.8 |

It is intuitive to understand the formation of the oligosaccharides via incomplete hydrolysis of cellulose, but it is ambiguous to comprehend the glycosylation to yield GlOSs during cellulose hydrolysis. In order to elucidate the formation of GlOSs, the following experiment was designed. Since glucose and cellobiose are the hydrolysis products of cellulose, studying their effects on the formation GlOSs by adding glucose and cellobiose in the process of cellulose hydrolysis would be able to provide insights into the glycosylation occurrence. As shown in Table 7, at the same cellulose loading, addition of glucose only slightly increased the yield of GlOSs from 54.2 to 55.4%, but significantly increased the yield of isomaltose and cellobiose, 25% and 27% higher than the control, respectively. In our previous study, it was found that the glycosylation of glucose occurred in the ALBTH system and resulted in GlOSs, but a negligible amount of cellobiose and β-1,4-glycosylic oligomers were formed during the glucose glycosylation. Therefore, it is reasonable to deduce that the cellobiose formed in study was likely from the cellulose hydrolysis not from the condensation of two glucose units. The addition of glucose probably inhibited the hydrolysis of cellobiose, leading to the accumulation of cellobiose in the system.

TABLE 7

Effects of glucose and cellobiose addition on homogenous hydrolysis of cellulose in ALBTH

| T (° C.) | Loading (%) Cell/CB/G | HCl/t (mM/min) | Glucose Yield (%) | GlOS yield (%) Total | IM | GB | CB | IR (wt %) | LGA yield (%) | HMF yield (%) |
|---|---|---|---|---|---|---|---|---|---|---|
| 110 | 30/0/0 | 20/20 | 39.9 | 54.2 | 5.2 | 0.9 | 9.3 | N.D. | 3.1 | 0.8 |
|  | 30/0/10 | 20/20 | 39.6 | 55.4 | 6.5 | 0.8 | 11.8 | 0.4 | 2.8 | 0.8 |
|  | 30/0/0 | 40/10 | 45.6 | 48.1 | 7.4 | 1.2 | 6.6 | N.D. | 1.3 | 1.1 |
|  | 20/10/0 | 40/10 | 49.8 | 44.4 | 8.6 | 1.0 | 5.3 | N.D. | 1.3 | 1.4 |
|  | 20/0/10 | 40/10 | 51.4 | 44.2 | 9.3 | 1.0 | 7.1 | N.D. | 1.4 | 1.5 |
| 130 | 30/0/0 | 40/10 | 53.2 | 36.1 | 8.4 | 0.9 | 0.8 | N.D. | 2.0 | 3.1 |
|  | 20/10/0 | 40/10 | 53.7 | 35.1 | 8.6 | 0.7 | 1.0 | N.D. | 2.1 | 3.6 |
|  | 20/0/10 | 40/10 | 54.3 | 35.5 | 8.6 | 0.8 | 0.9 | N.D. | 1.6 | 3.7 |

Characterization of the GlOSs from Cellulose Hydrolysis

The GlOSs prepared at 30% (w/v) cellulose loading in ALBTH were isolated and purified by the anti-solvent precipitation method and characterized using MALDI-TOF MS and NMR. On the MALDI-TOF MS spectrum, the adduct peaks followed the formula [Gn-M, m/z=18+162n+7(Li$^+$)/23(Na$^+$)/39(K$^+$)], indicating that the GlOSs were composed of only anhydrous glucose units. Compared to the spectrum of the oligosaccharides from poplar, there was no anhydrous xylose unit linked to GlOSs. This observation confirmed that xylose in the poplar oligosaccharides were from the hydrolysis of xylan in poplar. The DP of GlOSs from cellulose was primarily from 2 to 10, although a trace amount of GlOSs with DP up to 16 were detected.

The $^1$H-$^{13}$C HSQC NMR spectrum of GlOSs showed a similar correlation signals to that of the oligosaccharides from poplar, but the xylose related signals were invisible. It was in agreement with the result from MALDI-TOF MS analysis. The identified glycosidic linkages between glucose units in the GlOSs from cellulose were identical to those in the oligosaccharides from poplar.

In order to evaluate the regio- and stereo-information of the glycosidic bonds in the GlOSs, a semi-quantitative HSQC NMR experiment was conducted with a relaxation delay of 10 s. There are several potential factors that could influence the quantitative fashion of the HSQC experiment, including the deviation of coupling constant $^1J_{C-H}$, resonance offset, and relaxation effects (both longitudinal relaxation T1 and transverse relaxation T2).[22, 23] Form the MALDI-TOF MS analysis, the molecular weight of the GlOSs was below 1500 Da, and so the T2 effect was supposed to be insignificant. In addition, it was found that the one bond coupling constants ($^1J_{C-H}$) of the anomeric C1-H1 correlations had little variation (ranging from 158-172 Hz for the $^1J_{C-H}$ of β-anomers, 10-15 Hz higher than that of α-anomers). Therefore, the semi-quantitative estimation of the glycosylic linkages in GlOSs should be reliable by a general hsqcetgpsisp 2.2 program with a sufficient D1 (10 s). As illustrated in the $^1$H-$^{13}$C HSQC NMR spectrum of GlOSs, 48% and 38% of the glycosylic bonds were (1→4) and (1→6) linkages, respectively. The β-anomer was dominant (95%) in the (1→4) linkages, while the α-anomer had a higher selectivity in the (1→6) linkages. Since the β-1,4-glycosidic linkages were exclusively inherited from cellulose and the rest of the glycosidic linkages were newly formed via acid-catalyzed glycosylation reactions, the estimated relative contributions of hydrolysis and glycosylation to the formation of oligosaccharides from cellulose were approximately 45% and 55%, respectively. In terms of assignments of the glycosidic linkages from glycosylation synthesis, the occurrence of the detected linkages followed the order of α-1,6-(32%)>β-1,6-(7%)>α-1,3-(6%)>α-1,2-(4%)>α-1,4-(2%)≈α/β-1,1-(2%)>(3-1,3-(1%). It was reported that the oligosaccharides linked via α-1,6-, β-1,6-, α-1,2-, and α-1,3-glycosylic bonds were of potential prebiotic function.[24-26] Therefore, the oligosaccharides from the controlled hydrolysis of cellulose and lignocellulose are expected to have potential applications as prebiotics.

Example 9 Oligosaccharides Production with ALBTH Process from Softwood and Switchgrass To validate the feasibility of lignocellulose feedstocks other than poplar (a hardwood) for the oligosaccharide production, Douglas fir (D. fir, a softwood) and switchgrass (an energy crop) were applied to ALBTH saccharification at high biomass loading (30%, w/v). The yields of mono- and oligosaccharides are summarized in Table 9. Aqueous soluble oligosaccharides with up to 25.5% yield from the biomass, were extracted from D. fir and switchgrass, similar to poplar. The results indicated that the process of oligosaccharide production in ALBTH could be applicable to different sources of lignocellulose, including hardwood, softwood, and herbaceous biomass. Notably, the liquefaction efficiency varied, as the 30% (w/v) D. fir took less than 10 min, while poplar required approximate 30 min for liquefaction in ALBTH with 40 mM HCl. Under the identical condition, switchgrass even failed to achieve liquefaction after 60 min as a neutral pH was detected, indicating that the acids was consumed/neutralized by the basic ash in switchgrass. Increasing the acid concentration to 120 mM, liquefaction of switchgrass could also be achieved in 10 min. It was suggested that the parameters of ALBTH saccharification for GlOS production need further optimization according to different types of lignocellulose.

TABLE 9

Yields of mono- and oligosaccharides from various biomass in ALBTH

| Biomass | | Poplar | D. fir$^1$ | D. fir$^2$ | Switchgrass |
|---|---|---|---|---|---|
| IR (wt %) | | 32.0 | 31.6 | 27.4 | 24.6 |
| Arab yield (%) | DP = 1 | 0.2 | 1.3 | 1.6 | 1.4 |
| | DP ≥ 2 | 0.1 | 0.4 | 0.4 | 0.6 |
| Gal yield (%) | DP = 1 | 0.3 | 4.8 | 5.0 | 0.7 |
| | DP ≥ 2 | 0.2 | 1.7 | 2.3 | 0.2 |
| Glu yield (%) | DP = 1 | 9.4 | 25.9 | 22.3 | 17.0 |
| | DP ≥ 2 | 29.8 | 10.0 | 18.2 | 17.9 |
| Xyl yield (%) | DP = 1 | 9.6 | 2.6 | 3.3 | 15.5 |
| | DP ≥ 2 | 4.9 | 0.8 | 1.4 | 4.3 |
| Man yield (%) | DP = 1 | n.d. | 4.2 | 5.0 | n.d. |
| | DP ≥ 2 | n.d. | 1.6 | 3.2 | n.d. |
| HMF yield (%) | | 0.1 | 1.2 | 0.4 | 0.5 |
| Furfural yield (%) | | 0.3 | 0.8 | 1.2 | 0.3 |

Other conditions: The reactions were conducted at 30% (w/v) biomass loading and 110° C. in 60% LiBr.

The HCl concentration were 40 mM for poplar and D. fir$^2$, and 120 mM for D. fir$^1$ and switchgrass.

IR, arab, gal, glu, xyl, and man denoted insoluble residue, arabinose/arabinan, galactgose/galactan, glucose/glucan, xylose/xylan, and mannose/mannan.

Example 10: Oligosaccharides from Different Monosaccharides Via Glycosylation in ALBTH System The acid catalyzed glycosylation was assumed to involve the oxocarbenium as the glycosyl donor and active hydroxyls as the glycosyl acceptors. In addition to glucose, other sugars including arabinose, galactose, xylose, etc. could provide both the oxocarbenium and the active hydroxyls. The synthesis of the oligosaccharides via glycosylation reaction in ALBTH from various sugars was preliminarily investigated, and the results are listed in Table 10. The results suggested that oligosaccharides could be produced in ALBTH from different monosaccharides with varied yields. It seemed that hexo-oligosaccharide had slightly higher yield than pento-oligosaccharides.

TABLE 10

Preliminary investigation of monosaccharide conversion from glycosylation of arabinose, galactose, glucose, and xylose in ALBTH at 110° C. for 10 min

| Loading (%, w/v) | | | | Conversion (%) | | | |
|---|---|---|---|---|---|---|---|
| Arabinose | Galactose | Glucose | Xylose | Arabinose | Galactose | Glucose | Xylose |
|  | 20 | 20 |  |  | 57.1 | 55.8 |  |
|  | 100 |  |  |  | 64.9 |  |  |
|  | 40 |  |  |  | 48.3 |  |  |
|  |  | 27 | 13 |  |  | 43.0 | 40.5 |
|  |  |  | 40 |  |  |  | 40.7 |
| 20 | 20 | 20 | 20 | 54.1 | 61.1 | 59.4 | 56.2 |

Example 11: Synthesis of Oligosaccharides Via Glycosylation in Different Molten Salt Hydrate Systems Various molten salt hydrate systems were tested as the media for production of oligosaccharides from glucose. In the preliminary test, the divalent metal salts were paired by 6 hydrates, and the monovalent metal salts were paired by 3 hydrates. In the case of NaBr.3H$_2$O and MgCl$_2$.6H$_2$O, full dissolution at room temperature wasn't successful, so extra 3 hydrates were supplemented. As shown in Table 11, all the molten salt hydrate systems including NaBr.6H$_2$O, LiCl.3H$_2$O, LiBr.3H$_2$O, CaCl$_2$.6H$_2$O, and CaBr$_2$.6H$_2$O exhibited the potential capacity as reaction medium of producing gluco-oligosaccharide (GlOS) from glucose with the yields ranging from 19-42%. Paired by the same anions (either chloride or bromide), the lithium salts resulted in higher GlOS yields than the sodium and calcium salts. The comparison of the GlOS yields between LiCl.3H$_2$O vs LiBr$_3$H$_2$O and CaCl$_2$.6H$_2$O vs CaBr$_2$.6H$_2$O revealed that bromide was more efficient than chloride to promote the glycosylation reactions. As a result, LiBr.3H$_2$O led to the highest GlOS yield under the investigated conditions. It was found that the yield of GlOS was negligible in ZnCl$_2$.6H$_2$O. Instead, a small amount of fructose was produced, indicating that ZnCl$_2$ might favor the glucose isomerization reaction under the acidic condition.

TABLE 11

Comparison of GlOS production in various MSH systems

| MSH | Conversion (%) Glucose | GlOS yield (%) | | | Degradation by-product yield (%) | | | |
|---|---|---|---|---|---|---|---|---|
|  |  | TOS | TM | GB | LGA | HMF | LA | FA |
| NaBr·6H$_2$O | 20.2 | 18.8 | 7.5 | 3.6 | 1.1 | 0.13 | 0.00 | 0.01 |
| MgCl$_2$·9H$_2$O | 10.0 | 3.8 | 1.9 | 3.9 | 0.3 | 0.05 | 0.00 | 0.01 |
| ZnCl$_2$·6H$_2$O | 11.1 | 0.0 | 0.0 | 0.0 | 0.2 | 0.71 | 0.00 | 0.01 |
| LiCl·3H$_2$O | 34.9 | 30.7 | 10.9 | 4.0 | 1.4 | 0.70 | 0.38 | 0.04 |
| LiBr·3H$_2$O | 47.9 | 42.2 | 11.8 | 2.6 | 1.8 | 1.56 | 0.71 | 0.18 |
| CaCl$_2$·6H$_2$O | 20.7 | 14.1 | 6.8 | 2.3 | 1.8 | 0.52 | 0.19 | 0.02 |
| CaBr$_2$·6H$_2$O | 28.0 | 23.0 | 9.1 | 2.4 | 3.5 | 0.75 | 0.49 | 0.05 |

Other conditions: The reactions were conducted in various MSH media containing 40 mM HCl at 110° C. for 10 min. The loading of glucose was 40% (w/v).

Example 12: Synthesis of Oligosaccharides from Lactose

Oligosaccharides (galactooligosaccharides, GOS) were synthesized from lactose alone or from a mixture of lactose and galactose. The addition of a monosaccharide (e.g., galactose) may be used to manipulate the sugar profile (e.g., the ratio of galactose to glucose), the molecular weight distribution, and the glycosidic bond diversity in the end oligosaccharides. Table 12 summarizes the yields of the oligosaccharides synthesized from lactose with/without galactose. Lactose was quantitatively (up to about 99%) converted and the resultant GOS yields reached over 66%, which were slightly higher than the GOS yields from the monosaccharides such as galactose and glucose. Lactose may be an excellent feedstock for GOS synthesis, since it is a by-product of the dairy industry.

TABLE 12

Galactooligosaccharide synthesis from either lactose or a mixture of lactose and galactose in ALBTH at 110° C. for 10 min

| Loading (%, w/v) | | | GOS yield (%) | Lactose conversion[1] (%) |
|---|---|---|---|---|
| Lactose | Galactose | Glucose |  |  |
| 100 |  |  | 66.6 | 97.8 |
| 50 | 50 |  | 66.1 | 98.6 |
|  | 80 | 20 | 64.6 |  |

[1]The major by-products of lactose conversion included galactose and glucose.

Example 13: Synthesis of Oligosaccharides from Sucrose

Oligosaccharides (fructooligosaccharides, FOS) were synthesized from sucrose alone or from a mixture of sucrose and fructose. The addition of a monosaccharide (e.g., fructose) can be used to manipulate the sugar profile (e.g., the ratio of fructose to glucose), the molecular weight distribution and the glycosidic bond diversity in the end oligosaccharides. Table 13 summarizes the yields of the oligosaccharides synthesized from sucrose with/without fructose. Sucrose was fully (100%) converted in ALBTH and the resultant FOS yield reached over 41%. A mixture of fructose and sucrose further increased the FOS yield to 50%.

TABLE 13

Preliminary investigation of fructooligosaccharide synthesis from ether sucrose or a mixture of sucrose and fructose in ALBTH at 70° C. for 60 min

| Loading (%, w/v) | | FOS yield (%) | Sucrose conversion[1] (%) |
|---|---|---|---|
| Sucrose | Fructose |  |  |
| 100 |  | 41.4 | 100.0 |
| 50 | 50 | 49.5 | 97.3 |
|  | 100 | 56.7 |  |

[1]The major by-products of sucrose conversion included fructose and glucose.

EQUIVALENTS

While certain embodiments have been illustrated and described, a person with ordinary skill in the art, after reading the foregoing specification, can effect changes, substitutions of equivalents and other types of alterations to the methods and oligosaccharides of the present technology or derivatives, nutraceutical compositions, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

The invention claimed is:

1. A method comprising mixing one or more types of monosaccharides, disaccharides, or a combination thereof with a water-deficient system at a temperature sufficient to form one or more types of prebiotic oligosaccharides, wherein
    the weight ratio of monosaccharides, disaccharides, or a combination thereof to water-deficient system is 0.01 to 10; and the water-deficient system comprises a metal salt selected from an alkali metal salt and/or an alkaline earth metal salt, water, and a catalytic amount of acid wherein
    the molar ratio of water to metal salt in the water-deficient system is about 2 to about 12; and
    the acid has a pKa of less than 4.

2. The method of claim 1 wherein the metal salt is a lithium salt.

3. The method of claim 1 wherein the metal salt is one or more selected from the group consisting of LiBr, LiCl, NaBr, $CaCl_2$, $CaBr_2$, $MgCl_2$, NaI, LiI, $CaI_2$, $MgI_2$, $AlCl_3$, $AlBr_3$, $MgBr_2$, $ZnCl_2$, $ZnBr_2$, $LiClO_4$, $Ca(ClO_4)_2$, LiSCN, and $Ca(SCN)_2$.

4. The method of claim 1 wherein the metal salt is lithium bromide.

5. The method of claim 1 wherein the molar ratio of water to metal salt in the water-deficient system is about 2 to about 5.

6. The method of claim 1 wherein the water deficient system is a solution.

7. The method of claim 1 wherein the acid has a pKa of about −10 to less than 4.

8. The method of claim 7 wherein the acid is one or more selected from the group consisting of HCl, $H_2SO_4$, $HNO_3$, $H_3PO_4$, $CH_3SO_3H$, tosylic acid, oxalic acid, glyoxylic acid, lactic acid, citric acid, formic acid, and trifluoroacetic acid.

9. The method of claim 1 wherein the water-deficient system comprises 0.5 mM to 500 mM acid.

10. The method of claim 1 wherein the monosaccharides, disaccharides, or combination thereof comprises glucose, fructose, galactose, xylose, mannose, arabinose, sucrose, lactose, maltose, cellobiose, apiose, rhamnose, hydrolyzed starch, hydrolyzed cellulose, hydrolyzed lignocellulosic biomass, or a combination of two or more thereof.

11. The method of claim 1, wherein the mixing comprises a combination of monosaccharides and disaccharides with the water-deficient system.

12. The method of claim 1 wherein the temperature is about 50° C. to about 160° C.

13. The method of claim 12 wherein the temperature is about 70° C. to about 120° C.

14. The method of claim 1 wherein the monosaccharides, disaccharides, or a combination thereof and the water deficient system are mixed for 1 minute to 2 days.

15. The method of claim 1 further comprising adding a diluting solvent to the mixture comprising prebiotic oligosaccharides to form a diluted mixture in which the metal salt remains substantially in solution.

16. The method of claim 15 wherein the diluting solvent is water or methanol.

17. The method of claim 15 further comprising adding a precipitating solvent to the diluted mixture to selectively precipitate the metal salt or metal salt and unreacted monosaccharides, disaccharides, or a combination thereof over the prebiotic oligosaccharides.

18. The method of claim 17 wherein the precipitating solvent is acetone, ethanol, isopropanol, methyl isobutyl ketone or a mixture of any two or more thereof.

19. The method of claim 17 further comprising recycling the precipitated metal salt to form another water deficient system.

20. The method of claim 1 further comprising purifying the prebiotic oligosaccharides.

21. The method of claim 20 wherein the purified prebiotic oligosaccharides contain less than 5% by weight metal salt.

22. The method of claim 20 wherein the purified prebiotic oligosaccharides contain less than 5% by weight HMF and furfural.

* * * * *